(12) United States Patent
Lu et al.

(10) Patent No.: US 8,945,564 B2
(45) Date of Patent: Feb. 3, 2015

(54) ANTAGONIST ANTI-CD40 ANTIBODY PHARMACEUTICAL COMPOSITIONS

(75) Inventors: Xiaofeng Lu, Fremont, CA (US); Bao-Lu Chen, San Ramon, CA (US); Kidisti Araya, Berkeley, CA (US); Augustus Okhamafe, Concord, CA (US)

(73) Assignees: Novartis AG, Basel (CH); Xoma Technology Ltd., Berkeley, CA (US)

( * ) Notice: Subject to any disclaimer, the term of this patent is extended or adjusted under 35 U.S.C. 154(b) by 1002 days.

(21) Appl. No.: 12/297,382

(22) PCT Filed: Apr. 17, 2007

(86) PCT No.: PCT/US2007/066757
§ 371 (c)(1),
(2), (4) Date: Feb. 20, 2009

(87) PCT Pub. No.: WO2007/124299
PCT Pub. Date: Nov. 1, 2007

(65) Prior Publication Data
US 2009/0304706 A1 Dec. 10, 2009

Related U.S. Application Data

(60) Provisional application No. 60/794,011, filed on Apr. 21, 2006.

(51) Int. Cl.
*A61K 39/395* (2006.01)
*C07K 16/28* (2006.01)

(52) U.S. Cl.
CPC ......... *C07K 16/2878* (2013.01); *C07K 2316/96* (2013.01)
USPC .................. 424/153.1; 424/130.1; 424/133.1; 424/141.1; 424/143.1; 424/144.1; 424/173.1; 530/387.1; 530/387.3; 530/388.1; 530/388.2; 530/388.22; 530/388.7

(58) Field of Classification Search
None
See application file for complete search history.

(56) References Cited

U.S. PATENT DOCUMENTS

| | | | |
|---|---|---|---|
| 5,397,703 A | 3/1995 | de Boer et al. | |
| 5,677,165 A | 10/1997 | de Boer et al. | |
| 5,801,227 A | 9/1998 | Fanslow, III et al. | |
| 5,874,082 A | 2/1999 | de Boer et al. | |
| 6,004,552 A | 12/1999 | de Boer et al. | |
| 6,056,959 A | 5/2000 | de Boer et al. | |
| 6,315,998 B1 | 11/2001 | de Boer et al. | |
| 6,899,879 B2 | 5/2005 | de Boer et al. | |
| 8,277,810 B2 | 10/2012 | Long et al. | |
| 8,637,032 B2 | 1/2014 | Long et al. | |
| 2003/0180253 A1* | 9/2003 | Chen et al. | 424/85.2 |
| 2003/0180287 A1 | 9/2003 | Gombotz et al. | |
| 2004/0022792 A1 | 2/2004 | Klinke et al. | |
| 2004/0197324 A1* | 10/2004 | Liu et al. | 424/130.1 |
| 2005/0004354 A1* | 1/2005 | Salfeld et al. | 530/388.23 |
| 2005/0175611 A1 | 8/2005 | Mahler et al. | |
| 2007/0020255 A1 | 1/2007 | Ueno et al. | |
| 2007/0098717 A1 | 5/2007 | Long et al. | |
| 2007/0098718 A1 | 5/2007 | Long et al. | |
| 2007/0110754 A1 | 5/2007 | Long et al. | |
| 2007/0184050 A1 | 8/2007 | Ishikawa et al. | |
| 2007/0218060 A1 | 9/2007 | Long et al. | |
| 2007/0244299 A1 | 10/2007 | Jaber | |
| 2008/0057070 A1 | 3/2008 | Long et al. | |
| 2008/0254026 A1 | 10/2008 | Long et al. | |
| 2013/0011405 A1 | 1/2013 | Long et al. | |
| 2014/0205602 A1 | 7/2014 | Long et al. | |

FOREIGN PATENT DOCUMENTS

| | | |
|---|---|---|
| EP | 1 391 464 A1 | 2/2004 |
| WO | WO 94/01547 A3 | 1/1994 |
| WO | WO 95/17202 A1 | 6/1995 |
| WO | WO 96/18413 A1 | 6/1996 |
| WO | WO 97/31025 A1 | 8/1997 |
| WO | WO 99/37329 | 7/1999 |
| WO | WO 99/42075 A2 | 8/1999 |
| WO | WO 01/24814 A1 | 4/2001 |
| WO | WO 01/34649 A3 | 5/2001 |
| WO | WO 01/83755 A3 | 11/2001 |
| WO | WO 02/04021 A1 | 1/2002 |
| WO | WO 02/22212 A2 | 3/2002 |
| WO | WO 02/28480 A2 | 4/2002 |
| WO | WO 02/28481 A2 | 4/2002 |
| WO | WO 02/28904 A3 | 4/2002 |

(Continued)

OTHER PUBLICATIONS

Balint, R., et al., "Antibody Engineering by Parsimonious Mutagenesis," *Gene*, 1993, pp. 109-118, vol. 137, No. 27.

Boon, L., et al., "Prevention of Experimental Autoimmune Encephalomyelitis in the Common Marmoset (*Callithrix jacchus*) Using a Chimeric Antagonist Monoclonal Antibody Against Human CD40 Is Associated with Altered B Cell Responses," *Journal of Immunology*, 2001, pp. 2942-2949, vol. 167, No. 5.

Ellmark, P., et al., "Modulation of the CD4O-CD40 Ligand Interaction Using Human Anti-CD40 Single-Chain Antibody Fragments Obtained from the n-CoDeR Phage Display Library," *Immunology*, 2002, pp. 456-463, vol. 106, No. 4.

(Continued)

*Primary Examiner* — Phillip Gambel
(74) *Attorney, Agent, or Firm* — Alston & Bird LLP

(57) ABSTRACT

Stable liquid pharmaceutical compositions comprising an antagonist anti-CD40 antibody as a therapeutically or prophylactically active component and methods useful in their preparation are provided. These compositions comprise the antagonist anti-CD40 antibody, a buffering agent to maintain the pH of the composition between about pH 5.0 and about pH 7.0, and an amount of arginine-HCl sufficient to render the liquid composition near isotonic. The stable liquid antagonist anti-CD40 antibody-containing pharmaceutical compositions of the invention find use in methods for treating proliferative diseases and diseases having an autoimmune and/or inflammatory component.

37 Claims, 16 Drawing Sheets

(56) References Cited

FOREIGN PATENT DOCUMENTS

| WO | WO 02/28905 A2 | 4/2002 |
|---|---|---|
| WO | WO 02/060485 A2 | 8/2002 |
| WO | WO 02/078766 | 10/2002 |
| WO | WO 02/088186 A1 | 11/2002 |
| WO | WO 03/029296 A1 | 4/2003 |
| WO | WO 03/039485 A2 | 5/2003 |
| WO | WO 03/045978 A3 | 6/2003 |
| WO | WO 03/072060 A2 | 9/2003 |
| WO | WO 2004/062689 A1 | 7/2004 |
| WO | WO 2004/110498 A2 | 12/2004 |
| WO | WO 2005/033143 A1 | 4/2005 |
| WO | WO 2005/044294 A2 | 5/2005 |
| WO | WO 2005/044304 A2 | 5/2005 |
| WO | WO 2005/044305 A2 | 5/2005 |
| WO | WO 2005/044306 A2 | 5/2005 |
| WO | WO 2005/044307 A2 | 5/2005 |
| WO | WO 2005/044854 A2 | 5/2005 |
| WO | WO 2005/044855 A2 | 5/2005 |
| WO | WO 2005/063291 A1 | 7/2005 |
| WO | WO 2005/117948 A1 | 12/2005 |
| WO | WO 2006/020935 | 2/2006 |
| WO | WO 2006/125207 | 11/2006 |
| WO | WO 2007/092772 | 8/2007 |

OTHER PUBLICATIONS

Funakoshi, S., et al., "Differential In Vitro and In Vivo Antitumor Effects Mediated by Anti-CD40 and Anti-CD20 Monoclonal Antibodies Against Human B-Cell Lymphomas," *Journal of Immunology*, 1996, vol. 19, No. 2, pp. 93-101.

Gisselbrecht, C., et al., "Interleukin-2 Treatment in Lymphoma: A Phase II Multicenter Study," *Blood*, 1994, pp. 2081-2085, vol. 83, No. 8.

Hager A-C Malmborg, et al., "Affinity and Epitope Profiling of Mouse Anti-CD40 Monoclonal Antibodies," *Scandinavian Journal of Immunology*, 2003, pp. 517-524, vol. 57, No. 6.

Ishibashi et al., "Is Arginine a Protein-Denaturant?" *Protein Expression and Purification*, 2005, pp. 1-6, vol. 42.

Little, M., et al., "Of Mice and Men: Hybridoma and Recombinant Antibodies," *Review Immunology Today*, 2000, pp. 364-370, vol. 21.

Mahler et al., "Induction and Analysis of Aggregates in a Liquid IgG1-Antibody Formulation," *European Journal of Pharmaceutics and Biopharmaceutics*, 2005, pp. 407-417, vol. 59.

Maloney, D.G., et al., "IDEC-C2B8: Results of a Phase I Multiple-Dose Trial in Patients with Relapsed Non-Hodgkin's Lymphoma," *Journal of Clinical Oncology*, 1997, vol. 15, No. 10, pp. 3266-3274.

Matheus, et al. "A Critical Evaluation of $T_{m(FTIR)}$ Measurements of High-Concentration $IgG_1$ Antibody Formulations as a Formulation Development Tool," *Pharmaceutical Research*, 2006, pp. 1617-1627, vol. 23.

Rosenberg, S.A., et al., "A Progress Report on the Treatment of 157 Patients with Advanced Cancer Using Lymphokine-Activated Killer Cells and Interleukin-2 or High-Dose Interleukin-2 Alone," *The New England Journal of Medicine*, 1987, pp. 889-897, vol. 316, No. 15.

Tai, Y., et al., "Mechanisms by which SGN-40, a Humanized Anti-CD40 Antibody, Induces Cytotoxicity in Human Multiple Myeloma Cells: Clinical Implications," *Cancer Research*, 2004, pp. 2846-2852, vol. 64, No. 8.

Tsumoto et al., "Role of Arginine in Protein Refolding, Solubilization, and Purification," *Biotechnol. Prog.*, 2004, pp. 1301-1308, vol. 20.

Wang, "Instability, Stabilization, and Formulation of Liquid Protein Pharmaceuticals," *International Journal of Pharmaceutics*, 1999, pp. 129-188, vol. 185.

Weng Wen-Kai, et al., "Human anti-CD40 Antagonistic Antibodies Inhibit the Proliferation of Human B Cell Non-Hodgkin's Lymphoma," *Blood*, 2001, p. 466a, vol. 98, No. 11, Part 1, Abstract #1947.

Zheng et al., "Influence of pH, Buffer Species, and Storage Temperature on Physicochemical Stability of a Humanized Monoclonal Antibody LA298," *International Journal of Pharmaceutics*, 2006, pp. 46-51, vol. 308.

Baynes, B., et al., "Role of Arginine in the Stabilization of Proteins against Aggregation," *Biochemistry*, 2005, vol. 44, pp. 4919-4925.

Chen, B., et al., "Influence of Histidine on the Stability and Physical Properties of a Fully Human Antibody in Aqueous and Solid Forms," *Pharmaceutical Research*, 2003, vol. 20(12), pp. 1952-1960.

Shire, S., et al., "Challenges in the Development of High Protein Concentration Formulations," *Journal of Pharmaceutical Sciences*, Jun. 2004, pp. 1390-1402, vol. 93(6), Wiley-Liss, Inc. and the American Pharmacists Association.

Sukumar, M., et al., "Opalescent Appearance of an IgG1 Antibody at High Concentrations and Its Relationship to Noncovalent Association," *Pharmaceutical Research*, Jul. 2004, pp. 1087-1093, vol. 21(7), Plenum Publishing Corporation.

\* cited by examiner

ANTAGONIST ANTI-CD40 ANTIBODY PHARMACEUTICAL COMPOSITIONS

CROSS REFERENCE TO RELATED APPLICATIONS

This application is a U.S. national-stage application of International Patent Application No. PCT/US2007/066757, filed Apr. 17, 2007, which claims the benefit of U.S. Provisional Application No. 60/794,011, filed on Apr. 21, 2006.

FIELD OF THE INVENTION

The present invention is directed to the field of pharmaceutical formulations, more particularly to stable liquid pharmaceutical compositions comprising antagonist anti-CD40 antibodies for use in treating proliferative diseases and diseases having an autoimmune or inflammatory component.

BACKGROUND OF THE INVENTION

Recent advances in the development of genetic engineering technology have provided a variety of biologically active polypeptides in sufficiently large quantities for use as drugs. Polypeptides, however, can lose biological activity as a result of physical instabilities, including denaturation and formation of soluble and insoluble aggregates, and a variety of chemical instabilities, such as hydrolysis, oxidation, and deamidation. Stability of polypeptides in liquid pharmaceutical formulations can be affected, for example, by factors such as pH, ionic strength, temperature, repeated cycles of freeze-thaw, and exposure to mechanical shear forces such as occur during processing. Aggregate formation and loss of biological activity can also occur as a result of physical agitation and interactions of polypeptide molecules in solution and at the liquid-air interfaces within storage vials. Further conformational changes may occur in polypeptides adsorbed to air-liquid and solid-liquid interfaces during compression-extension of the interfaces resulting from agitation during transportation or otherwise. Such agitation can cause the protein to entangle, aggregate, form particles, and ultimately precipitate with other adsorbed proteins. For a general review of stability of protein pharmaceuticals, see, for example, Manning et al. (1989) *Pharm. Res.* 6:903-918, and Wang and Hanson (1988) *J. Parenteral Sci. Tech.* 42:S14.

Instability of polypeptide-containing liquid pharmaceutical formulations has prompted packaging of these formulations in the lyophilized form along with a suitable liquid medium for reconstitution. Although lyophilization improves storage stability of the composition, many polypeptides exhibit decreased activity, either during storage in the dried state (Pikal (1990) *Biopharm.* 27:26-30) or as a result of aggregate formation or loss of catalytic activity upon reconstitution as a liquid formulation (see, for example, Carpenter et al. (1991) *Develop. Biol. Standard* 74:225-239; Broadhead et al. (1992) *Drug Devel. Ind. Pharm.* 18:1169-1206; Mumenthaler et al. (1994) *Pharm. Res.* 11: 12-20; Carpenter and Crowe (1988) *Cryobiology* 25:459-470; and Roser (1991) *Biopharm.* 4:47-53). While the use of additives has improved the stability of dried proteins, many rehydrated formulations continue to have unacceptable or undesirable amounts of inactive, aggregated protein (see, for example, Townsend and DeLuca (1983) *J. Pharm. Sci.* 80:63-66; Hora et al. (1992) *Pharm. Res.* 9:33-36; Yoshiaka et al. (1993) *Pharm. Res,* 10:687-691). Also, the need for reconstitution is an inconvenience and introduces the possibility of incorrect dosing.

Included in the pharmaceutically useful polypeptides are recombinantly produced monoclonal antibodies. Among this class of therapeutic agents, the antagonist anti-CD40 antibodies targeting the TNF family receptor member CD40 hold great promise for the treatment of B-cell related malignancies and non-hematological malignancies, as well as diseases having an autoimmune and/or inflammatory component. The CD40 receptor is a 50-55 kDa cell-surface antigen present on the surface of both normal and neoplastic human B cells, dendritic cells, monocytes, macrophages, CD8$^+$ T cells, endothelial cells, monocytic and epithelial cells, some epithelial carcinomas, and many solid tumors, including lung, breast, ovary, urinary bladder, and colon cancers. The CD40 antigen is also expressed on activated T cells, activated platelets, inflamed vascular smooth muscle cells, eosinophils, synovial membranes in rheumatoid arthritis, dermal fibroblasts, and other non-lymphoid cell types. Depending on the type of cell expressing CD40, ligation can induce intercellular adhesion, differentiation, activation, and proliferation.

For example, binding of CD40 to its cognate ligand, CD40L (also designated CD154), stimulates B-cell proliferation and differentiation into plasma cells, antibody production, isotype switching, and B-cell memory generation. During B-cell differentiation, CD40 is expressed on pre-B cells but lost upon differentiation into plasma cells. CD40 expression on APCs plays an important co-stimulatory role in the activation of these cells. For example, agonistic anti-CD40 monoclonal antibodies (mAbs) have been shown to mimic the effects of T helper cells in B-cell activation. When presented on adherent cells expressing FcγRII, these antibodies induce B-cell proliferation (Banchereau et al. (1989) *Science* 251: 70). Moreover, agonistic anti-CD40 mAbs can replace the T helper signal for secretion of IgM, IgG, and IgE in the presence of IL-4 (Gascan et al. (1991) *J. Immunol.* 147:8). Furthermore, agonistic anti-CD40 mAbs can prevent programmed cell death (apoptosis) of B cells isolated from lymph nodes.

These and other observations support the current theory that the interaction of CD40 and CD40L plays a pivotal role in regulating both humoral and cell-mediated immune responses. More recent studies have revealed a much broader role of CD40/CD40L interaction in diverse physiological and pathological processes.

Thus, CD40 engagement by CD40L and subsequent activation of CD40 signaling are necessary steps for normal immune responses; however, dysregulation of CD40 signaling can lead to disease. The CD40 signaling pathway has been shown to be involved in autoimmune disease (Ichikawa et al. (2002) *J. Immunol.* 169:2781-2787 and Moore et al. (2002) *J. Autoimmun.* 19:139-145). Additionally, the CD40/CD40L interaction plays an important role in inflammatory processes. For example, both CD40 and CD40L are overexpressed in human and experimental atherosclerosis lesions. CD40 stimulation induces expression of matrix-degrading enzymes and tissue factor expression in atheroma-associated cell types, such as endothelial cells, smooth muscle cells, and macrophages. Further, CD40 stimulation induces production of proinflammatory cytokines such as IL-1, IL-6, and IL-8, and adhesion molecules such as ICAM-1, E-selectin, and VCAM. Inhibition of CD40/CD40L interaction prevents atherogenesis in animal models. In transplant models, blocking CD40/CD40L interaction prevents inflammation. It has been shown that CD40/CD40L binding acts synergistically with the Alzheimer amyloid-beta peptide to promote microglial activation, thus leading to neurotoxicity. In patients with rheumatoid arthritis (RA), CD40 expression is increased on articular chondrocytes, thus, CD40 signaling likely contributes to production of damaging cytokines and matrix metalloproteinases. See, Gotoh et al. (2004) *J. Rheumatol.* 31:1506-1512.

Similarly, malignant B cells from tumor types of B-cell lineage express CD40 and appear to depend on CD40 signaling for survival and proliferation. Transformed cells from patients with low- and high-grade B-cell lymphomas, B-cell acute lymphoblastic leukemia, multiple myeloma, chronic lymphocytic leukemia, Walsdenstrom's Macroglobulinemia, and Hodgkin's disease express CD40. CD40 expression is also detected in two-thirds of acute myeloblastic leukemia cases and 50% of AIDS-related lymphomas.

A number of carcinomas and sarcomas also exhibit high levels of CD40 expression, though the role of CD40 signaling in relation to CD40 expression on these cancer cells is less well understood. CD40-expressing carcinomas include urinary bladder carcinoma (Paulie et al. (1989) *J. Immunol.* 142:590-595; Braesch-Andersen et al. (1989) *J. Immunol.* 142:562-567), breast carcinoma (Hirano et al. (1999) *Blood* 93:2999-3007; Wingett et al. (1998) *Breast Cancer Res. Treat.* 50:27-36); prostate cancer (Rokhlin et al. (1997) *Cancer Res.* 57:1758-1768), renal cell carcinoma (Kluth et al. (1997) *Cancer Res.* 57:891-899), undifferentiated nasopharyngeal carcinoma (UNPC) (Agathanggelou et al. (1995) *Am. J. Pathol.* 147:1152-1160), squamous cell carcinoma (SCC) (Amo et al. (2000) *Eur. J. Dermatol.* 10:438-442; Posner et al. (1999) *Clin. Cancer Res.* 5:2261-2270), thyroid papillary carcinoma (Smith et al. (1999) *Thyroid* 9:749-755), cutaneous malignant melanoma (van den Oord et al. (1996) *Am. J. Pathol.* 149:1953-1961), gastric carcinoma (Yamaguchi et al. (2003) *Int. J. Oncol.* 23(6): 1697-702), and liver carcinoma (see, for example, Sugimoto et al. (1999) *Hepatology* 30(4): 920-26, discussing human hepatocellular carcinoma). For CD40-expressing sarcomas, see, for example, Lollini et al. (1998) *Clin. Cancer Res.* 4(8):1843-849, discussing human osteosarcoma and Ewing's sarcoma.

Given the potential therapeutic benefits of antagonist anti-CD40 antibodies in regulating CD40L-mediated CD40 signaling in various cancer and autoimmune/inflammatory diseases, and the challenges of formulating these polypeptides, stable pharmaceutical compositions comprising these antibodies are needed.

BRIEF SUMMARY OF THE INVENTION

Stable liquid pharmaceutical compositions comprising an antagonist anti-CD40 antibody as a therapeutically or prophylactically active component and methods useful in their preparation are provided. These compositions comprise the antagonist anti-CD40 antibody, a buffering agent to maintain the pH of the composition between about pH 5.0 and about pH 7.0, and an amount of arginine-HCl sufficient to render the liquid composition near isotonic. In some embodiments, the buffering agent is a citrate/citric acid buffer, the antagonist anti-CD40 antibody is the CHIR-12.12 or CHIR-5.9 antagonist anti-CD40 antibody or antigen-binding fragment thereof, the composition comprises arginine-HCl as the isotonizing agent, and the composition further comprises a nonionic surfactant and/or L-methionine as further stabilizing agents. The stable liquid antagonist anti-CD40 antibody-containing pharmaceutical compositions of the invention find use in methods for treating proliferative diseases and diseases having an autoimmune and/or inflammatory component.

BRIEF DESCRIPTION OF THE SEVERAL VIEWS OF THE DRAWING(S)

DETAILED DESCRIPTION OF THE INVENTION

Figure 1:
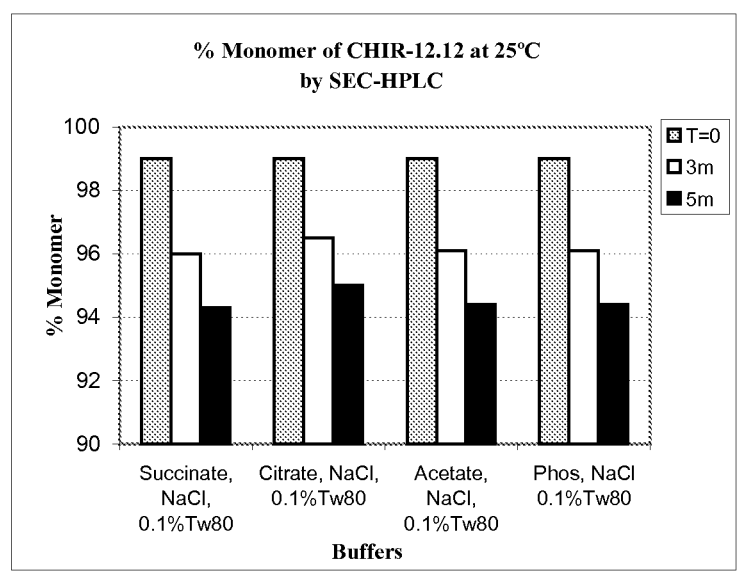
FIG. 1 shows the effect of buffer species on purity of mAb CHIR-12.12 formulations stored at 25° C. for 3 months or 5 months as measured by SEC-HPLC analysis.

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The present invention is directed to stable liquid pharmaceutical compositions comprising at least one antagonist anti-CD40 antibody or antigen-binding fragment thereof as a therapeutically or prophylactically active component, and to methods useful in their preparation. For purposes of the present invention, the term "liquid" with regard to pharmaceutical compositions or formulations is intended to include the term "aqueous." By "therapeutically or prophylactically active component" is intended the antagonist anti-CD40 antibody or antigen-binding fragment thereof is specifically incorporated into the composition to bring about a desired therapeutic or prophylactic response with regard to treatment, prevention, or diagnosis of a disease or condition within a subject when the pharmaceutical composition is administered to that subject.

By "stable" is intended the pharmaceutical compositions of the invention provide for the physical and/or chemical stability of the antagonist anti-CD40 antibody or antigen-binding fragment thereof. That is, the antagonist anti-CD40 antibody or antigen-binding fragment thereof essentially retains its physical and/or chemical stability and has the desired biological activity, i.e., one or more of the antagonist activities defined elsewhere herein, including, but not limited to: inhibition of immunoglobulin secretion by normal human peripheral B cells stimulated by T cells; inhibition of survival and/or proliferation of normal human peripheral B cells stimulated by Jurkat T cells; inhibition of survival and/or proliferation of normal human peripheral B cells stimulated by CD40L-expressing cells or soluble CD40 ligand (sCD40L); inhibition of "survival" anti-apoptotic intracellular signals in any cell stimulated by sCD40L or solid-phase CD40L; inhibition of CD40 signal transduction in any cell upon ligation with sCD40L or solid-phase CD40L; inhibition of proliferation of human malignant B cells; deletion, anergy and/or tolerance induction of CD40-bearing target cells or cells bearing cognate ligands to CD40 including, but not limited to, T cells and B cells; induction of expansion or activation of $CD4^+$ $CD25^+$ regulatory T cells (see for example, donor alloantigen-specific tissue rejection via CD40-CD40L interference, van Maurik et al. (2002) *J. Immunol.* 169:5401-5404); cytotoxicity via any mechanism (including, but not limited to, antibody-dependent cell-mediated cytotoxicity (ADCC), complement-dependent cytotoxicity (CDC), down-regulation of proliferation, and/or apoptosis in target cells); modulation of target cell cytokine secretion and/or cell surface molecule expression; and combinations thereof.

Methods for monitoring protein stability are well known in the art. See, for example, Jones (1993) *Adv. Drug Delivery Rev.* 10:29-90; Lee, ed. (1991) *Peptide and Protein Drug Delivery* (Marcel Dekker, Inc., New York, N.Y.); and the stability assays disclosed herein below. Generally, protein stability is measured at a chosen temperature for a specified period of time. In preferred embodiments, a stable antibody pharmaceutical composition provides for stability of the antagonist anti-CD40 antibody or antigen-binding fragment thereof when stored at room temperature (about 25° C.) for at least 1 month, at least 3 months, or at least 6 months, and/or is stable at about 2-8° C. for at least 6 months, at least 9 months, at least 12 months, at least 18 months, at least 24 months.

A protein such as an antibody, when formulated in a pharmaceutical composition, is considered to retain its physical stability at a given point in time if it shows no visual signs (i.e., discoloration or loss of clarity) or measurable signs (for example, using size-exclusion chromatography (SEC) or UV light scattering) of precipitation, aggregation, and/or denaturation in that pharmaceutical composition. With respect to chemical stability, a protein such as an antibody, when formulated in a pharmaceutical composition, is considered to retain its chemical stability at a given point in time if measurements of chemical stability are indicative that the protein (i.e., antibody) retains the biological activity of interest in that pharmaceutical composition. Methods for monitoring changes in chemical stability are well known in the art and include, but are not limited to, methods to detect chemically altered forms of the protein such as result from clipping, using, for example, SDS-PAGE, SEC, and/or matrix-assisted laser desorption ionization/time of flight mass spectrometry; and degradation associated with changes in molecular charge (for example, associated with deamidation), using, for example, ion-exchange chromatography. See, for example, the methods disclosed herein below.

An antagonist anti-CD40 antibody or antigen-binding fragment thereof, when formulated in a pharmaceutical composition, is considered to retain a desired biological activity at a given point in time if the desired biological activity at that time is within about 30%, preferably within about 20% of the desired biological activity exhibited at the time the pharmaceutical composition was prepared as determined in a suitable assay for the desired biological activity. Assays for measuring the desired biological activity of the antagonist anti-CD40 antibodies disclosed herein, and antigen-binding fragments thereof, can be performed as described in provisional applications entitled "Antagonist Anti-CD40 Monoclonal Antibodies and Methods for Their Use," filed Nov. 4, 2003, Nov. 26, 2003, and Apr. 27, 2004, and assigned U.S. Patent Application Nos. 60/517,337, 60/525,579, and 60/565,710, respectively; and International Patent Application No. PCT/US2004/037152, also entitled "Antagonist Anti-CD40 Monoclonal Antibodies and Methods for Their Use," filed Nov. 4, 2004, and published as WO 2005/044854; the contents of each of which are herein incorporated by reference in their entirety. See also the assays described in provisional application entitled "Methods for Diagnosis and Treatment of Proliferative Disorders Mediated by CD40 Signaling," filed Dec. 9, 2005, and assigned U.S. Patent Application No. 60/749,285, and corresponding International Patent Application No. PCT/US2006/019414, filed May 18, 2006, and published as WO 2006/125143; and provisional application entitled "Methods for Diagnosis and Treatment of Diseases Having an Autoimmune and/or Inflammatory Component," filed Dec. 9, 2005, and assigned U.S. Patent Application No. 60/749,336, and corresponding International Patent Application No. PCT/US2006/019325, filed May 18, 2006, and published as WO 2006/125117; the contents of each of which are herein incorporated by reference in their entirety. Also see the assays described in Schultze et al. (1998) *Proc. Natl. Acad. Sci. USA* 92:8200-8204; Denton et al. (1998) *Pediatr. Transplant.* 2:6-15; Evans et al. (2000) *J. Immunol.* 164:688-697;

Noelle (1998) *Agents Actions Suppl.* 49:17-22; Lederman et al. (1996) *Curr. Opin. Hematol.* 3:77-86; Coligan et al. (1991) *Current Protocols in Immunology* 13:12; Kwekkeboom et al. (1993) *Immunology* 79:439-444; and U.S. Pat. Nos. 5,674,492 and 5,847,082; herein incorporated by reference.

The antagonist anti-CD40 antibody or antigen-binding fragment thereof that is to be formulated in accordance with the methods of the present invention can be prepared using any method known in the art, including those methods disclosed elsewhere herein. In one embodiment, the antagonist anti-CD40 antibody, for example, the CHIR-12.12 or CHIR-5.9 monoclonal antibody, or antigen-binding fragment thereof is recombinantly produced in a CHO cell line as described herein below.

Following its preparation and purification, the antagonist anti-CD40 antibody or antigen-binding fragment thereof can be formulated as a liquid pharmaceutical composition in the manner set forth herein. Where the antagonist anti-CD40 antibody or antigen-binding fragment thereof is to be stored prior to its formulation, it can be frozen, for example, at ≤−20° C., and then thawed at room temperature for further formulation.

The liquid pharmaceutical compositions of the invention comprise a therapeutically or prophylactically effective amount of the antagonist anti-CD40 antibody or antigen-binding fragment thereof. The amount of antibody or antigen-binding fragment thereof present in the formulation takes into consideration the route of administration and desired dose volume.

In this manner, the liquid pharmaceutical compositions of the present invention comprise the antagonist anti-CD40 antibody, for example, the CHIR-12.12 or CHIR-5.9 antibody, or antigen-binding fragment thereof at a concentration of about 0.1 mg/ml to about 50.0 mg/ml, about 0.5 mg/ml to about 40.0 mg/ml, about 1.0 mg/ml to about 35.0 mg/ml, about 1.0 mg/ml to about 30.0 mg/ml, about 5.0 mg/ml to about 25.0 mg/ml, about 5.0 mg/ml to about 20.0 mg/ml, about 10.0 mg/ml to about 35.0 mg/ml, or about 15.0 mg/ml to about 25.0 mg/ml. In some embodiments, the liquid pharmaceutical composition comprises the antagonist anti-CD40 antibody or antigen-binding fragment thereof at a concentration of about 0.1 mg/ml to about 5.0 mg/ml, about 5.0 mg/ml to about 10.0 mg/ml, about 10.0 mg/ml to about 15.0 mg/ml, about 15.0 mg/ml to about 20.0 mg/ml, about 20.0 mg/ml to about 25.0 mg/ml, about 25.0 mg/ml to about 30.0 mg/ml, about 30.0 mg/ml to about 35.0 mg/ml, about 35.0 mg/ml to about 40.0 mg/ml, about 40.0 mg/ml to about 45.0 mg/ml, or about 45.0 mg/ml to about 50.0 mg/ml. In other embodiments, the liquid pharmaceutical composition comprises the antagonist anti-CD40 antibody or antigen-binding fragment thereof at a concentration of about 15.0 mg/ml, about 16.0 mg/ml, about 17.0 mg/ml, about 18.0 mg/ml, about 19.0 mg/ml, about 20.0 mg/ml, about 21.0 mg/ml, about 22.0 mg/ml, about 23.0 mg/ml, about 24.0 mg/ml, about 25.0 mg/ml, about 26.0 mg/ml, about 27.0 mg/ml, about 28.0 mg/ml, about 29.0 mg/ml, about 30.0 mg/ml, about 31.0 mg/ml, about 32.0 mg/ml, about 33.0 mg/ml, about 34.0 mg/ml, or about 35.0 mg/ml.

In accordance with the present invention, the antagonist anti-CD40 antibody, for example, the monoclonal antibody CHIR-12.12 or CHIR-5.9 described herein below, or antigen-binding fragment thereof, is formulated with a buffer that maintains the pH of the pharmaceutical composition in the range of about pH 5.0 to about pH 7.0, and an amount of arginine in its acidic form, referred to herein as arginine-HCl, sufficient to render the composition near isotonic. By "near isotonic" is intended the aqueous formulation has an osmolality of about 240 mmol/kg to about 360 mmol/kg, preferably about 240 to about 340 mmol/kg, more preferably about 250 to about 330 mmol/kg, even more preferably about 260 to about 320 mmol/kg, still more preferably about 270 to about 310 mmol/kg. In some embodiments, the liquid pharmaceutical composition has an osmolality of about 295 mmol/kg. Methods of determining the isotonicity of a solution are known to those skilled in the art. See, for example, Setnikar et al. (1959) *J. Am. Pharm. Assoc.* 48:628.

The arginine-HCl not only serves as an isotonizing agent, but also serves to stabilize the antibody against conformational changes, aggregate formation, fragmentation, and/or deamidation during storage of the liquid pharmaceutical compositions of the invention. By "during storage" is intended a liquid pharmaceutical composition or formulation once prepared, is not immediately administered to a subject. Rather, following preparation, it is packaged for storage, either in a liquid form, in a frozen state, or in a dried form for later reconstitution into a liquid form or other form suitable for administration to a subject. By "dried form" is intended the liquid pharmaceutical composition or formulation is dried either by freeze drying (i.e., lyophilization; see, for example, Williams and Polli (1984) *J. Parenteral Sci. Technol.* 38:48-59), spray drying (see Masters (1991) in *Spray-Drying Handbook* (5th ed; Longman Scientific and Technical, Essez, U.K.), pp. 491-676; Broadhead et al. (1992) *Drug Devel. Ind. Pharm.* 18:1169-1206; and Mumenthaler et al. (1994) *Pharm. Res.* 11: 12-20), or air drying (Carpenter and Crowe (1988) *Cryobiology* 25:459-470; and Roser (1991) *Biopharm.* 4:47-53). Conformational changes, aggregate formation, fragmentation, and/or deamidation of an antibody during storage of a liquid pharmaceutical composition can adversely affect biological activity of the antibody, resulting in loss of therapeutic efficacy of the pharmaceutical composition. Furthermore, aggregate formation may cause other problems such as blockage of tubing, membranes, or pumps when the antibody-containing pharmaceutical composition is administered using an infusion system.

Any stereoisomer (i.e., L, D, or DL isomer) of arginine, or combinations of these stereoisomers, may be present in the pharmaceutical compositions of the invention so long as the arginine is present in its acidic form, i.e., arginine-HCl. Preferably the L-stereoisomer is used. Compositions of the invention may also be formulated with analogues of this amino acid. By "amino acid analogue" is intended a derivative of the naturally occurring amino acid that brings about the desired effect of rendering the composition near isotonic as well as decreasing aggregate formation, fragmentation, and/or deamidation of the polypeptide during storage of the liquid pharmaceutical compositions of the invention. Suitable arginine analogues include, for example, aminoguanidine and N-monoethyl L-arginine. As with the arginine, the amino acid analogues are incorporated into the compositions in their acidic form.

The concentration of arginine-HCl in the pharmaceutical composition will depend upon the contribution of other components to tonicity. In some embodiments, the concentration of arginine-HCl is about 50 mM to about 300 mM, about 50 mM to about 250 mM, about 50 mM to about 200 mM, about 50 mM to about 175 mM, about 50 mM to about 150 mM, about 75 mM to about 175 mM, about 75 mM to about 150 mM, about 100 mM to about 175 mM, about 100 mM to about 200 mM, about 100 mM to about 150 mM, about 125 mM to about 175 mM, about 125 mM to about 150 mM, about 130 mM to about 170 mM, about 130 mM to about 160 mM, about 135 mM to about 155 mM, about 140 mM to about 155 mM, or about 145 mM to about 155 mM. In one such embodiment, the concentration of arginine-HCl is about 125 mM, about 150 mM, or about 175 mM.

The pH of a liquid antibody-containing pharmaceutical composition affects the stability of the antibody contained therein, primarily through its affect on polypeptide aggregate formation. Thus the amount of buffering agent present in the pharmaceutical compositions of the invention will vary depending upon the pH optimum for stability of a particular antagonist anti-CD40 antibody of interest. Determination of this pH optimum can be achieved using methods generally available in the art, including, for example, Differential Scanning Calorimetry (DSC), which assesses conformational stability; SDS-PAGE and size-exclusion chromatography (SEC-HPLC), which assess aggregation and fragmentation; and Cation-Exchange HPLC(CIEX-HPLC) analysis, which assesses charge change-related degradation. Preferred pH for the liquid pharmaceutical compositions of the invention is about pH 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, and other such values within the range of about pH 5.0 to about pH 7.0. In some embodiments, the buffering agent maintains the pH of the pharmaceutical composition in the range of about pH 5.0 to about pH 6.5, about pH 5.0 to about pH 6.0, about pH 5.0 to about pH 5.5, about pH 5.5 to about 7.0, about pH 5.5 to about pH 6.5, or about pH 5.5 to about pH 6.0.

Any suitable buffering agent that maintains the pH of the liquid antagonist anti-CD40 antibody pharmaceutical composition in the range of about pH 5.0 to about pH 7.0 can be used in the formulation, so long as the physicochemical stability and desired biological activity of the antibody are retained as noted herein above. Suitable buffering agents include, but are not limited to, conventional acids and salts thereof, where the counter ion can be, for example, sodium, potassium, ammonium, calcium, or magnesium. Examples of conventional acids and salts thereof that can be used to buffer the liquid pharmaceutical composition include, but are not limited to, citric acid or citrate, succinic acid or succinate, acetic acid or acetate, tartaric acid or tartarate, phosphoric acid or phosphate, gluconic acid or gluconate, glutamic acid or glutamate, aspartic acid or aspartate, maleic acid or maleate, and malic acid or malate buffers. It is recognized that the buffering agent can be a mixture of the acid and the salt form of the acid, for example, a mixture of citric acid and citrate (referred to herein as a citrate/citric acid buffer), a mixture of succinic acid and succinate (referred to herein as a succinate/succinic acid buffer), a mixture of acetic acid and acetate (referred to herein as an acetate/acetic acid buffer), and the like for each of the foregoing acid/acid salt pairs. The concentration of the buffering agent can be from about 1 mM to about 50 mM, including about 1 mM, 2 mM, 5 mM, 8 mM, 10 mM, 15 mM, 20 mM, 25 mM, 30 mM, 35 mM, 40 mM, 45 mM, 50 mM, or other such values within the range of about 1 mM to about 50 mM. In some embodiments, the concentration of the buffering agent is from about 5 mM to about 15 mM, including about 5 mM, 6 mM, 7 mM, 8 mM, 9 mM, 10 mM, 11 mM, 12 mM, 13 mM, 14 mM, 15 mM, or other such values within the range of about 5 mM to about 15 mM.

In some embodiments of the invention, the liquid pharmaceutical composition comprises the desired concentration (i.e., about 0.1 mg/ml to about 50.0 mg/ml as noted above) of an antagonist anti-CD40 antibody described elsewhere herein, for example, the monoclonal antibody CHIR-12.12 or CHIR-5.9, or antigen-binding fragment thereof, an amount of arginine-HCl to render the composition near isotonic, and a buffering agent that is a citrate/citric acid buffer, where the concentration of the buffering agent is such that the buffering agent maintains the pH of the pharmaceutical composition in the range of about pH 5.0 to about pH 7.0, preferably about pH 5.0 to about pH 6.5, including about pH 5.0, 5.5, 6.0, and 6.5. By "citrate" is intended a buffer comprising a salt of citric acid. In a preferred embodiment, the citrate counterion is the sodium cation, and thus the citrate buffer component is sodium citrate. However, any cation is expected to be effective. Other possible citrate cations include, but are not limited to, potassium, ammonium, calcium, and magnesium. As noted above, a citrate/citric acid buffer comprises a mixture of the acid (i.e., citric acid) and the salt form of the acid (i.e., citrate), where the counterion in the salt form of the acid can be any suitable cation. In one such embodiment, the counter ion for the salt form of the acid is the sodium cation, and hence the buffering agent comprises a mixture of citric acid and sodium citrate. As noted above, the concentration of the citrate/citric acid buffer can be from about 1 mM to about 50 mM, including about 1 mM, 2 mM, 5 mM, 8 mM, 10 mM, 15 mM, 20 mM, 25 mM, 30 mM, 35 mM, 40 mM, 45 mM, 50 mM, or other such values within the range of about 1 mM to about 50 mM. In some embodiments, the citrate/citric acid buffer concentration is from about 5 mM to about 15 mM, including about 5 mM, 6 mM, 7 mM, 8 mM, 9 mM, 10 mM, 11 mM, 12 mM, 13 mM, 14 mM, or about 15 mM.

In other embodiments, the liquid pharmaceutical composition comprises an antagonist anti-CD40 antibody such as the monoclonal antibody CHIR-12.12 or CHIR-5.9, or antigen-binding fragment thereof, at a concentration of about 0.1 mg/ml to about 50.0 mg/ml, about 5.0 mg/ml to about 35.0 mg/ml, about 10.0 mg/ml to about 35.0 mg/ml, or about 10.0 mg/ml to about 20.0 mg/ml; an amount of arginine-HCl to render the composition near isotonic; and the buffering agent is a citrate/citric acid buffer at a concentration of about 1 mM to about 20 mM, about 5 mM to about 15 mM, preferably about 10 mM. In yet other embodiments, the liquid pharmaceutical composition comprises an antagonist anti-CD40 antibody such as the monoclonal antibody CHIR-12.12 or CHIR-5.9, or antigen-binding fragment thereof, at a concentration of about 0.1 mg/ml to about 50.0 mg/ml, about 5.0 mg/ml to about 35.0 mg/ml, about 10.0 mg/ml to about 35.0 mg/ml, or about 10.0 mg/ml to about 20.0 mg/ml; an amount of arginine-HCl to render the composition near isotonic; and the buffering agent is sodium citrate/citric acid buffer at a concentration of about 1 mM to about 20 mM, about 5 mM to about 15 mM, preferably about 10 mM.

In some preferred embodiments, the liquid pharmaceutical composition comprises the antagonist anti-CD40 antibody, for example, the monoclonal antibody CHIR-12.12 or CHIR-5.9, or antigen-binding fragment thereof, a buffering agent to maintain the pH of the pharmaceutical composition within the range of about pH 5.0 to about pH 7.0; and the concentration of arginine-HCl is about 100 mM to about 200 mM. In some of these embodiments, the buffering agent is sodium citrate/citric acid buffer at a concentration of about 5 mM to about 15 mM, the liquid pharmaceutical composition comprises the antagonist anti-CD40 antibody, for example, the monoclonal antibody CHIR-12.12 or CHIR-5.9, or antigen-binding fragment thereof, and the pharmaceutical composition has a pH of about pH 5.0 to about pH 7.0, about pH 5.0 to about pH 6.5, or about pH 5.5 to about pH 6.0. In other embodiments, the liquid pharmaceutical composition comprises the antagonist anti-CD40 antibody, for example, the monoclonal antibody CHIR-12.12 or CHIR-5.9, or antigen-binding fragment thereof, at a concentration of about 0.1 mg/ml to about 50.0 mg/ml, about 5.0 mg/ml to about 35.0 mg/ml, or about 10.0 mg/ml to about 35.0 mg/ml, including about 10.0 mg/ml, about 15.0 mg/ml, about 20.0 mg/ml, about 25.0 mg/ml, about 30.0 mg/ml, or about 35.0 mg/ml; about 150 mM arginine-HCl; and the buffering agent is about 10 mM sodium citrate/citric acid buffer; where the formulation has a pH of about pH 5.5.

Protein degradation due to freeze thawing or mechanical shearing during processing of liquid pharmaceutical formulations of the present invention can be inhibited by incorporation of surfactants into the formulation in order to lower the surface tension at the solution-air interface. Thus, in some embodiments, the liquid pharmaceutical composition comprises an antagonist anti-CD40 antibody, for example, the monoclonal antibody CHIR-12.12 or CHIR-5.9, or antigen-binding fragment thereof, a buffering agent to maintain the pH of the pharmaceutical composition within the range of about pH 5.0 to about pH 7.0; an amount of arginine-HCl to render the liquid pharmaceutical composition near isotonic; and further comprises a surfactant. In other embodiments, the liquid pharmaceutical composition comprises an antagonist anti-CD40 antibody, for example, the monoclonal antibody CHIR-12.12 or CHIR-5.9, or antigen-binding fragment thereof, a buffering agent to maintain the pH of the pharmaceutical composition within the range of about pH 5.0 to about pH 7.0; arginine-HCl at a concentration of about 50 mM to about 300 mM, or about 100 mM to about 200 mM; and further comprises a surfactant.

Typical surfactants employed are nonionic surfactants, including polyoxyethylene sorbitol esters such as polysorbate 80 (Tween® 80) and polysorbate 20 (Tween® 20); polyoxypropylene-polyoxyethylene esters such as Pluronic® F68; polyoxyethylene alcohols such as Brij® 35; simethicone; polyethylene glycol such as PEG400; lysophosphatidylcholine; and polyoxyethylene-p-t-octylphenol such as Triton™ X-100. Classic stabilization of pharmaceuticals by surfactants or emulsifiers is described, for example, in Levine et al. (1991) *J. Parenteral Sci. Technol.* 45(3):160-165, herein incorporated by reference. A preferred surfactant employed in the practice of the present invention is polysorbate 20 or polysorbate 80. Where a surfactant is included, it is typically added in an amount from about 0.001% to about 1.0%, about 0.001% to about 0.5%, about 0.001% to about 0.4%, about 0.001% to about 0.3%, about 0.001% to about 0.2%, about 0.005% to about 0.5%, about 0.005% to about 0.2%, about 0.01% to about 0.5%, about 0.01% to about 0.2%, about 0.03% to about 0.5%, about 0.03% to about 0.3%, about 0.05% to about 0.5%, or about 0.05% to about 0.2%, where percentages are on a weight/volume (w/v) basis.

Thus, in some embodiments, the liquid pharmaceutical composition comprises an antagonist anti-CD40 antibody, for example, the monoclonal antibody CHIR-12.12 or CHIR-5.9, or antigen-binding fragment thereof, the buffering agent is a citrate/citric acid buffer, for example, sodium citrate/citric acid buffer, at a concentration of about 1 mM to about 50 mM, about 5 mM to about 25 mM, or about 5 mM to about 15 mM; the composition has a pH of about pH 5.0 to about pH 7.0, about pH 5.0 to about pH 6.5, or about pH 5.5 to about pH 6.0; arginine-HCl is present at a concentration of about 50 mM to about 300 mM, about 100 mM to about 200 mM, or about 50 mM to about 150 mM; and the pharmaceutical composition further comprises a surfactant, for example, polysorbate 20, in an amount from about 0.001% to about 1.0% (w/v) or about 0.001% to about 0.5% (w/v). In other embodiments, the liquid pharmaceutical composition comprises an antagonist anti-CD40 antibody, for example, the monoclonal antibody CHIR-12.12 or CHIR-5.9, or antigen-binding fragment thereof, at a concentration of about 0.1 mg/ml to about 50.0 mg/ml, about 5.0 mg/ml to about 35.0 mg/ml, or about 10.0 mg/ml to about 35.0 mg/ml, including about 10.0 mg/ml, about 15.0 mg/ml, about 20.0 mg/ml, about 25.0 mg/ml, about 30.0 mg/ml, or about 35.0 mg/ml; about 50 mM to about 200 mM arginine-HCl, including about 150 mM arginine-HCl; the buffering agent is sodium citrate/citric acid buffer at a concentration of about 5 mM to about 20 mM, including about 10 mM; and the pharmaceutical composition optionally comprises a surfactant, for example, polysorbate 20, in an amount from about 0.001% to about 1.0% (w/v), including about 0.001% to about 0.5% (w/v), about 0.01% to about 0.25% (w/v), about 0.025% to about 0.2% (w/v), about 0.025% to about 0.1% (w/v), or about 0.05% to about 0.2% (w/v); where the liquid pharmaceutical composition has a pH of about pH 5.0 to about pH 7.0, about pH 5.0 to about pH 6.0, about pH 5.0 to about pH 5.5, about pH 5.5 to about pH 6.5, about pH 5.5 to about pH 6.0, or about pH 5.5.

The liquid pharmaceutical composition can be essentially free of any preservatives and other carriers, excipients, or stabilizers. Alternatively, the pharmaceutical composition can optionally include one or more preservatives, for example, antibacterial agents, pharmaceutically acceptable carriers, excipients, or stabilizers described elsewhere herein provided they do not adversely affect the physicochemical stability of the anti-CD40 antibody or antigen-binding fragment thereof. Examples of acceptable carriers, excipients, and stabilizers include, but are not limited to, additional buffering agents, co-solvents, surfactants, antioxidants including ascorbic acid and methionine, chelating agents such as EDTA, metal complexes (for example, Zn-protein complexes), and biodegradable polymers such as polyesters. A thorough discussion of formulation and selection of pharmaceutically acceptable carriers, stabilizers, and isomolytes can be found in *Remington's Pharmaceutical Sciences* (18th ed.; Mack Publishing Company, Eaton, Pa., 1990), herein incorporated by reference.

Thus, in one embodiment, the antagonist anti-CD40 antibody-containing liquid pharmaceutical compositions of the invention further comprise the amino acid methionine to inhibit oxidation of oxidizable amino acid residues within the antibody polypeptide chains. By "inhibit" is intended minimal accumulation of oxidized species over time. Inhibiting oxidation results in greater retention of the antagonist anti-CD40 antibody in its proper molecular form. Any stereoisomer of methionine (L, D, or DL isomer) or combinations thereof can be used. The amount to be added should be an amount sufficient to inhibit oxidation of the oxidizable amino acid residues such that the amount of oxidized species is acceptable to regulatory agencies. Typically, this means that the composition contains no more than about 10% to about 30% oxidation products. Generally, this can be achieved by adding methionine such that the ratio of methionine added to methionine residues ranges from about 1:1 to about 1000:1, most preferably 10:1 to about 100:1.

The preferred amount of methionine to be added can readily be determined empirically by preparing the composition comprising the antagonist anti-CD40 antibody of interest, or antigen-binding fragment thereof, with different concentrations of methionine and determining the relative effect on formation of oxidative species of the polypeptide using, for instance, chromatographic separation of the molecular species and identification using polypeptide molecular weight standards, such as with RP-HPLC, or hydrophobic interaction chromatography (HIC) as described below in Example 1. That concentration of methionine that maximizes inhibition of oxidation of oxidizable amino acid residues, without having adverse affects on amino acid-related inhibition of antibody aggregation, would represent a preferred amount of methionine to be added to the composition to further improve antibody stability.

Thus, in some embodiments of the invention, the liquid pharmaceutical composition comprises an antagonist anti-CD40 antibody, for example, the monoclonal antibody CHIR-12.12 or CHIR-5.9, or antigen-binding fragment thereof; the buffering agent is a citrate/citric acid buffer, for example, sodium citrate/citric acid buffer, at a concentration of about 1 mM to about 50 mM, about 5 mM to about 25 mM, or about 5 mM to about 15 mM; the pharmaceutical composition has a pH of about pH 5.0 to about pH 7.0, about pH 5.0 to about pH 6.5, or about pH 5.5 to about pH 6.0; arginine-HCl is present at a concentration of about 50 mM to about 300 mM, about 100 mM to about 200 mM, or about 50 mM to about 150 mM; a surfactant is present, for example, polysorbate 20 or polysorbate 80, in an amount from about 0.001% to about 1.0% (w/v) or about 0.001% to about 0.5% (w/v); and the pharmaceutical composition further comprises methionine at a concentration of about 0.5 mM to about 20.0 mM, about 0.5 mM to about 10.0 mM, about 1.0 mM to about 20.0 mM, about 1.0 mM to about 10.0 mM, about 1.0 mM to about 7.0 mM, about 2.0 mM to about 6.0 mM, or about 2.5 mM to about 5.0 mM. In other embodiments, the liquid pharmaceutical composition comprises an antagonist anti-CD40 antibody, for example, the monoclonal antibody CHIR-12.12 or CHIR-5.9, or antigen-binding fragment thereof, at a concentration of about 0.1 mg/ml to about 50.0 mg/ml, about 5.0 mg/ml to about 35.0 mg/ml, or about 10.0 mg/ml to about 35.0 mg/ml, including about 10.0 mg/ml, about 15.0 mg/ml, about 20.0 mg/ml, about 25.0 mg/ml, about 30.0 mg/ml, or about 35.0 mg/ml; about 50 mM to about 200 mM arginine-HCl, including about 150 mM arginine-HCl; sodium citrate/citric acid buffer at a concentration of about 5 mM to about 20 mM, including about 10 mM; optionally a surfactant, for example, polysorbate 20, in an amount from about 0.001% to about 1.0% (w/v), including about 0.001% to about 0.5% (w/v), about 0.01% to about 0.25% (w/v), about 0.025% to about 0.2% (w/v), about 0.025% to about 0.1% (w/v), or about 0.05% to about 0.2% (w/v); and optionally methionine, for example, at a concentration of about 0.5 mM to about 10.0 mM, about 1.0 mM to about 7.0 mM, about 2.0 mM to about 6.0 mM, or about 2.5 mM to about 5.0 mM, including about 2.0 mM, about 2.5 mM, about 3.0 mM, about 3.5 mM, about 4.0 mM, about 4.5 mM, about 5.0 mM, or about 5.5 mM; where the liquid pharmaceutical composition has a pH of about pH 5.0 to about pH 7.0, about pH 5.0 to about pH 6.0, about pH 5.0 to about pH 5.5, about pH 5.5 to about pH 6.5, about pH 5.5 to about pH 6.0, or about pH 5.5.

In yet other embodiments, the liquid pharmaceutical composition comprises the monoclonal antibody CHIR-12.12 or CHIR-5.9, or antigen-binding fragment thereof, at a concentration of about 0.1 mg/ml to about 50.0 mg/ml, about 5.0 mg/ml to about 35.0 mg/ml, or about 10.0 mg/ml to about 35.0 mg/ml, including about 10.0 mg/ml, about 15.0 mg/ml, about 20.0 mg/ml, about 25.0 mg/ml, about 30.0 mg/ml, or about 35.0 mg/ml; about 100 mM to about 200 mM arginine-HCl, including about 150 mM arginine-HCl; sodium citrate/citric acid buffer at a concentration of about 5 mM to about 20 mM, including about 10 mM; optionally a surfactant, for example, polysorbate 20, in an amount from about 0.025% to about 0.1% (w/v); and optionally methionine, for example, at a concentration of about 2.0 mM to about 5.5 mM, including about 5.0 mM; where the liquid pharmaceutical composition has a pH of about pH 5.0 to about pH 6.0, including about pH 5.5.

In addition to those agents disclosed above, other stabilizing agents, such as albumin, ethylenediaminetetraacetic acid (EDTA) or one of its salts such as disodium EDTA, can optionally be added to further enhance the stability of the liquid pharmaceutical compositions. Where desirable, the amount of albumin can be added at concentrations of about 1.0% w/v or less. The EDTA acts as a scavenger of metal ions known to catalyze many oxidation reactions, thus providing an additional stabilizing agent. Where desirable, the amount of EDTA can be added at concentrations of about 0.1 to about 5.0 mM.

Where desirable, sugars or sugar alcohols may also be included in the stabilized liquid antagonist anti-CD40 antibody-containing pharmaceutical compositions of the present invention. Any sugar such as mono-, di-, or polysaccharides, or water-soluble glucans, including for example fructose, glucose, mannose, sorbose, xylose, maltose, lactose, sucrose, dextran, pullulan, dextrin, cyclodextrin, soluble starch, hydroxyethyl starch and carboxymethylcellulose-Na may be used. Sucrose is the most preferred sugar additive. Sugar alcohol is defined as a C4-C8 hydrocarbon having an —OH group and includes, for example, mannitol, sorbitol, inositol, galactitol, dulcitol, xylitol, and arabitol with mannitol being the most preferred sugar alcohol additive. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. Preferably, the sugar or sugar alcohol concentration is between about 1.0% and about 15.0% (w/v), more preferably between about 2.0% and about 10.0% (w/v).

After the liquid pharmaceutical composition described herein is prepared, it can be lyophilized to prevent degradation. Methods for lyophilizing liquid compositions are known to those of ordinary skill in the art. Just prior to use, the composition may be reconstituted with a sterile diluent (Ringer's solution, distilled water, or sterile saline, for example) that may include additional ingredients. Upon reconstitution, the composition is preferably administered to subjects using those methods that are known to those skilled in the art.

The liquid antagonist anti-CD40 antibody-containing pharmaceutical compositions of the invention are stable and thus have increased storage stability relative to antagonist anti-CD40 antibody compositions prepared in buffered solutions comprising sodium chloride as the isotonizing agent. Without being bound by theory, it is believed that this increased storage stability is observed in the liquid formulation, whether stored directly in that form for later use, stored in a frozen state and thawed prior to use, or prepared in a dried form, such as a lyophilized, air-dried, or spray-dried form, for later reconstitution into a liquid form or other form prior to use. Preferably, compositions of the invention are stored directly in their liquid form to take full advantage of the convenience of having increased storage stability in the liquid form, ease of administration without reconstitution, and ability to supply the formulation in prefilled, ready-to-use syringes or as multidose preparations if the formulation is compatible with bacteriostatic agents.

The compositions of the invention relate to the discovery that the use of arginine-HCl as an isotonizing agent and a mixture of an acid and its salt form, such as sodium citrate/citric acid, as the buffering agent results in a liquid antagonist anti-CD40 antibody-containing pharmaceutical composition that has increased storage stability relative to a liquid antagonist anti-CD40 antibody-containing pharmaceutical composition prepared with sodium chloride and the respective buffering agent. The increased storage stability of the composition is achieved through the influence of the acidic form of arginine on stability of the therapeutically active antagonist anti-C40 antibody, more particularly its influence on polypeptide aggregation, fragmentation, and deamidation during storage in liquid formulations. Furthermore, incorporation of arginine-HCl as an isotonizing agent in a liquid antagonist anti-CD40 antibody composition buffered in the manner set forth herein results in liquid pharmaceutical compositions that are near isotonic without having to include additional isotonizing agents, such as sodium chloride.

The acidic form of arginine incorporated into the stable liquid pharmaceutical compositions of the invention protects the therapeutically active antagonist anti-CD40 antibody or antigen-binding fragment thereof against physical and chemical changes, thereby increasing stability of the antibody during storage of the composition. By "increasing stability" is intended that one or more of aggregate formation, fragmentation, and deamidation by the antibody during storage of the liquid pharmaceutical composition is decreased relative to that observed during storage of a liquid pharmaceutical composition comprising the antagonist anti-CD40 antibody and the same formulation components with the exception of the absence of this particular isotonizing and stabilizing agent. The effect of arginine-HCl on antagonist anti-CD40 antibody aggregation during storage in a liquid composition can be readily determined by measuring the change in soluble anti-CD40 antibody in solution over time. Amount of soluble anti-CD40 antibody in solution can be quantified by a number of analytical assays adapted to detection of the antibody of interest. Such assays include, for example, reverse phase (RP)-HPLC, size exclusion (SEC)-HPLC, and UV absorbance. Aggregation can also be monitored using SDS-PAGE. See also the Examples herein below.

In the case of aggregation, an effective amount of arginine-HCl to incorporate within an antagonist anti-CD40 antibody-containing liquid pharmaceutical composition to obtain the stable pharmaceutical compositions of the invention would be viewed as an amount that resulted in decreased aggregate formation over time, and hence greater retention of soluble antagonist anti-CD40 antibody in solution in its nonaggregated, biologically active molecular form. Thus, for example, where the antagonist anti-CD40 antibody is the CHIR-12.12 monoclonal anti-CD40 antibody described in the Examples below, an effective amount of arginine-HCl for use in preparing a stable composition of the invention would be an amount that resulted in greater retention of the CHIR-12.12 antibody in its monomeric molecular form.

Without being bound by theory, increased storage stability of the stable liquid antagonist anti-CD40 antibody-containing compositions of the invention may also be associated with the inhibitory effects of arginine-HCl on antibody fragmentation and/or deamidation of glutamine and/or asparagine residues within the therapeutically active antibody during storage. The effect of arginine-HCl on antibody fragmentation can readily be determined by monitoring changes in molecular species within the formulation over time, for example, using SDS-PAGE and/or SEC-HPLC analysis; see the Examples herein below. The effect of arginine-HCl on deamidation of the anti-CD40 antibody polypeptide during storage in a liquid composition can readily be determined by monitoring the amount of antagonist anti-CD40 antibody present in its deamidated form over time. Methods for measuring molecular species, i.e., native or deamidated, of a polypeptide present in solution phase are generally known in the art. Such methods include chromatographic separation of the molecular species and identification using polypeptide molecular weight standards, such as with RP-HPLC, or cation exchange chromatography (CIEX-HPLC) as described in the Examples below.

The stable liquid antagonist anti-CD40 antibody-containing pharmaceutical compositions of the invention may contain other compounds that increase the effectiveness or promote the desirable qualities of the antagonist anti-CD40 antibody of interest that serves as a therapeutically active component so long as the primary stabilizing effect achieved with the arginine-HCl is not adversely affected. The composition must be safe for administration via the route that is chosen, it must be sterile, and must retain its desired therapeutic activity.

The pharmaceutical compositions of the present invention can be prepared, for example, by premixing the stabilizing and buffering agents, and any other excipients, prior to incorporation of the antagonist anti-CD40 antibody of interest. Any additional excipients that may be added to further stabilize the compositions of the present invention must not adversely affect the stabilizing effects of the primary isotonizing and stabilizing agent, i.e., the arginine-HCl, further in combination with the buffering agent, as used to obtain the novel compositions disclosed herein. Following addition of the arginine-HCl to achieve near isotonicity and increased stability of the antagonist anti-CD40 antibody of interest, pH of the liquid composition is adjusted using the buffering agent, preferably within a range disclosed herein, more preferably to the pH optimum for the antagonist anti-CD40 antibody of interest, for example, a pH between about pH 5.0 and pH 7.0, preferably about pH 5.5, for the monoclonal antibody CHIR-12.12. Although pH can be adjusted following addition of the antagonist anti-CD40 antibody into the composition, preferably it is adjusted prior to addition of this polypeptide, as this can reduce the risk of denaturation the polypeptide. Appropriate mechanical devices are then used for achieving a proper mix of constituents.

Thus, the present invention provides a method for increasing the stability of an antagonist anti-CD40 antibody, or antigen-binding fragment thereof, in a liquid pharmaceutical composition. The method comprises combining the antagonist anti-CD40 antibody or antigen-binding fragment thereof with a buffering agent that maintains the pharmaceutical composition at a pH between about pH 5.0 and pH 7.0, and an amount of arginine-HCl sufficient to render the composition near isotonic. In some embodiments, the buffering agent is a citrate/citric acid buffer, the concentration of the buffering agent is about 5 mM to about 50 mM, and the amount of arginine-HCl provides for a concentration of this isotonizing agent within the composition of between about 50 mM to about 300 mM arginine-HCl. In other embodiments, the antagonist anti-CD40 antibody is the CHIR-12.12 or CHIR-5.9 antibody, or antigen-binding fragment thereof, the buffering agent is about 5 mM to about 25 mM sodium citrate/citric acid buffer; the concentration of arginine-HCl within the composition is about 150 mM, and the composition has a pH of about 5.0, about 5.5, about 6.0, or about 6.5.

The stabilized liquid pharmaceutical composition comprising the antagonist anti-CD40 antibody of interest, for example, an antagonist anti-CD40 antibody such as the CHIR-12.12 or CHIR-5.9 monoclonal antibody, or antigen-binding fragment thereof should be formulated in a unit dosage and may be in an injectable or infusible form such as solution, suspension, or emulsion. As previously noted, it can be stored frozen or prepared in the dried form, such as a lyophilized powder, which can be reconstituted into the liquid solution, suspension, or emulsion before administration by any of various methods including oral or parenteral routes of administration. Preferably it is stored in the liquid formulation to take advantage of the increased storage stability achieved in accordance with the methods of the present invention as outlined below. The stabilized pharmaceutical composition is preferably sterilized by membrane filtration and is stored in unit-dose or multi-dose containers such as sealed vials or ampules. Additional methods for formulating a pharmaceutical composition generally known in the art may be used to further enhance storage stability of the liquid pharmaceutical compositions disclosed herein provided they do not adversely affect the beneficial effects of the preferred stabilizing and buffering agents disclosed described herein above. A thorough discussion of formulation and selection of pharmaceutically acceptable carriers, stabilizers, etc. can be found in *Remington's Pharmaceutical Sciences* (1990) (18$^{th}$ ed., Mack Pub. Co., Eaton, Pa.), herein incorporated by reference.

In this manner, the present invention provides an article of manufacture comprising a container holding a stable liquid antagonist anti-CD40 antibody-containing pharmaceutical composition of the invention, and optionally comprising instructions for its use. Suitable containers include, for example, vials, bottles, and syringes. The container may be formed from a variety of materials, such as plastic or glass. In one embodiment, the container is a 3-50 cc single-use glass vial. Alternatively, for a ready-to-use formulation, the container may be, for example, a 3-100 cc glass vial. The container holds the formulation and the label on, or associated with, the container may indicate directions for use. The article of manufacture may further include other materials desirable from a commercial and user standpoint, including other buffers, diluents, filters, needles, syringes, and package inserts with instructions for use.

Anti-CD40 Antibodies in the Pharmaceutical Compositions of the Invention

The pharmaceutical compositions of the present invention comprise anti-CD40 antibodies, particularly antagonist anti-CD40 antibodies or antigen-binding fragments thereof that target the CD40 receptor and which modulate ADCC, interfere with CD40 signaling, particularly CD40 signaling pathways that are mediated by interaction of CD40 with the CD40 ligand (CD40L), or both. By "CD40 antigen," "CD40 cell surface antigen," "CD40 receptor," or "CD40" is intended a transmembrane glycoprotein that belongs to the tumor necrosis factor (TNF) receptor family (see, for example, U.S. Pat. Nos. 5,674,492 and 4,708,871; Stamenkovic et al. (1989) *EMBO* 8:1403; Clark (1990) *Tissue Antigens* 36:33; Barclay et al. (1997) *The Leucocyte Antigen Facts Book* (2d ed.; Academic Press, San Diego)). Two isoforms of human CD40, encoded by alternatively spliced transcript variants of this gene, have been identified. The first isoform (also known as the "long isoform" or "isoform 1") is expressed as a 277-amino-acid precursor polypeptide (SEQ ID NO: 12 (first reported as GenBank Accession No. CAA43045, and identified as isoform 1 in GenBank Accession No. NP_001241), encoded by SEQ ID NO: 11 (see GenBank Accession Nos. X60592 and NM_001250)), which has a signal sequence represented by the first 19 residues. The second isoform (also known as the "short isoform" or "isoform 2") is expressed as a 203-amino-acid precursor polypeptide (SEQ ID NO: 10 (GenBank Accession No. NP_690593), encoded by SEQ ID NO:9 (GenBank Accession No. NM_152854)), which also has a signal sequence represented by the first 19 residues. The precursor polypeptides of these two isoforms of human CD40 share in common their first 165 residues (i.e., residues 1-165 of SEQ ID NO: 10 and SEQ ID NO: 12). The precursor polypeptide of the short isoform (shown in SEQ ID NO: 10) is encoded by a transcript variant (SEQ ID NO:9) that lacks a coding segment, which leads to a translation frame shift; the resulting CD40 isoform contains a shorter and distinct C-terminus (residues 166-203 of SEQ ID NO: 10) from that contained in the long isoform of CD40 (C-terminus shown in residues 166-277 of SEQ ID NO: 12). For purposes of the present invention, the term "CD40 antigen," "CD40 cell surface antigen," "CD40 receptor," or "CD40" encompasses both the short and long isoforms of CD40.

The CD40 antigen is displayed on the surface of a variety of cell types, as described elsewhere herein. By "displayed on the surface" and "expressed on the surface" is intended that all or a portion of the CD40 antigen is exposed to the exterior of the cell. The displayed or expressed CD40 antigen may be fully or partially glycosylated.

By "agonist activity" is intended that a substance functions as an agonist. An agonist combines with a receptor on a cell and initiates a reaction or activity that is similar to or the same as that initiated by the receptor's natural ligand. An agonist of CD40 induces any or all of, but not limited to, the following responses: B cell proliferation and differentiation, antibody production, intercellular adhesion, B cell memory generation, isotype switching, up-regulation of cell-surface expression of MHC Class II and CD80/86, and secretion of pro-inflammatory cytokines such as IL-8, IL-12, and TNF. By "antagonist activity" is intended that the substance functions as an antagonist. An antagonist of CD40 prevents or reduces induction of any of the responses induced by binding of the CD40 receptor to an agonist ligand, particularly CD40L. The antagonist may reduce induction of any one or more of the responses to agonist binding by 5%, 10%, 15%, 20%, 25%, 30%, 35%, preferably 40%, 45%, 50%, 55%, 60%, more preferably 70%, 80%, 85%, and most preferably 90%, 95%, 99%, or 100%. Methods for measuring CD40 ligand binding specificity and antagonist activity of an anti-CD40 therapeutic agent, for example, an anti-CD40 antibody, are known in the art and include, but are not limited to, standard competitive binding assays, assays for monitoring immunoglobulin secretion by B cells, B cell proliferation assays, Banchereau-Like-B cell proliferation assays, T cell helper assays for antibody production, co-stimulation of B cell proliferation assays, and assays for up-regulation of B cell activation markers. See, for example, such assays disclosed in WO 00/75348 and U.S. Pat. No. 6,087,329, herein incorporated by reference. Also see, provisional applications entitled "Antagonist Anti-CD40 Monoclonal Antibodies and Methods for Their Use," filed Nov. 4, 2003, Nov. 26, 2003, and Apr. 27, 2004, and assigned U.S. Patent Application Nos. 60/517,337, 60/525,579, and 60/565,710, respectively, and International Patent Application No. PCT/US2004/037152, also entitled "Antagonist Anti-CD40 Monoclonal Antibodies and Methods for Their Use," filed Nov. 4, 2004, and published as WO 2005/044854); the contents of each of which are herein incorporated by reference in their entirety.

By "significant" agonist activity is intended an agonist activity of at least 30%, 35%, 40%, 45%, 50%, 60%, 70%, 75%, 80%, 85%, 90%, 95%, or 100% greater than the agonist activity induced by a neutral substance or negative control as measured in an assay of a B cell response. Preferably, "significant" agonist activity is an agonist activity that is at least 2-fold greater or at least 3-fold greater than the agonist activity induced by a neutral substance or negative control as measured in an assay of a B cell response. Thus, for example, where the B cell response of interest is B cell proliferation, "significant" agonist activity would be induction of a level of B cell proliferation that is at least 2-fold greater or at least 3-fold greater than the level of B cell proliferation induced by a neutral substance or negative control. In one embodiment, a non-specific immunoglobulin, for example IgG1, that does not bind to CD40 serves as the negative control. A substance "free of significant agonist activity" would exhibit an agonist activity of not more than about 25% greater than the agonist activity induced by a neutral substance or negative control, preferably not more than about 20% greater, 15% greater, 10% greater, 5% greater, 1% greater, 0.5% greater, or even not more than about 0.1% greater than the agonist activity induced by a neutral substance or negative control as measured in an assay of a B cell response.

In some embodiments of the invention, the stable liquid pharmaceutical compositions of the invention comprise an antagonist anti-CD40 antibody. Such antibodies are free of significant agonist activity as noted above when bound to a CD40 antigen on a human cell. In one embodiment of the invention, the antagonist anti-CD40 antibody is free of significant agonist activity in one cellular response. In another embodiment of the invention, the antagonist anti-CD40 antibody is free of significant agonist activity in assays of more than one cellular response (e.g., proliferation and differentiation, or proliferation, differentiation, and, for B cells, antibody production). In some embodiments of the invention, the antagonist anti-CD40 antibody is, for example, the fully human monoclonal antibody CHIR-12.12 or CHIR-5.9, or antigen-binding fragment thereof, as noted herein below.

Any of the assays known in the art can be used to determine whether an anti-CD40 antibody acts as an antagonist of one or more B cell responses. In some embodiments, the anti-CD40 antibody acts as an antagonist of at least one B cell response selected from the group consisting of B cell proliferation, B cell differentiation, antibody production, intercellular adhesion, B cell memory generation, isotype switching, up-regulation of cell-surface expression of MHC Class II and CD80/86, and secretion of pro-inflammatory cytokines such as IL-8, IL-12, and TNF. Of particular interest are antagonist anti-CD40 antibodies that free of significant agonist activity with respect to B cell proliferation when bound to the human CD40 antigen on the surface of a human B cell.

In one such embodiment, the anti-CD40 antibody is an antagonist of B cell proliferation as measured in a B cell proliferation assay such as that described in Example 4 herein below, and the antagonist anti-CD40 antibody stimulates B cell proliferation at a level that is not more than about 25% greater than the B cell proliferation induced by a neutral substance or negative control, preferably not more than about 20% greater, 15% greater, 10% greater, 5% greater, 1% greater, 0.5% greater, or even not more than about 0.1% greater than the B cell proliferation induced by a neutral substance or negative control.

In other embodiments, the anti-CD40 antibody is an antagonist of B cell proliferation that is induced by another anti-CD40 antibody, for example, the S2C6 anti-CD40 antibody, as measured in a B cell proliferation assay such as that described in Example 4 herein below, and the level of B cell proliferation stimulated by the other anti-CD40 antibody in the presence of the antagonist anti-CD40 antibody is not more than about 25% of the B cell proliferation induced by the other anti-CD40 antibody in the absence of the antagonist anti-CD40 antibody (i.e., at least 75% inhibition), preferably not more than about 20%, 15%, 10%, 5%, 1%, 0.5%, or even not more than about 0.1% of the B cell proliferation induced by the other anti-CD40 antibody in the absence of the antagonist anti-CD40 antibody.

In yet other embodiments, the anti-CD40 antibody is an antagonist of B cell proliferation that is induced by the cell line EL4B5 as measured in the B cell activation assay described in Example 4 herein below, and the level of B cell proliferation stimulated by the EL4B5 cell line in the presence of the antagonist anti-CD40 antibody is not more than about 25% of the B cell proliferation induced by this cell line in the absence of the antagonist anti-CD40 antibody (i.e., at least 75% inhibition), preferably not more than about 20%, 15%, 10%, 5%, 1%, 0.5%, or even not more than about 0.1% of the B cell proliferation induced by this cell line in the absence of the antagonist anti-CD40 antibody.

In still other embodiments, the anti-CD40 antibody is an antagonist of human T-cell-induced antibody production by human B cells as measured in the human T-cell helper assay for antibody production by B cells described in Example 4 herein below. In this manner, the level of IgG antibody production, IgM antibody production, or both IgG and IgM antibody production by B cells stimulated by T cells in the presence of the antagonist anti-CD40 antibody is not more than about 50% of the respective antibody production by B cells stimulated by T cells in the absence of the antagonist anti-CD40 antibody (i.e., at least 75% inhibition), preferably not more than about 25%, 20%, 15%, 10%, 5%, 1%, 0.5%, or even not more than about 0.1% of the respective antibody production by B cells stimulated by T cells in the absence of the antagonist anti-CD40 antibody.

By "CD40 ligand" is intended any peptide, polypeptide, or protein that can bind to and activate one or more CD40 signaling pathways. Thus, "CD40 ligands" include, but are not limited to, full-length CD40 ligand proteins and variants and fragments thereof that retain sufficient activity to carry out the function of binding to and stimulating CD40 signaling on CD40-expressing cells. Modifications to a native CD40 ligand, for example, human CD40 ligand (CD40L; also known as CD154), include, but are not limited to, substitutions, deletions, truncations, extensions, fusion proteins, fragments, peptidomimetics, and the like. In some embodiments of the invention, an assay for assessing biological activity of an antagonist anti-CD40 antibody includes the use of soluble CD40L, for example, soluble recombinant human CD40L (Alexis Corporation, Bingham, Nottinghamshire, UK) to stimulate CD40 signaling on CD40-expressing cells.

By "CD40L-mediated CD40 signaling" is intended any of the biological activities that result from interaction of the cell-surface receptor CD40 with a CD40 ligand. Examples of CD40 signaling are signals that lead to proliferation and survival of CD40-expressing cells, and stimulation of one or more CD40-signaling pathways within CD40-expressing cells. A CD40 "signaling pathway" or "signal transduction pathway" is intended to mean at least one biochemical reaction, or a group of biochemical reactions, that results from interaction of the CD40 receptor with a CD40 ligand, for example, CD40L, and which generates a signal that, when transmitted through the signal pathway, leads to activation of one or more downstream molecules in the signaling cascade. Signal transduction pathways involve a number of signal transduction molecules that lead to transmission of a signal from the cell-surface CD40 receptor across the plasma membrane of a cell, and through one or more in a series of signal transduction molecules, through the cytoplasm of the cell, and in some instances, into the cell's nucleus. CD40 signal transduction pathways include, for example, the AKT signaling pathway, which leads to activation of AKT, and ultimately activation of NF-κB via the NF-κB signaling pathway; and mitogen-activated protein kinase (MAPK) signaling pathways, including the MEK/ERK signaling pathway and the MEK/p38 signaling pathway, which lead to activation of ERK and p38, respectively. The balance between activation and blocking of these signaling pathways favors either cell survival or apoptosis.

In some embodiments, the stable pharmaceutical compositions of the invention comprise antagonist anti-CD40 antibodies that block CD40L-mediated CD40 signaling. For a more detailed description of the role of antagonist anti-CD40 antibodies in blocking CD40L-mediated CD40 signaling, see, for example, provisional applications entitled "Antagonist Anti-CD40 Monoclonal Antibodies and Methods for Their Use," filed Nov. 4, 2003, Nov. 26, 2003, and Apr. 27, 2004, and assigned U.S. Patent Application Nos. 60/517,337, 60/525,579, and 60/565,710, respectively, and International Patent Application No. PCT/US2004/037152, also entitled "Antagonist Anti-CD40 Monoclonal Antibodies and Methods for Their Use," filed Nov. 4, 2004, and published as WO 2005/044854; the contents of each of which are herein incorporated by reference in their entirety. See also provisional application entitled "Methods for Diagnosis and Treatment of Proliferative Disorders Mediated by CD40 Signaling," filed Dec. 9, 2005, and assigned U.S. Patent Application No. 60/749,285, and corresponding International Patent Application No. PCT/US2006/019414, filed May 18, 2006, and published as WO 2006/125143; and provisional application entitled "Methods for Diagnosis and Treatment of Diseases Having an Autoimmune and/or Inflammatory Component," filed Dec. 9, 2005, and assigned U.S. Patent Application No. 60/749,336, and corresponding International Patent Application PCT/US2006/019325, filed May 18, 2006, and published as WO 2006/125117; the contents of each of which are herein incorporated by reference in their entirety.

The stable liquid pharmaceutical compositions of the present invention comprise anti-CD40 antibodies, particularly antagonist anti-CD40 antibodies and/or antigen-binding fragments thereof. The following terms and definitions apply to such antibodies.

"Antibodies" and "immunoglobulins" (Igs) are glycoproteins having the same structural characteristics. The terms are used synonymously. In some instances the antigen specificity of the immunoglobulin may be known.

The term "antibody" is used in the broadest sense and covers fully assembled antibodies, antibody fragments that can bind antigen (e.g., Fab, F(ab')$_2$, Fv, single chain antibodies, diabodies, antibody chimeras, hybrid antibodies, bispecific antibodies, humanized antibodies, and the like), and recombinant peptides comprising the forgoing.

The terms "monoclonal antibody" and "mAb" as used herein refer to an antibody obtained from a substantially homogeneous population of antibodies, i.e., the individual antibodies comprising the population are identical except for possible naturally occurring mutations that may be present in minor amounts.

"Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy-chain variable domains.

The term "variable" refers to the fact that certain portions of the variable domains differ extensively in sequence among antibodies. Variable regions confer antigen-binding specificity. However, the variability is not evenly distributed throughout the variable domains of antibodies. It is concentrated in three segments called complementarity determining regions (CDRs) or hypervariable regions, both in the light chain and the heavy-chain variable domains. The more highly conserved portions of variable domains are celled in the framework (FR) regions. The variable domains of native heavy and light chains each comprise four FR regions, largely adopting a β-pleated-sheet configuration, connected by three CDRs, which form loops connecting, and in some cases forming part of, the β-pleated-sheet structure. The CDRs in each chain are held together in close proximity by the FR regions and, with the CDRs from the other chain, contribute to the formation of the antigen-binding site of antibodies (see, Kabat et al. (1991) *NIH Publ No.* 91-3242, Vol. I, pages 647-669). The constant domains are not involved directly in binding an antibody to an antigen, but exhibit various effector functions, such as Fc receptor (FcR) binding, participation of the antibody in antibody-dependent cellular toxicity, initiation of complement dependent cytotoxicity, and mast cell degranulation.

The term "hypervariable region," when used herein, refers to the amino acid residues of an antibody that are responsible for antigen-binding. The hypervariable region comprises amino acid residues from a "complementarily determining region" or "CDR" (i.e., residues 24-34 (L1), 50-56 (L2), and 89-97 (L3) in the light-chain variable domain and 31-35 (H1), 50-65 (H2), and 95-102 (H3) in the heavy-chain variable domain; Kabat et al. (1991) *Sequences of Proteins of Immunological Interest*, 5th Ed. Public Health Service, National Institute of Health, Bethesda, Md.) and/or those residues from a "hypervariable loop" (i.e., residues 26-32 (L1), 50-52 (L2), and 91-96 (L3) in the light-chain variable domain and (H1), 53-55 (H2), and 96-101 (H3) in the heavy chain variable domain; Clothia and Lesk, (1987) *J. Mol. Biol.*, 196:901-917). "Framework" or "FR" residues are those variable domain residues other than the hypervariable region residues, as herein deemed.

"Antibody fragments" comprise a portion of an intact antibody, preferably the antigen-binding or variable region of the intact antibody. Examples of antibody fragments include Fab, Fab, F(ab')2, and Fv fragments; diabodies; linear antibodies (Zapata et al. (1995) *Protein Eng.* 10: 1057-1062); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment that contains a complete antigen recognition and binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain ($C_H1$) of the heavy chain. Fab fragments differ from Fab' fragments by the addition of a few residues at the carboxy terminus of the heavy chain $C_H1$ domain including one or more cysteines from the antibody hinge region. Fab'-SH is the designation herein for Fab' in which the cysteine residue(s) of the constant domains bear a free thiol group. Fab' fragments are produced by reducing the F(ab')2 fragment's heavy chain disulfide bridge. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of human immunoglobulins: IgA, IgD, IgE, IgG, and IgM, and several of these may be further divided into subclasses (isotypes), e.g., IgG1, IgG2, IgG3, IgG4, IgA1, and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known. Different isotypes have different effector functions. For example, human IgG1 and IgG3 isotypes have ADCC (antibody dependent cell-mediated cytotoxicity) activity.

The word "label" when used herein refers to a detectable compound or composition that is conjugated directly or indirectly to the antibody so as to generate a "labeled" antibody. The label may be detectable by itself (e.g., radioisotope labels or fluorescent labels) or, in the case of an enzymatic label, may catalyze chemical alteration of a substrate compound or composition that is detectable.

A "host cell," as used herein, refers to a microorganism or a eukaryotic cell or cell line cultured as a unicellular entity that can be, or has been, used as a recipient for a recombinant vector or other transfer polynucleotides, and include the progeny of the original cell that has been transfected. It is understood that the progeny of a single cell may not necessarily be completely identical in morphology or in genomic or total DNA complement as the original parent, due to natural, accidental, or deliberate mutation.

"Human effector cells" are leukocytes that express one or more FcRs and perform effector functions. Preferably, the cells express at least FcγRIII and carry out antigen-dependent cell-mediated cyotoxicity (ADCC) effector function. Examples of human leukocytes that mediate ADCC include peripheral blood mononuclear cells (PBMC), natural killer (NK) cells, monocytes, macrophages, eosinophils, and neutrophils, with PBMCs and NK cells being preferred. Antibodies that have ADCC activity are typically of the IgG1 or IgG3 isotype. Note that in addition to isolating IgG1 and IgG3 antibodies, such ADCC-mediating antibodies can be made by engineering a variable region from a non-ADCC antibody or variable region fragment to an IgG1 or IgG3 isotype constant region.

The terms "Fc receptor" or "FcR" are used to describe a receptor that binds to the Fc region of an antibody. The preferred FcR is a native-sequence human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see Daeron (1997) *Annu. Rev. Immunol.* 15:203-234). FcRs are reviewed in Ravetch and Kinet (1991) *Annu. Rev. Immunol.* 9:457-492 (1991); Capel et al. (1994) *Immunomethods* 4:25-34; and de Haas et al. (1995) *J. Lab. Clin. Med.* 126:330-341. Other FcRs, including those to be identified in the future, are encompassed by the term "FcR" herein. The term also includes the neonatal receptor, FcRn, which is responsible for the transfer of maternal IgGs to the fetus (Guyer et al. (1976) *J. Immunol.* 117:587 and Kim et al. (1994) *J. Immunol.* 24:249 (1994)).

There are a number of ways to make human antibodies. For example, secreting cells can be immortalized by infection with the Epstein-Barr virus (EBV). However, EBV-infected cells are difficult to clone and usually produce only relatively low yields of immunoglobulin (James and Bell (1987) *J. Immunol. Methods* 100:5-40). In the future, the immortalization of human B cells might possibly be achieved by introducing a defined combination of transforming genes. Such a possibility is highlighted by a recent demonstration that the expression of the telomerase catalytic subunit together with the SV40 large oncoprotein and an oncogenic allele of H-ras resulted in the tumorigenic conversion of normal human epithelial and fibroblast cells (Hahn et al. (1999) *Nature* 400:464-468). It is now possible to produce transgenic animals (e.g., mice) that are capable, upon immunization, of producing a repertoire of human antibodies in the absence of endogenous immunoglobulin production (Jakobovits et al. (1993) *Nature* 362:255-258; Lonberg and Huszar (1995) *Int. Rev. Immunol.* 13:65-93; Fishwild et al. (1996) *Nat. Biotechnol.* 14:845-851; Mendez et al. (1997) *Nat. Genet.* 15:146-156; Green (1999) *J. Immunol. Methods* 231:11-23; Tomizuka et al. (2000) *Proc. Natl. Acad. Sci. USA* 97:722-727; reviewed in Little et al. (2000) *Immunol. Today* 21:364-370). For example, it has been described that the homozygous deletion of the antibody heavy-chain joining region ($J_H$) gene in chimeric and germ-line mutant mice results in complete inhibition of endogenous antibody production (Jakobovits et al. (1993) *Proc. Natl. Acad. Sci. USA* 90:2551-2555). Transfer of the human germ-line immunoglobulin gene array in such germ-line mutant mice results in the production of human antibodies upon antigen challenge (Jakobovits et al. (1993) *Nature* 362:255-258). Mendez et al. (1997) (*Nature Genetics* 15:146-156) have generated a line of transgenic mice that, when challenged with an antigen, generates high affinity fully human antibodies. This was achieved by germ-line integration of megabase human heavy-chain and light-chain loci into mice with deletion into endogenous $J_H$ segment as described above. These mice (XenoMouse® II technology (Abgenix; Fremont, Calif.)) harbor 1,020 kb of human heavy-chain locus containing approximately 66 $V_H$ genes, complete $D_H$ and $J_H$ regions, and three different constant regions, and also harbors 800 kb of human κ locus containing 32 Vκ genes, Jκ segments, and Cκ genes. The antibodies produced in these mice closely resemble that seen in humans in all respects, including gene rearrangement, assembly, and repertoire. The human antibodies are preferentially expressed over endogenous antibodies due to deletion in endogenous segment that prevents gene rearrangement in the murine locus. Such mice may be immunized with an antigen of particular interest.

Sera from such immunized animals may be screened for antibody reactivity against the initial antigen. Lymphocytes may be isolated from lymph nodes or spleen cells and may further be selected for B cells by selecting for CD138-negative and CD 19-positive cells. In one aspect, such B cell cultures (BCCs) may be fused to myeloma cells to generate hybridomas as detailed above.

In another aspect, such B cell cultures may be screened further for reactivity against the initial antigen, preferably. Such screening includes enzyme-linked immunosorbent assay (ELISA) with the target/antigen protein, a competition assay with known antibodies that bind the antigen of interest, and in vitro binding to transiently transfected CHO or other cells that express the target antigen.

Monoclonal antibodies to CD40 are known in the art. See, for example, the sections dedicated to B-cell antigen in McMichael, ed. (1987; 1989) *Leukocyte Typing III and IV* (Oxford University Press, New York); U.S. Pat. Nos. 5,674, 492; 5,874,082; 5,677,165; 6,056,959; WO 00/63395; International Publication Nos. WO 02/28905 and WO 02/28904; Gordon et al. (1988) *J. Immunol.* 140:1425; Valle et al. (1989) *Eur. J. Immunol.* 19:1463; Clark et al. (1986) *PNAS* 83:4494; Paulie et al. (1989) *J. Immunol.* 142:590; Gordon et al. (1987) *Eur. J. Immunol.* 17:1535; Jabara et al. (1990) *J. Exp. Med.* 172:1861; Zhang et al. (1991) *J. Immunol.* 146:1836; Gascan et al. (1991) *J. Immunol.* 147:8; Banchereau et al. (1991) *Clin. Immunol. Spectrum* 3:8; and Banchereau et al. (1991) *Science* 251:70; all of which are herein incorporated by reference. Other anti-CD40 monoclonal antibodies include, but are not limited to, humanized anti-CD40 antibodies, such as SGN-40 (Tai et al. (2004) *Cancer Res.* 64:2846-52; U.S. Pat. No. 6,838,261), which is the humanized form of the murine anti-CD40 antibody SGN-14 (Francisco et al. (2000) *Cancer Res.* 60:3225-31), and the agonist and antagonist antibodies disclosed in U.S. Patent Application Publication No. 2004/0120948; herein incorporated by reference in their entirety.

Of particular interest to the present invention are antagonist anti-CD40 antibodies or antigen-binding fragments thereof that serve to block CD40L-mediated CD40 signaling, and which may also modulate ADCC, as does, for example, the CHIR-12.12 antibody described herein below.

Antagonist anti-CD40 antibodies for use in the stable liquid pharmaceutical compositions of the invention include monoclonal antibodies or antigen-binding fragments thereof that are capable of specifically binding to human CD40 antigen expressed on the surface of a human cell. In some embodiments, the antagonist anti-CD40 antibodies within the stable liquid pharmaceutical compositions exhibit a strong single-site binding affinity for the CD40 cell-surface antigen. Such monoclonal antibodies exhibit a dissociation equilibrium constant ($K_D$) for CD40 of at least $10^{-5}$ M, at least $3\times10^{-5}$ M, preferably at least $10^{-6}$ M to $10^{-7}$ M, more preferably at least $10^{-8}$ M to about $10^{-12}$ M, measured using a standard assay such as Biacore™. Biacore analysis is known in the art and details are provided in the "BIAapplications handbook." Methods described in WO 01/27160 can be used to modulate the binding affinity.

Of particular interest are antagonist anti-CD40 antibodies that are free of significant agonist activity as defined herein above but exhibit antagonist activity when bound to CD40 antigen on human cells, particularly when bound to CD40 antigen on neoplastic human B cells. In one embodiment of the invention, the antagonist anti-CD40 antibody is free of significant agonist activity in one B cell response. In another embodiment of the invention, the antagonist anti-CD40 antibody is free of significant agonist activity in assays of more than one B cell response (e.g., proliferation and differentiation, or proliferation, differentiation, and antibody production). Suitable monoclonal anti-CD40 antibodies have human constant regions; preferably they also have wholly or partially humanized framework regions; and most preferably are fully human antibodies or antigen-binding fragments thereof. Examples of such monoclonal antibodies are the antibodies designated herein as CHIR-5.9 and CHIR-12.12.

Thus, in some embodiments, the antagonist anti-CD40 antibody present in the stable liquid pharmaceutical compositions of the invention is the monoclonal antibody CHIR-5.9 or CHIR-12.12. The CHIR-5.9 and CHIR-12.12 antibodies are fully human anti-CD40 monoclonal antibodies of the IgG1 isotype produced from the hybridoma cell lines 131.2F8.5.9 (referred to herein as the cell line 5.9) and 153.8E2.D10.D6.12.12 (referred to herein as the cell line 12.12). These cell lines were created using splenocytes from immunized xenotypic mice containing the human IgG1 heavy chain locus and the human κ chain locus (XenoMouse® technology; Abgenix; Fremont, Calif.). The spleen cells were fused with the mouse myeloma SP2/0 cells (Sierra BioSource). The resulting hybridomas were sub-cloned several times to create the stable monoclonal cell lines 5.9 and 12.12. Other antibodies of the invention may be prepared similarly using mice transgenic for human immunoglobulin loci or by other methods known in the art and/or described herein.

The nucleotide and amino acid sequences of the variable regions of the CHIR-12.12 antibody, and the amino acid sequences of the variable regions of the CHIR-5.9 antibody, are disclosed herein. More particularly, the amino acid sequences for the leader, variable, and constant regions for the light chain and heavy chain for mAb CHIR-12.12 are set forth in SEQ ID NO:2 (complete sequence for the light chain of mAb CHIR-12.12), SEQ ID NO:4 (complete sequence for the heavy chain for mAb CHIR-12.12), and SEQ ID NO:5 (complete sequence for a variant of the heavy chain for mAb CHIR-12.12 set forth in SEQ ID NO:4, where the variant comprises a serine substitution for the alanine residue at position 153 of SEQ ID NO:4). The nucleotide sequences encoding the light chain and heavy chain for mAb CHIR-12.12 are set forth in SEQ ID NO: 1 (coding sequence for the light chain for mAb CHIR-12.12) and SEQ ID NO:3 (coding sequence for the heavy chain for mAb CHIR-12.12). The amino acid sequences for the leader, variable, and constant regions for the light chain and heavy chain of the CHIR-5.9 mAb are set forth in SEQ ID NO:6 (complete sequence for the light chain of mAb CHIR-5.9), SEQ ID NO:7 (complete sequence for the heavy chain of mAb CHIR-5.9), and SEQ ID NO:8 (complete sequence for a variant of the heavy chain of mAb CHIR-5.9 set forth in SEQ ID NO:7, where the variant comprises a serine substitution for the alanine residue at position 158 of SEQ ID NO:7). Further, hybridomas expressing CHIR-5.9 (mouse hybridoma line 131.2F8.5.9 (CMCC#12047) and CHIR-12.12 (mouse hybridoma line 153.8E2.D10.D6.12.12 (CMCC#12056) antibodies have been deposited with the ATCC (American Type Culture Collection; 10801 University Blvd., Manassas, Va. 20110-2209 (USA)) on Sep. 17, 2003, with a patent deposit designation of PTA-5542 and PTA-5543, respectively.

In addition to antagonist activity, anti-CD40 antibodies for use in the stable liquid pharmaceutical compositions of the present invention can have another mechanism of action against a tumor cell. For example, native CHIR-5.9 and CHIR-12.12 antibodies have ADCC activity. Alternatively, the variable regions of the CHIR-5.9 and CHIR-12.12 antibodies can be expressed on another antibody isotype that has ADCC activity. It is also possible to conjugate native forms, recombinant forms, or antigen-binding fragments of CHIR-5.9 or CHIR-12.12 to a cytotoxin, a therapeutic agent, or a radioactive metal ion or radioisotope, as noted herein below.

The CHIR-5.9 and CHIR-12.12 monoclonal antibodies bind soluble CD40 in ELISA-type assays, prevent the binding of CD40-ligand to cell-surface CD40, and displace the pre-bound CD40-ligand, as determined by flow cytometric assays. Antibodies CHIR-5.9 and CHIR-12.12 compete with each other for binding to CD40 but not with 15B8, the anti-CD40 monoclonal antibody described in U.S. Provisional Application Ser. No. 60/237,556, titled "Human Anti-CD40 Antibodies," filed Oct. 2, 2000, and PCT International Application No. PCT/US01/30857, also titled "Human Anti-CD40 Antibodies," filed Oct. 2, 2001, both of which are herein incorporated by reference in their entirety. When tested in vitro for effects on proliferation of B cells from normal human subjects, CHIR-5.9 and CHIR-12.12 act as antagonist anti-CD40 antibodies. Furthermore, CHIR-5.9 and CHIR-12.12 do not induce strong proliferation of human lymphocytes from normal subjects. These antibodies are able to kill CD40-expressing target cells by antibody dependent cellular cytotoxicity (ADCC). The binding affinity of CHIR-5.9 for human CD40 is $1.2 \times 10^{-8}$ M and the binding affinity of CHIR-122.12 is $5 \times 10^{-10}$ M, as determined by the Biacore™ assay.

Other antagonist anti-CD40 antibodies that share the binding characteristics of the monoclonal antibodies CHIR-5.9 and CHIR-12.12 described above include, but are not limited to the following: (1) the monoclonal antibodies produced by the hybridoma cell lines designated 131.2F8.5.9 (referred to herein as the cell line 5.9) and 153.8E2.D10.D6.12.12 (referred to herein as the cell line 12.12), deposited with the ATCC as Patent Deposit No. PTA-5542 and Patent Deposit No. PTA-5543, respectively; (2) a monoclonal antibody comprising an amino acid sequence selected from the group consisting of the sequence shown in SEQ ID NO:2, the sequence shown in SEQ ID NO:4, the sequence shown in SEQ ID NO:5, both the sequences shown in SEQ ID NO:2 and SEQ ID NO:4, and both the sequences shown in SEQ ID NO:2 and SEQ ID NO:5; (3) a monoclonal antibody comprising an amino acid sequence selected from the group consisting of the sequence shown in SEQ ID NO:6, the sequence shown in SEQ ID NO:7, the sequence shown in SEQ ID NO:8, both the sequences shown in SEQ ID NO:6 and SEQ ID NO:7, and both the sequences shown in SEQ ID NO:6 and SEQ ID NO:8; (4) a monoclonal antibody having an amino acid sequence encoded by a nucleic acid molecule comprising a nucleotide sequence selected from the group consisting of the nucleotide sequence shown in SEQ ID NO:1, the nucleotide sequence shown in SEQ ID NO:3, and both the sequences shown in SEQ ID NO:1 and SEQ ID NO:3; (5) a monoclonal antibody that binds to an epitope capable of binding the monoclonal antibody produced by the hybridoma cell line 5.9 or the hybridoma cell line 12.12; (6) a monoclonal antibody that binds to an epitope comprising residues 82-87 of the amino acid sequence shown in SEQ ID NO:10 or SEQ ID NO:12; (7) a monoclonal antibody that competes with the monoclonal antibody CHIR-5.9 or CHIR-12.12 in a competitive binding assay; and (8) a monoclonal antibody that is an antigen-binding fragment of the CHIR-12.12 or CHIR-5.9 monoclonal antibody or the foregoing monoclonal antibodies in preceding items (1)-(7), where the fragment retains the capability of specifically binding to the human CD40 antigen.

Those skilled in the art recognize that the antibodies and antigen-binding fragments of these antibodies described herein include antibodies and antigen-binding fragments thereof that are produced recombinantly using methods well known in the art and described herein below, and include, for example, monoclonal antibodies CHIR-5.9 and CHIR-12.12 that have been recombinantly produced.

Additional antagonist anti-CD40 antibodies include the monoclonal antibodies referred to as 5D12, 3A8 and 3C6, which are secreted by a hybridoma having ATCC accession numbers HB 11339, HB 12024 and HB 11340, respectively. See, for example, U.S. Pat. No. 6,315,998, herein incorporated by reference in its entirety.

Other antagonist anti-CD40 antibodies are known in the art. See, for example, the human anti-CD40 antibody produced by the hybridoma designated F4-465 disclosed in U.S. Patent Application Publication Nos. 20020142358 and 20030059427; herein incorporated by reference in their entirety. F4-465 was obtained from the HAC mouse (Kuroiwa et al. (2000) *Nature Biotech.* 10:1086 (2000)) and therefore expresses the human lambda light chain.

Production of Antibodies for the Pharmaceutical Compositions of the Invention

The antibodies for use in the pharmaceutical compositions of the present invention, for example, the antagonist anti-CD40 antibodies disclosed herein, can be produced using any antibody production method known to those of skill in the art. Thus, polyclonal sera may be prepared by conventional methods. In general, a solution containing the antigen of interest, the CD40 antigen, is first used to immunize a suitable animal, preferably a mouse, rat, rabbit, or goat. Rabbits or goats are preferred for the preparation of polyclonal sera due to the volume of serum obtainable, and the availability of labeled anti-rabbit and anti-goat antibodies.

Polyclonal sera can be prepared in a transgenic animal, preferably a mouse bearing human immunoglobulin loci. In a preferred embodiment, Sf9 cells expressing the protein of interest, for example, CD40, are used as the immunogen. Immunization can also be performed by mixing or emulsifying the antigen-containing solution in saline, preferably in an adjuvant such as Freund's complete adjuvant, and injecting the mixture or emulsion parenterally (generally subcutaneously or intramuscularly). A dose of 50-200 μg/injection is typically sufficient. Immunization is generally boosted 2-6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization. Polyclonal antisera are obtained by bleeding the immunized animal into a glass or plastic container, incubating the blood at 25° C. for one hour, followed by incubating at 4° C. for 2-18 hours. The serum is recovered by centrifugation (e.g., 1,000×g for 10 minutes). About 20-50 ml per bleed may be obtained from rabbits.

Production of the Sf 9 (*Spodoptera frugiperda*) cells is disclosed in U.S. Pat. No. 6,004,552, incorporated herein by reference. In the case of CD40, briefly, sequences encoding human CD40 were recombined into a baculovirus using transfer vectors. The plasmids were co-transfected with wild-type baculovirus DNA into Sf 9 cells. Recombinant baculovirus-infected Sf 9 cells were identified and clonally purified.

Preferably the antibody is monoclonal in nature. By "monoclonal antibody" is intended an antibody obtained from a population of substantially homogeneous antibodies, i.e., the individual antibodies comprising the population are identical except for possible naturally occurring mutations that may be present in minor amounts. The term is not limited regarding the species or source of the antibody. The term encompasses whole immunoglobulins as well as fragments such as Fab, F(ab')2, Fv, and others which retain the antigen binding function of the antibody. Monoclonal antibodies are highly specific, being directed against a single antigenic site; for example, in the case of anti-CD40 antibodies, the CD40 cell surface antigen. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256:495, or may be made by recombinant DNA methods (see, e.g., U.S. Pat. No. 4,816,567). The "monoclonal antibodies" may also be isolated from phage antibody libraries using the techniques described in, for example, Clackson et al. (1991) Nature 352:624-628; Marks et al. (1991) J. Mol. Biol. 222:581-597; and U.S. Pat. No. 5,514,548.

By "epitope" is intended the part of an antigenic molecule to which an antibody is produced and to which the antibody will bind. Epitopes can comprise linear amino acid residues (i.e., residues within the epitope are arranged sequentially one after another in a linear fashion), nonlinear amino acid residues (referred to herein as "nonlinear epitopes"; these epitopes are not arranged sequentially), or both linear and nonlinear amino acid residues.

Monoclonal antibodies can be prepared using the method of Kohler et al. (1975) Nature 256:495-496, or a modification thereof. Typically, a mouse is immunized with a solution containing an antigen. Immunization can be performed by mixing or emulsifying the antigen-containing solution in saline, preferably in an adjuvant such as Freund's complete adjuvant, and injecting the mixture or emulsion parenterally. Any method of immunization known in the art may be used to obtain the monoclonal antibodies of the invention. After immunization of the animal, the spleen (and optionally, several large lymph nodes) are removed and dissociated into single cells. The spleen cells may be screened by applying a cell suspension to a plate or well coated with the antigen of interest. The B cells expressing membrane bound immunoglobulin specific for the antigen bind to the plate and are not rinsed away. Resulting B cells, or all dissociated spleen cells, are then induced to fuse with myeloma cells to form hybridomas, and are cultured in a selective medium. The resulting cells are plated by serial dilution and are assayed for the production of antibodies that specifically bind the antigen of interest (and that do not bind to unrelated antigens). The selected monoclonal antibody (mAb)-secreting hybridomas are then cultured either in vitro (e.g., in tissue culture bottles or hollow fiber reactors), or in vivo (as ascites in mice).

Where antagonist anti-CD40 antibodies are to be prepared using recombinant DNA methods, the DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells described herein serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al. (1993) Curr. Opinion in Immunol. 5:256 and Phickthun (1992) Immunol. Revs. 130:151. Alternatively, antibody can be produced in a cell line such as a CHO cell line, as disclosed in U.S. Pat. Nos. 5,545,403; 5,545,405; and 5,998,144; incorporated herein by reference. Briefly the cell line is transfected with vectors capable of expressing a light chain and a heavy chain, respectively. By transfecting the two proteins on separate vectors, chimeric antibodies can be produced. Another advantage is the correct glycosylation of the antibody.

In some embodiments, the antagonist anti-CD40 antibody, for example, the CHIR-12.12 or CHIR-5.9 antibody, or antigen-binding fragment thereof is produced in CHO cells using the GS gene expression system (Lonza Biologics, Portsmouth, N.H.), which uses glutamine synthetase as a marker. See, also U.S. Pat. Nos. 5,122,464; 5,591,639; 5,658,759; 5,770,359; 5,827,739; 5,879,936; 5,891,693; and 5,981,216; the contents of which are herein incorporated by reference in their entirety.

Additionally, antibodies for use in the pharmaceutical compositions of the invention can be chimeric antibodies that have the desired binding characteristics. Thus, for example, chimeric anti-CD40 antibodies for use in the methods of the invention could have the binding characteristics of the CHIR-5.9 and CHIR-12.12 monoclonal antibodies described herein. By "chimeric" antibodies is intended antibodies that are most preferably derived using recombinant deoxyribonucleic acid techniques and which comprise both human (including immunologically "related" species, e.g., chimpanzee) and non-human components. Thus, the constant region of the chimeric antibody is most preferably substantially identical to the constant region of a natural human antibody; the variable region of the chimeric antibody is most preferably derived from a non-human source and has the desired antigenic specificity to the antigen of interest, i.e., the CD40 antigen. The non-human source can be any vertebrate source that can be used to generate antibodies to a human antigen or material comprising a human CD40 antigen. Such non-human sources include, but are not limited to, rodents (e.g., rabbit, rat, mouse, etc.; see, for example, U.S. Pat. No. 4,816,567, herein incorporated by reference) and non-human primates (e.g., Old World Monkey, Ape, etc.; see, for example, U.S. Pat. Nos. 5,750,105 and 5,756,096; herein incorporated by reference). As used herein, the phrase "immunologically active" when used in reference, for example, to chimeric anti-CD40 antibodies, means a chimeric antibody that binds human CD40.

By "humanized" is intended forms of antibodies that contain minimal sequence derived from non-human immunoglobulin sequences. For the most part, humanized antibodies are human immunoglobulins (recipient antibody) in which residues from a hypervariable region (also known as complementarity determining region or CDR) of the recipient are replaced by residues from a hypervariable region of a non-human species (donor antibody) such as mouse, rat, rabbit, or nonhuman primate having the desired specificity, affinity, and capacity. The phrase "complementarity determining region" refers to amino acid sequences which together define the binding affinity and specificity of the natural Fv region of a native immunoglobulin binding site. See, e.g., Chothia et al (1987) J. Mol. Biol. 196:901-917; Kabat et al (1991) U.S. Dept. of Health and Human Services, NIH Publication No. 91-3242). The phrase "constant region" refers to the portion of the antibody molecule that confers effector functions. In previous work directed towards producing non-immunogenic antibodies for use in therapy of human disease, mouse constant regions were substituted by human constant regions. The constant regions of the subject humanized antibodies were derived from human immunoglobulins. However, these humanized antibodies still elicited an unwanted and potentially dangerous immune response in humans and there was a loss of affinity. Humanized antibodies, for example, humanized anti-CD40 antibodies, for use in the pharmaceutical compositions of the present invention have binding characteristics similar to those exhibited by the parent antibody of interest, for example, the CHIR-5.9 and CHIR-12.12 monoclonal antibodies described herein.

Humanization can be essentially performed following the method of Winter and co-workers (Jones et al. (1986) *Nature* 321:522-525; Riechmann et al. (1988) *Nature* 332:323-327; Verhoeyen et al. (1988) *Science* 239:1534-1536), by substituting rodent or mutant rodent CDRs or CDR sequences for the corresponding sequences of a human antibody. See also U.S. Pat. Nos. 5,225,539; 5,585,089; 5,693,761; 5,693,762; 5,859,205; herein incorporated by reference. In some instances, residues within the framework regions of one or more variable regions of the human immunoglobulin are replaced by corresponding non-human residues (see, for example, U.S. Pat. Nos. 5,585,089; 5,693,761; 5,693,762; and 6,180,370). Furthermore, humanized antibodies may comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the hypervariable regions correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al. (1986) *Nature* 331:522-525; Riechmann et al. (1988) *Nature* 332:323-329; and Presta (1992) *Curr. Op. Struct. Biol.* 2:593-596; herein incorporated by reference. Accordingly, such "humanized" antibodies may include antibodies wherein substantially less than an intact human variable domain has been substituted by the corresponding sequence from a non-human species. In practice, humanized antibodies are typically human antibodies in which some CDR residues and possibly some framework residues are substituted by residues from analogous sites in rodent antibodies. See, for example, U.S. Pat. Nos. 5,225,539; 5,585,089; 5,693,761; 5,693,762; 5,859,205. See also U.S. Pat. No. 6,180,370, and International Publication No. WO 01/27160, where humanized antibodies and techniques for producing humanized antibodies having improved affinity for a predetermined antigen are disclosed.

The present invention can also be practiced using xenogeneic or modified antibodies produced in a non-human mammalian host, more particularly a transgenic mouse, characterized by inactivated endogenous immunoglobulin (Ig) loci. In such transgenic animals, competent endogenous genes for the expression of light and heavy subunits of host immunoglobulins are rendered non-functional and substituted with the analogous human immunoglobulin loci. These transgenic animals produce human antibodies in the substantial absence of light or heavy host immunoglobulin subunits. See, for example, U.S. Pat. Nos. 5,877,397 and 5,939,598, herein incorporated by reference.

In some embodiments, fully human antibodies to CD40, for example, are obtained by immunizing transgenic mice. One such mouse is obtained using XenoMouse® technology (Abgenix; Fremont, Calif.), and is disclosed in U.S. Pat. Nos. 6,075,181, 6,091,001, and 6,114,598, all of which are incorporated herein by reference. To produce the antibodies disclosed herein, mice transgenic for the human Ig $G_1$ heavy chain locus and the human κ light chain locus were immunized with Sf 9 cells expressing human CD40. Mice can also be transgenic for other isotypes. Fully human anti-CD40 antibodies useful in the stable liquid pharmaceutical compositions of the present invention are characterized by binding properties similar to those exhibited by the CHIR-5.9 and CHIR-12.12 monoclonal antibodies disclosed herein.

Fragments of a particular antibody of interest, for example, an anti-CD40 antibody, including antagonist anti-CD40 antibody, are suitable for use in the stable liquid pharmaceutical compositions of the invention so long as they retain the desired affinity of the full-length antibody. Thus, for example, a fragment of an anti-CD40 antibody will retain the ability to bind to the CD40 B cell surface antigen. Such fragments are characterized by properties similar to the corresponding full-length antibody. Thus, for example, a fragment of a full-length antagonist anti-CD40 antibody will specifically bind a human CD40 antigen expressed on the surface of a human cell, and is free of significant agonist activity but exhibits antagonist activity when bound to a CD40 antigen on a human CD40-expressing cell. Such fragments are referred to herein as "antigen-binding" fragments.

Suitable antigen-binding fragments of an antibody comprise a portion of a full-length antibody, generally the antigen-binding or variable region thereof. Examples of antibody fragments include, but are not limited to, Fab, $F(ab')_2$, and Fv fragments and single-chain antibody molecules. By "Fab" is intended a monovalent antigen-binding fragment of an immunoglobulin that is composed of the light chain and part of the heavy chain. By $F(ab')_2$ is intended a bivalent antigen-binding fragment of an immunoglobulin that contains both light chains and part of both heavy chains. By "single-chain Fv" or "sFv" antibody fragments is intended fragments comprising the $V_H$ and $V_L$ domains of an antibody, wherein these domains are present in a single polypeptide chain. See, for example, U.S. Pat. Nos. 4,946,778, 5,260,203, 5,455,030, and 5,856,456, herein incorporated by reference. Generally, the Fv polypeptide further comprises a polypeptide linker between the $V_H$ and $V_L$ domains that enables the sFv to form the desired structure for antigen binding. For a review of sFv see Pluckthun (1994) in *The Pharmacology of Monoclonal Antibodies*, Vol. 113, ed. Rosenburg and Moore (Springer-Verlag, New York), pp. 269-315. Antigen-binding fragments of the antagonist anti-CD40 antibodies disclosed herein can also be conjugated to a cytotoxin to effect killing of the target cancer cells, as described herein below.

Antibodies or antibody fragments can be isolated from antibody phage libraries generated using the techniques described in, for example, McCafferty et al. (1990) *Nature* 348:552-554 (1990) and U.S. Pat. No. 5,514,548. Clackson et al (1991) *Nature* 352:624-628 and Marks et al. (1991) *J. Mol. Biol.* 222:581-597 describe the isolation of murine and human antibodies, respectively, using phage libraries. Subsequent publications describe the production of high affinity (nM range) human antibodies by chain shuffling (Marks et al. (1992) *Bio/Technology* 10:779-783), as well as combinatorial infection and in vivo recombination as a strategy for constructing very large phage libraries (Waterhouse et al. (1993) *Nucleic. Acids Res.* 21:2265-2266). Thus, these techniques are viable alternatives to traditional monoclonal antibody hybridoma techniques for isolation of monoclonal antibodies.

Various techniques have been developed for the production of antibody fragments. Traditionally, these fragments were derived via proteolytic digestion of intact antibodies (see, e.g., Morimoto et al. (1992) *Journal of Biochemical and Biophysical Methods* 24:107-117 (1992) and Brennan et al. (1985) *Science* 229:81). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al. (1992) *Bio/Technology* 10: 163-167). According to another approach, F(ab')$_2$ fragments can be isolated directly from recombinant host cell culture. Other techniques for the production of antibody fragments will be apparent to the skilled practitioner.

Antagonist anti-CD40 antibodies for use in the stable liquid pharmaceutical compositions of the present invention include the CHIR-5.9 and CHIR-12.12 monoclonal antibodies disclosed herein as well as antibodies differing from this antibody but retaining the CDRs; and antibodies with one or more amino acid addition(s), deletion(s), or substitution(s), wherein the antagonist activity is measured by inhibition of B-cell proliferation and/or differentiation. The invention also encompasses de-immunized antibodies, particularly de-immunized antagonist anti-CD40 antibodies, which can be produced as described in, for example, International Publication Nos. WO 98/52976 and WO 0034317; herein incorporated by reference. In this manner, residues within the antagonist anti-CD40 antibodies of the invention are modified so as to render the antibodies non- or less immunogenic to humans while retaining their antagonist activity toward human CD40-expressing cells, wherein such activity is measured by assays noted elsewhere herein. Also included within the scope of the present invention are fusion proteins comprising an antibody of interest, for example, an antagonist anti-CD40 antibody, or a fragment thereof, which fusion proteins can be synthesized or expressed from corresponding polynucleotide vectors, as is known in the art. Such fusion proteins are described with reference to conjugation of antibodies as noted elsewhere herein.

Any known antibody having the binding specificity of interest can have sequence variations produced using methods described in, for example, Patent Publication Nos. EP 0 983 303 A1, WO 00/34317, and WO 98/52976, incorporated herein by reference. For example, it has been shown that sequences within the CDR can cause an antibody to bind to MHC Class II and trigger an unwanted helper T-cell response. A conservative substitution can allow the antibody to retain binding activity yet lose its ability to trigger an unwanted T-cell response. Any such conservative or non-conservative substitutions can be made using art-recognized methods, such as those noted elsewhere herein, and the resulting antibodies can also be used in the stable liquid pharmaceutical compositions of the present invention. The variant antibodies can be routinely tested for the particular activity, for example, antagonist activity, affinity, and specificity using methods described herein.

The antagonist anti-CD40 antibody produced by any of the methods described above, or any other method not disclosed herein, can be used in a manner similar to the CHIR-12.12 or CHIR-5.9 antibody where it possesses at least one of the following biological activities: inhibition of immunoglobulin secretion by normal human peripheral B cells stimulated by T cells; inhibition of survival and/or proliferation of normal human peripheral B cells stimulated by Jurkat T cells; inhibition of survival and/or proliferation of normal human peripheral B cells stimulated by CD40L-expressing cells or soluble CD40 ligand (sCD40L); inhibition of "survival" anti-apoptotic intracellular signals in any cell stimulated by sCD40L or solid-phase CD40L; inhibition of CD40 signal transduction in any cell upon ligation with sCD40L or solid-phase CD40L; inhibition of proliferation of human malignant B cells; deletion, anergy and/or tolerance induction of CD40-bearing target cells or cells bearing cognate ligands to CD40 including, but not limited to, T cells and B cells; induction of expansion or activation of CD4$^+$ CD25$^+$ regulatory T cells (see for example, donor alloantigen-specific tissue rejection via CD40-CD40L interference, van Maurik et al. (2002) *J. Immunol.* 169:5401-5404); cytotoxicity via any mechanism (including, but not limited to, antibody-dependent cell-mediated cytotoxicity (ADCC), complement-dependent cytotoxicity (CDC), down-regulation of proliferation, and/or apoptosis in target cells); modulation of target cell cytokine secretion and/or cell surface molecule expression; and combinations thereof. Assays for measuring the desired biological activity of the antagonist anti-CD40 antibodies disclosed herein, and antigen-binding fragments thereof, can be performed as described in provisional applications entitled "Antagonist Anti-CD40 Monoclonal Antibodies and Methods for Their Use," filed Nov. 4, 2003, Nov. 26, 2003, and Apr. 27, 2004, and assigned U.S. Patent Application Nos. 60/517,337, 60/525,579, and 60/565,710, respectively; and International Patent Application No. PCT/US2004/037152, also entitled "Antagonist Anti-CD40 Monoclonal Antibodies and Methods for Their Use," filed Nov. 4, 2004, and published as WO 2005/044854; the contents of each of which are herein incorporated by reference in their entirety. See also the assays described in provisional application entitled "Methods for Diagnosis and Treatment of Proliferative Disorders Mediated by CD40 Signaling," filed Dec. 9, 2005, and assigned U.S. Patent Application No. 60/749,285, and corresponding International Patent Application No. PCT/US2006/019414, filed May 18, 2006, and published as WO 2006/125143; and provisional application entitled "Methods for Diagnosis and Treatment of Diseases Having an Autoimmune and/or Inflammatory Component," filed Dec. 9, 2005, and assigned U.S. Patent Application No. 60/749,336, and corresponding International Patent Application No. PCT/US2006/019325, filed May 18, 2006, and published as WO 2006/125117; the contents of each of which are herein incorporated by reference in their entirety. Also see the assays described in Schultze et al. (1998) *Proc. Natl. Acad. Sci. USA* 92:8200-8204; Denton et al. (1998) *Pediatr. Transplant.* 2:6-15; Evans et al. (2000) *J. Immunol.* 164:688-697; Noelle (1998) *Agents Actions Suppl.* 49:17-22; Lederman et al. (1996) *Curr. Opin. Hematol.* 3:77-86; Coligan et al. (1991) *Current Protocols in Immunology* 13:12; Kwekkeboom et al. (1993) *Immunology* 79:439-444; and U.S. Pat. Nos. 5,674,492 and 5,847,082; herein incorporated by reference.

A representative assay to detect antagonist anti-CD40 antibodies specific to the CD40-antigen epitopes identified herein is a "competitive binding assay." Competitive binding assays are serological assays in which unknowns are detected and quantitated by their ability to inhibit the binding of a labeled known ligand to its specific antibody. This is also referred to as a competitive inhibition assay. In a representative competitive binding assay, labeled CD40 polypeptide is precipitated by candidate antibodies in a sample, for example, in combination with monoclonal antibodies raised against one or more epitopes of the monoclonal antibodies of the invention. Anti-CD40 antibodies that specifically react with an epitope of interest can be identified by screening a series of antibodies prepared against a CD40 protein or fragment of the protein comprising the particular epitope of the CD40 protein of interest. For example, for human CD40, epitopes of interest include epitopes comprising linear and/or nonlinear amino acid residues of the short isoform of human CD40 (see Gen- Bank Accession No. NP_690593) set forth in SEQ ID NO: 10, encoded by the sequence set forth SEQ ID NO:9; see also GenBank Accession No. NM_152854), or of the long isoform of human CD40 (see GenBank Accession Nos. CAA43045 and NP_001241, set forth in SEQ ID NO: 12, encoded by the sequence set forth in SEQ ID NO: 11; see GenBank Accession Nos. X60592 and NM-001250). Alternatively, competitive binding assays with previously identified suitable antagonist anti-CD40 antibodies could be used to select monoclonal antibodies comparable to the previously identified antibodies.

Antibodies employed in such immunoassays may be labeled or unlabeled. Unlabeled antibodies may be employed in agglutination; labeled antibodies may be employed in a wide variety of assays, employing a wide variety of labels. Detection of the formation of an antibody-antigen complex between an anti-CD40 antibody and an epitope of interest can be facilitated by attaching a detectable substance to the antibody. Suitable detection means include the use of labels such as radionuclides, enzymes, coenzymes, fluorescers, chemiluminescers, chromogens, enzyme substrates or co-factors, enzyme inhibitors, prosthetic group complexes, free radicals, particles, dyes, and the like. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material is luminol; examples of bioluminescent materials include luciferase, luciferin, and aequorin; and examples of suitable radioactive material include $^{125}$I, $^{131}$I, $^{35}$S, or $^{3}$H. Such labeled reagents may be used in a variety of well-known assays, such as radioimmunoassays, enzyme immunoassays, e.g., ELISA, fluorescent immunoassays, and the like. See for example, U.S. Pat. Nos. 3,766,162; 3,791,932; 3,817,837; and 4,233,402.

Any of the previously described antagonist anti-CD40 antibodies or antigen-binding fragments thereof, may be conjugated prior to use in the pharmaceutical compositions of the present invention. Methods for producing conjugated antibodies are known in the art. Thus, the antibody may be labeled using an indirect labeling or indirect labeling approach. By "indirect labeling" or "indirect labeling approach" is intended that a chelating agent is covalently attached to an antibody and at least one radionuclide is inserted into the chelating agent. See, for example, the chelating agents and radionuclides described in Srivagtava and Mease (1991) *Nucl. Med. Bio.* 18:589-603, herein incorporated by reference. Suitable labels include fluorophores, chromophores, radioactive atoms (particularly $^{32}$P and $^{125}$I), electron-dense reagents, enzymes, and ligands having specific binding partners. Enzymes are typically detected by their activity. For example, horseradish peroxidase is usually detected by its ability to convert 3,3',5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefore. Other specific binding partners include biotin and avidin or streptavidin, Ig G and protein A, and the numerous receptor-ligand couples known in the art. It should be understood that the above description is not meant to categorize the various labels into distinct classes, as the same label may serve in several different modes. For example, $^{125}$I may serve as a radioactive label or as an electron-dense reagent. HRP may serve as enzyme or as antigen for a mAb. Further, one may combine various labels for desired effect. For example, mAbs and avidin also require labels in the practice of this invention: thus, one might label a mAb with biotin, and detect its presence with avidin labeled with $^{125}$I, or with an anti-biotin mAb labeled with HRP. Other permutations and possibilities will be readily apparent to those of ordinary skill in the art, and are considered as equivalents within the scope of the instant invention.

Alternatively, an antagonist anti-CD40 antibody of interest may be labeled using "direct labeling" or a "direct labeling approach," where a radionuclide is covalently attached directly to an antibody (typically via an amino acid residue). Preferred radionuclides are provided in Srivagtava and Mease (1991) supra. The indirect labeling approach is particularly preferred. See also, for example, International Publication Nos. WO 00/52031 and WO 00/52473, where a linker is used to attach a radioactive label to antibodies; and the labeled forms of anti-CD40 antibodies described in U.S. Pat. No. 6,015,542; herein incorporated by reference.

Variants of Antibodies

The pharmaceutical compositions of the present invention can be formulated using variants of an antagonist anti-CD40 antibody known in the art. Such variants will retain the desired binding properties of the parent antibody. Thus, for example, where the antagonist anti-CD40 antibody to be formulated is a variant of the parent CHIR-12.12 or CHIR-5.9 antibody, the variant antibody will retain the binding properties of the parent CHIR-12.12 or CHIR-5.9 antibody. Methods for making antibody variants are generally available in the art.

For example, amino acid sequence variants of an antagonist anti-CD40 antibody, for example, the CHIR-5.9 or CHIR-12.12 monoclonal antibody described herein, can be prepared by mutations in the cloned DNA sequence encoding the antibody of interest. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. USA* 82:488-492; Kunkel et al. (1987) *Methods Enzymol.* 154:367-382; Sambrook et al. (1989) *Molecular Cloning: A Laboratory Manual* (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest may be found in the model of Dayhoff et al. (1978) in *Atlas of Protein Sequence and Structure* (Natl. Biomed. Res. Found., Washington, D.C.), herein incorporated by reference. Conservative substitutions, such as exchanging one amino acid with another having similar properties, may be preferred. Examples of conservative substitutions include, but are not limited to, Gly⇔Ala, Val⇔Ile⇔Leu, Asp⇔Glu, Lys⇔Arg, Asn⇔Gln, and Phe⇔Trp⇔Tyr.

In constructing variants of an antagonist anti-CD40 antibody polypeptide of interest, for example, the CHIR-12.12 or CHIR-5.9 antibody, modifications are made such that variants continue to possess the desired activity, i.e., similar binding affinity and, in the case of antagonist anti-CD40 antibodies, are capable of specifically binding to a human CD40 antigen expressed on the surface of a human cell, and being free of significant agonist activity but exhibiting antagonist activity when bound to a CD40 antigen on a human CD40-expressing cell. Obviously, any mutations made in the DNA encoding the variant polypeptide must not place the sequence out of reading frame and preferably will not create complementary regions that could produce secondary mRNA structure. See EP Patent Application Publication No. 75,444.

In addition, the constant region of an antagonist anti-CD40 antibody can be mutated to alter effector function in a number of ways. For example, see U.S. Pat. No. 6,737,056B1 and U.S. Patent Application Publication No. 2004/0132101A1, which disclose Fc mutations that optimize antibody binding to Fc receptors.

Preferably, variants of a reference antagonist antiCD40 antibody have amino acid sequences that have at least 70% or 75% sequence identity, preferably at least 80% or 85% sequence identity, more preferably at least 90%, 91%, 92%, 93%, 94% or 95% sequence identity to the amino acid sequence for the reference antibody, for example, the CHIR-5.9 or CHIR-12.12 monoclonal antibody described herein, or to a shorter portion of the reference antibody molecule. More preferably, the molecules share at least 96%, 97%, 98% or 99% sequence identity. For purposes of the present invention, percent sequence identity is determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman (1981) *Adv. Appl. Math.* 2:482-489. A variant may, for example, differ from the reference antagonist anti-CD40 antibody by as few as 1 to 15 amino acid residues, as few as 1 to 10 amino acid residues, such as 6-10, as few as 5, as few as 4, 3, 2, or even 1 amino acid residue.

With respect to optimal alignment of two amino acid sequences, the contiguous segment of the variant amino acid sequence may have additional amino acid residues or deleted amino acid residues with respect to the reference amino acid sequence. The contiguous segment used for comparison to the reference amino acid sequence will include at least 20 contiguous amino acid residues, and may be 30, 40, 50, or more amino acid residues. Corrections for sequence identity associated with conservative residue substitutions or gaps can be made (see Smith-Waterman homology search algorithm).

Methods of Therapy Using the Pharmaceutical Compositions of the Invention

The pharmaceutical compositions of the present invention find use in treating a subject having a cancer or premalignant condition that is associated with CD40-expressing cells, or for treating an inflammatory disease and/or autoimmune disease that is associated with CD40-expressing cells. "Treatment" is herein defined as the application or administration of a pharmaceutical composition comprising the antagonist anti-CD40 antibody to a subject, or application or administration of a pharmaceutical composition comprising the antagonist anti-CD40 antibody to an isolated tissue or cell line from a subject, where the subject has a disease, a symptom of a disease, or a predisposition toward a disease, where the purpose is to cure, heal, alleviate, relieve, alter, remedy, ameliorate, improve, or affect the disease, the symptoms of the disease, or the predisposition toward the disease.

By "subject" is intended any animal. Preferably the subject is mammalian, must preferably the subject is human. Mammals of particular importance other than human include, but are not limited to, dogs, cats, cows, horses, sheep, and pigs.

When administration is for the purpose of treatment, administration may be for a prophylactic or therapeutic purpose. When provided prophylactically, the pharmaceutical composition is provided in advance of any symptom. The prophylactic administration of the pharmaceutical composition serves to prevent or attenuate any subsequent symptom. When provided therapeutically, the pharmaceutical composition is provided at (or shortly after) the onset of a symptom. The therapeutic administration of the pharmaceutical composition serves to attenuate any actual symptom.

Typical routes of administration include, but are not limited to, oral administration and parenteral administration, including intravenous, intramuscular, intrathecal, intranasal, sublingual, intra-arterial and intraperitoneal injection or infusion, and subcutaneous injection. Methods to accomplish this administration are known to those of ordinary skill in the art.

In preferred embodiments, the pharmaceutical compositions of the invention are administered intravenously. Intravenous administration occurs preferably by infusion over a period of about 1 to about 10 hours, more preferably over about 1 to about 8 hours, even more preferably over about 2 to about 7 hours, still more preferably over about 4 to about 6 hours, depending upon the antagonist anti-CD40 antibody being administered. The initial infusion with the pharmaceutical composition may be given over a period of about 4 to about 6 hours with subsequent infusions delivered more quickly. Subsequent infusions may be administered over a period of about 1 to about 6 hours, including, for example, about 1 to about 4 hours, about 1 to about 3 hours, or about 1 to about 2 hours.

A pharmaceutically effective amount of a pharmaceutical composition of the invention is administered to a subject. By "pharmaceutically effective amount" is intended an amount that is useful in the treatment of a disease or condition, where treatment can be for a prophylactic or therapeutic purpose as noted herein above. In this manner, a pharmaceutically effective amount of the composition will administer a therapeutically effective dose or amount of the antagonist anti-CD40 antibody to the subject in need of treatment. By "therapeutically effective dose or amount" or "effective amount" is intended an amount of the antagonist anti-CD40 antibody that, when administered brings about a positive therapeutic response with respect to treatment of a patient with a disease comprising CD40-expressing cells. In some embodiments of the invention, the therapeutically effective dose of the antagonist anti-CD40 antibody, for example, the monoclonal antibody CHIR-12.12 or CHIR-5.9, or antigen-binding fragment thereof, is in the range from about 0.01 mg/kg to about 40 mg/kg, from about 0.01 mg/kg to about 30 mg/kg, from about 0.1 mg/kg to about 30 mg/kg, from about 1 mg/kg to about 30 mg/kg, from about 3 mg/kg to about 30 mg/kg, from about 3 mg/kg to about 25 mg/kg, from about 3 mg/kg to about 20 mg/kg, from about 5 mg/kg to about 15 mg/kg, or from about 7 mg/kg to about 12 mg/kg. It is recognized that the method of treatment may comprise a single administration of a therapeutically effective dose or multiple administrations of a therapeutically effective dose of the antagonist anti-CD40 antibody, or antigen-binding fragment thereof.

The pharmaceutical compositions of the invention find use in treating any subject having a cancer or pre-malignant condition that is responsive to treatment with an anti-CD40 therapeutic agent, more particularly, an antagonist anti-CD40 antibody. Methods for determining responsiveness of a cancer or pre-malignant condition to treatment with an anti-CD40 antibody include diagnostic and prognostic assays, for example, the assays described in the copending and commonly owned provisional patent application entitled "Methods for Diagnosis and Treatment of Proliferative Disorders Mediated by CD40 Signaling," filed Dec. 9, 2005, and assigned U.S. Patent Application No. 60/749,285, and corresponding International Patent Application No. PCT/US2006/019414, filed May 18, 2006, and published as WO 2006/125143; the contents of which are herein incorporated by reference in their entirety. Similarly, the pharmaceutical composition of the invention find use in treating any subject having an inflammatory and/or autoimmune disease that is responsive to treatment with an anti-CD40 therapeutic agent, particularly an anti-CD40 antibody. Methods for determining responsiveness of an inflammatory and/or autoimmune disease to treatment with an anti-CD40 antibody include diagnostic and prognostic assays, for example, the assays described in the copending and commonly owned provisional patent application entitled "Methods for Diagnosis and Treatment of Diseases Having an Autoimmune and/or Inflammatory Component," filed Dec. 9, 2005, and assigned U.S. Patent Application No. 60/749,336, and corresponding International Patent Application No. PCT/US2006/019325, filed May 18, 2006, and published as WO 2005/125117; the contents of which are herein incorporated by reference in their entirety.

"Tumor," as used herein, refers to all neoplastic cell growth and proliferation, whether malignant or benign, and all pre-cancerous and cancerous cells and tissues. "Neoplastic," as used herein, refers to any form of dysregulated or unregulated cell growth, whether malignant or benign, resulting in abnormal tissue growth. Thus, "neoplastic cells" include malignant and benign cells having dysregulated or unregulated cell growth.

By "anti-tumor activity" is intended a reduction in the rate of malignant CD40-expressing cell proliferation or accumulation, and hence a decline in growth rate of an existing tumor or in a tumor that arises during therapy, and/or destruction of existing neoplastic (tumor) cells or newly formed neoplastic cells, and hence a decrease in the overall size of a tumor during therapy. Therapy with the antagonist anti-CD40 antibody-containing pharmaceutical compositions of the invention causes a physiological response that is beneficial with respect to treatment of cancers and pre-malignant conditions associated with stimulation of CD40 signaling on CD40-expressing cells in a human.

The terms "cancer" and "cancerous" refer to or describe the physiological condition in mammals that is typically characterized by unregulated cell growth. Examples of cancer include, but are not limited to, lymphoma and leukemia, and solid tumors. By "B cell-related cancer" or "cancer of B-cell lineage" is intended any type of cancer in which the dysregulated or unregulated cell growth is associated with B cells.

By "refractory" in the context of a cancer is intended the particular cancer is resistant to, or non-responsive to, therapy with a particular therapeutic agent, for example, an antagonist anti-CD40 antibody of interest. A cancer can be refractory to therapy with a particular therapeutic agent either from the onset of treatment with the particular therapeutic agent (i.e., non-responsive to initial exposure to the therapeutic agent), or as a result of developing resistance to the therapeutic agent, either over the course of a first treatment period with the therapeutic agent or during a subsequent treatment period with the therapeutic agent.

The pharmaceutical compositions of the present invention find use in treating a subject that is in need of therapeutic intervention for a cancer or pre-malignant condition that is mediated by stimulation of CD40 signaling on CD40-expressing cells, or for any inflammatory or autoimmune disease that is mediated by CD40 signaling on CD40-expressing cells. By "CD40-expressing cell" is intended normal, pre-malignant, and malignant cells expressing CD40 antigen. In some embodiments, the CD40-expressing cell is a malignant B cell. By "malignant" B cell is intended any neoplastic B cell, including but not limited to B cells derived from lymphomas including low-, intermediate-, and high-grade B cell lymphomas, immunoblastic lymphomas, non-Hodgkin's lymphomas, Hodgkin's disease, Epstein-Barr Virus (EBV) induced lymphomas, and AIDS-related lymphomas, as well as B cell acute lymphoblastic leukemias, myelomas, chronic lymphocytic leukemias, and the like. In other embodiments, the CD40-expressing cell is a carcinoma or sarcoma cell. By "CD40-expressing carcinoma cell" or CD40-expressing sarcoma cell" is intended any malignant (i.e., neoplastic) or pre-malignant carcinoma or sarcoma cell of a solid tumor that expresses the CD40 cell-surface antigen. For purposes of the present invention, cancerous and pre-cancerous or pre-malignant cells that express the CD40 antigen are referred to as "CD40-expressing neoplastic cells." Methods for detecting CD40 expression in cells are well known in the art and include, but are not limited to, PCR techniques, immunohistochemistry, flow cytometry, Western blot, ELISA, and the like. Where treatment with an antagonist anti-CD40 antibody or antigen-binding fragment thereof is warranted, the pharmaceutical composition comprising the antagonist anti-CD40 antibody or antigen-binding fragment thereof can be administered by any suitable route of administration.

The subject who is in need of treatment intervention with a pharmaceutical composition of the present invention can be afflicted with, or at risk of developing or relapsing with, any cancer or pre-malignant condition that is mediated by CD40 signaling on CD40-expressing neoplastic cells. Examples of such cancers and pre-malignant conditions include, but are not limited to, any of the cancers of B-cell lineage, non-B cell hematological malignancies, and solid tumors that are known to be mediated via CD40 signaling on CD40-expressing neoplastic cells.

Examples of cancers of B-cell lineage that comprise CD40-expressing neoplastic cells are acute lymphoblastic leukemia (ALL), chronic lymphocytic leukemia (CLL), prolymphocytic leukemia (PLL), hairy cell leukemia, Hodgkin's disease, multiple myeloma, Waldenstrom's macroglobulinemia, heavy chain disease, and the lymphomas, including, but not limited to, diffuse small lymphocytic lymphoma, follicular, DLBCL, mucosal associated lymphoid tissue lymphoma, monocytoid B cell lymphoma, splenic lymphoma, lymphomatoid granulomatosis, intravascular lymphomatosis, immunoblastic lymphoma, AIDS-related lymphoma, and the like.

Thus, the pharmaceutical compositions of the invention find use in the treatment of subjects having non-Hodgkin's lymphomas related to abnormal, uncontrollable B cell proliferation or accumulation. For purposes of the present invention, such lymphomas will be referred to according to the Working Formulation classification scheme, that is those B cell lymphomas categorized as low grade, intermediate grade, and high grade (see "The Non-Hodgkin's Lymphoma Pathologic Classification Project," Cancer 49 (1982):2112-2135). Thus, low-grade B cell lymphomas include small lymphocytic, follicular small-cleaved cell, and follicular mixed small-cleaved and large cell lymphomas; intermediate-grade lymphomas include follicular large cell, diffuse small cleaved cell, diffuse mixed small and large cell, and diffuse large cell lymphomas; and high-grade lymphomas include large cell immunoblastic, lymphoblastic, and small non-cleaved cell lymphomas of the Burkitt's and non-Burkitt's type.

It is recognized that the pharmaceutical compositions of the invention are useful in therapeutic treatment of B cell lymphomas that are classified according to the Revised European and American Lymphoma Classification (REAL) system. Such B cell lymphomas include, but are not limited to, lymphomas classified as precursor B cell neoplasms, such as B lymphoblastic leukemia/lymphoma; peripheral B cell neoplasms, including B cell chronic lymphocytic leukemia/small lymphocytic lymphoma, lymphoplasmacytoid lymphoma/immunocytoma, mantle cell lymphoma (MCL), follicle center lymphoma (follicular) (including diffuse small cell, diffuse mixed small and large cell, and diffuse large cell lymphomas), marginal zone B cell lymphoma (including extranodal, nodal, and splenic types), plasmacytoma/myeloma, diffuse large cell B cell lymphoma of the subtype primary mediastinal (thymic), Burkitt's lymphoma, and Burkitt's like high-grade B cell lymphoma; and unclassifiable low-grade or high-grade B cell lymphomas.

The pharmaceutical compositions of the present invention can also be used to treat subjects having the pre-malignant condition known as MGUS (monoclonal gammopathy of undetermined significance). Approximately 25% of patients with MGUS eventually develop multiple myeloma (MM) or a related plasma cell disorder (Kyle (1993) *Mayo Clinic. Proc.* 68:26-36). Proliferation of malignant plasma cells in the bone marrow, detection of a serum or urine monoclonal protein (M protein), anemia, hypercalcemia, renal insufficiency, and lytic bone lesions are clinical manifestations of MM, while MGUS is clinically recognized as the presence of M protein in the serum or urine without other clinical features of MM (see, for example, Kyle and Lust (1989) *Semin. Hematol.* 26:176-200; Greipp and Lust Stem Cells (1995) 13:10-21). MGUS patients are asymptomatic and have stable measurements of M protein (Kyle (1993) *Mayo Clinic. Proc.* 68:26-36). Once MGUS is identified in a subject, maintenance therapy with an appropriate pharmaceutical composition of the present invention, for example, a composition comprising an antagonist anti-CD40 antibody disclosed herein, may block the development of multiple myeloma in these subjects.

In particular, the pharmaceutical compositions of the invention are useful for treating B cell lymphomas, including those listed above, that are refractory to (i.e., resistant to, or have become resistant to) first-line oncotherapeutic treatments. The term "oncotherapeutic" is intended to mean a treatment for cancer such as chemotherapy, surgery, radiation therapy, single anti-cancer antibody therapy, and combinations thereof. Subpopulations of patients for whom treatment intervention with one or more anti-CD40 antibodies that modulates CD40L-mediated CD40 signaling, modulates ADCC, or both is desirable.

The pharmaceutical compositions of the present invention are also useful for treating non-B cell related hematological malignancies. Such malignances include, but are not limited to, acute leukemias; myeloblastic leukemias; acute myelocytic leukemias; promyelocytic leukemia; myelomonocytic leukemia; monocytic leukemia; erythroleukemia; granulocytic leukemia (chronic myelocytic leukemia); polycythemia vera; and the like.

Solid tumors that comprise CD40-expressing neoplastic cells, and thus beneficially respond to treatment with the pharmaceutical compositions of the present invention, include, but are not limited to, ovarian, lung (for example, non-small cell lung cancer of the squamous cell carcinoma, adenocarcinoma, and large cell carcinoma types, and small cell lung cancer), breast, colon, kidney (including, for example, renal cell carcinomas), bladder, liver (including, for example, hepatocellular carcinomas), gastric, cervical, prostate, nasopharyngeal, thyroid (for example, thyroid papillary carcinoma), skin cancers such as melanoma, and sarcomas, including, for example, osteosarcomas and Ewing's sarcomas.

Beneficial results that can be achieved by administering a pharmaceutical composition of the invention to a subject with a cancer or pre-malignant condition include any positive therapeutic response with respect to that cancer or condition. By "positive therapeutic response" in the context of cancer treatment is intended an improvement in the disease in association with the anti-tumor activity of the anti-CD40 therapeutic agent and/or an improvement in the symptoms associated with the disease of interest. That is, an anti-proliferative effect, the prevention of further tumor outgrowths, a reduction in tumor size, a reduction in the number of cancer cells, and/or a decrease in one or more symptoms mediated by stimulation of CD40-expressing cells can be observed. Thus, for example, a positive therapeutic response would refer to one or more of the following improvements in the disease: (1) a reduction in tumor size; (2) a reduction in the number of cancer (i.e., neoplastic) cells; (3) an increase in neoplastic cell death; (4) inhibition of neoplastic cell survival; (4) inhibition (i.e., slowing to some extent, preferably halting) of tumor growth; (5) inhibition (i.e., slowing to some extent, preferably halting) of cancer cell infiltration into peripheral organs; (6) inhibition (i.e., slowing to some extent, preferably halting) of tumor metastasis; (7) the prevention of further tumor outgrowths; (8) an increased patient survival rate; and (9) some extent of relief from one or more symptoms associated with the cancer. Positive therapeutic responses in any given malignancy can be determined by standardized response criteria specific to that malignancy. Tumor response can be assessed for changes in tumor morphology (i.e., overall tumor burden, tumor size, and the like) using screening techniques such as magnetic resonance imaging (MRI) scan, x-radiographic imaging, computed tomographic (CT) scan, bone scan imaging, endoscopy, and tumor biopsy sampling including bone marrow aspiration (BMA) and counting of tumor cells in the circulation. In addition to these positive therapeutic responses, the subject undergoing therapy with the antagonist anti-CD40 antibody-containing pharmaceutical composition of the invention may experience the beneficial effect of an improvement in the symptoms associated with the disease. Thus for B cell tumors, the subject may experience a decrease in the so-called B symptoms, i.e., night sweats, fever, weight loss, and/or urticaria. For pre-malignant conditions, therapy with an anti-CD40 therapeutic agent may block and/or prolong the time before development of a related malignant condition, for example, development of multiple myeloma in subjects suffering from monoclonal gammopathy of undetermined significance (MGUS).

By "anti-inflammatory activity" is intended a reduction or prevention of inflammation. Therapy with an antagonist anti-CD40 antibody-containing liquid pharmaceutical composition of the invention causes a physiological response that is beneficial with respect to treatment of an autoimmune disease and/or inflammatory disease, where the disease involves cells expressing the CD40 antigen. It is recognized that the compositions of the invention may be useful in preventing phenotypic change in cells such as proliferation, activation, and the like.

The subject who is undergoing treatment intervention with an antagonist anti-CD40 antibody-containing liquid pharmaceutical composition of the invention can be afflicted with, or at risk of developing or relapsing with, any inflammatory or autoimmune disease that is mediated by CD40 signaling on CD40-expressing cells. Inflammatory diseases are characterized by inflammation and tissue destruction, or a combination thereof. "Inflammatory disease" includes any inflammatory immune-mediated process where the initiating event or target of the immune response involves non-self antigen(s), including, for example, alloantigens, xenoantigens, viral antigens, bacterial antigens, unknown antigens, or allergens.

Further, for purposes of the present invention, the term "inflammatory disease(s)" includes "autoimmune disease(s)." As used herein, the term "autoimmunity" is generally understood to encompass inflammatory immune-mediated processes involving "self" antigens. In autoimmune diseases, self antigen(s) trigger host immune responses.

Also, the pharmaceutical compositions of the present invention can be used for treatment of inflammation associated with tissue transplant rejection. "Transplant rejection" or "graft rejection" refers to any host-mounted immune response against a graft including but not limited to HLA antigens, blood group antigens, and the like.

The pharmaceutical compositions of the invention can also be used for treatment of graft versus host disease, such as that associated with bone marrow transplantation, for example. In such graft versus host disease, the donor bone marrow includes lymphocytes and cells that mature into lymphocytes. The donor's lymphocytes recognize the recipient's antigens as non-self and mount an inflammatory immune response. Hence, as used herein, "graft versus host disease" or "graft versus host reaction" refers to any T cell mediated immune response in which donor lymphocytes react to the host's antigens.

Examples of autoimmune and/or inflammatory disorders include, but are not limited to, systemic lupus erythematosus (SLE), discoid lupus, lupus nephritis, sarcoidosis, inflammatory arthritis, including juvenile arthritis, rheumatoid arthritis, psoriatic arthritis, Reiter's syndrome, ankylosing spondylitis, and gouty arthritis, rejection of an organ or tissue transplant, hyperacute, acute, or chronic rejection and/or graft versus host disease, multiple sclerosis, hyper IgE syndrome, polyarteritis nodosa, primary biliary cirrhosis, inflammatory bowel disease, Crohn's disease, celiac's disease (gluten-sensitive enteropathy), autoimmune hepatitis, pernicious anemia, autoimmune hemolytic anemia, psoriasis, scleroderma, myasthenia gravis, autoimmune thrombocytopenic purpura, autoimmune thyroiditis, Grave's disease, Hasimoto's thyroiditis, immune complex disease, chronic fatigue immune dysfunction syndrome (CFIDS), polymyositis and dermatomyositis, cryoglobulinemia, thrombolysis, cardiomyopathy, pemphigus vulgaris, pulmonary interstitial fibrosis, Type I and Type II diabetes mellitus, type 1, 2, 3, and 4 delayed-type hypersensitivity, allergy or allergic disorders, unwanted/unintended immune responses to therapeutic proteins (see for example, U.S. Patent Application No. US 2002/0119151 and Koren, et al. (2002) Curr. Pharm. Biotechnol. 3:349-60), asthma, Churg-Strauss syndrome (allergic granulomatosis), atopic dermatitis, allergic and irritant contact dermatitis, urtecaria, IgE-mediated allergy, atherosclerosis, vasculitis, idiopathic inflammatory myopathies, hemolytic disease, Alzheimer's disease, chronic inflammatory demyelinating polyneuropathy, and the like. In some other embodiments, the pharmaceutical compositions of the present invention are used to treat individuals for pulmonary inflammation, including, but not limited to, lung graft rejection, asthma, sarcoidosis, emphysema, cystic fibrosis, idiopathic pulmonary fibrosis, chronic bronchitis, allergic rhinitis and allergic diseases of the lung such as hypersensitivity pneumonitis, eosinophilic pneumonia, bronchiolitis obliterans due to bone marrow and/or lung transplantation or other causes, graft atherosclerosis/graft phlebosclerosis, as well as pulmonary fibrosis resulting from collagen, vascular, and autoimmune diseases such as rheumatoid arthritis and lupus erythematosus.

In other embodiments, the pharmaceutical compositions of the present invention are useful for treating autoimmune diseases and inflammatory diseases that are initially resistant to, or which develop resistance to other known therapeutic treatments whose mode of action is other than through modulation of CD40L-mediated CD40 signaling, modulation of ADCC, or both. The pharmaceutical compositions of the invention can be used to treat subpopulations of patients for whom treatment intervention with one or more antagonist anti-CD40 antibodies that modulates CD40L-mediated CD40 signaling, modulates ADCC, or both is desirable.

Beneficial results that can be achieved by administering the pharmaceutical compositions of the invention to a subject with an inflammatory disease or autoimmune disease include any positive therapeutic response with respect to that disease. By "positive therapeutic response" in the context of an autoimmune disease and/or inflammatory disease is intended an improvement in the disease in association with the anti-inflammatory activity of these antibodies or antigen-binding fragments thereof, and/or an improvement in the symptoms associated with the disease. That is, an anti-proliferative effect, the prevention of further proliferation of the CD40-expressing cell, a reduction in the inflammatory response including but not limited to reduced secretion of inflammatory cytokines, adhesion molecules, proteases, immunoglobulins (in instances where the CD40 bearing cell is a B cell), combinations thereof, and the like, increased production of anti-inflammatory proteins, a reduction in the number of autoreactive cells, an increase in immune tolerance, inhibition of autoreactive cell survival, and/or a decrease in one or more symptoms mediated by stimulation of CD40-expressing cells can be observed. Such positive therapeutic responses are not limited to the route of administration and may comprise administration to the donor, the donor tissue (such as for example organ perfusion), the host, any combination thereof, and the like.

Clinical response can be assessed using screening techniques such as magnetic resonance imaging (MRI) scan, x-radiographic imaging, computed tomographic (CT) scan, flow cytometry or fluorescence-activated cell sorter (FACS) analysis, histology, gross pathology, and blood chemistry, including but not limited to changes detectable by ELISA, RIA, chromatography, and the like. In addition to these positive therapeutic responses, the subject undergoing therapy with an antagonist anti-CD40 antibody-containing liquid pharmaceutical composition of the invention may experience the beneficial effect of an improvement in the symptoms associated with the disease.

The following examples are offered by way of illustration and not by way of limitation.

EXPERIMENTAL

CHIR-122.12 is a fully humanized anti-CD40 IgG1 monoclonal antibody produced by a CHO cell culture process. The molecule has a molecular weight of 150 kDa, and the molecular structure consists of two heavy chains and two light chains linked together by disulfide bonds. CHIR-12.12 targets the human CD40 cell-surface receptor protein. It is a strong antagonist and inhibits in vitro CD40 ligand-mediated proliferation of normal B cells, as well as inhibiting in vitro CD40 ligand-mediated proliferation of cancer cells from NHL and CLL patients. Hybridoma line 153.8E2.D10.D6.12.12 (CMCC#12056) expressing the CHIR-12.12 antibody has been deposited with the American Type Culture Collection [ATCC; 10801 University Blvd., Manassas, Va. 20110-2209 (USA)] on Sep. 17, 2003, under Patent Deposit Number PTA-5543.

Without being bound by theory, the CHIR-12.12 antibody is a dual action antagonist anti-CD40 monoclonal antibody having a unique combination of attributes. This fully human monoclonal antibody blocks CD40L-mediated CD40 signaling pathways for survival and proliferation of B cells; this antagonism leads to ultimate cell death. CHIR-12.12 also mediates recognition and binding by effector cells, initiating antibody dependent cellular cytotoxicity (ADCC). Once CHIR-12.12 is bound to effector cells, cytolytic enzymes are released, leading to B-cell apoptosis and lysis.

For a more detailed description of the biological activities of CHIR-12.12, and the assays used to measure them, see provisional applications entitled "Antagonist Anti-CD40 Monoclonal Antibodies and Methods for Their Use," filed Nov. 4, 2003, Nov. 26, 2003, and Apr. 27, 2004, and assigned U.S. Patent Application Nos. 60/517,337, 60/525,579, and 60/565,710, respectively, and International Patent Application No. PCT/US2004/037152, also entitled "Antagonist Anti-CD40 Monoclonal Antibodies and Methods for Their Use," filed Nov. 4, 2004, and published as WO 2005/044854; the contents of each of which are herein incorporated by reference in their entirety. See also International Publication Nos. WO 2005/044304, WO 2005/044305, WO 2005/044306, WO 2005/044855, WO 2005/044307, and WO 2005/044294; the contents of each of which are herein incorporated by reference in their entirety. See also the assays described in provisional application entitled "Methods for Diagnosis and Treatment of Proliferative Disorders Mediated by CD40 Signaling," filed Dec. 9, 2005, and assigned U.S. Patent Application No. 60/749,285, and corresponding International Patent Application No. PCT/US2006/019414, filed May 18, 2006, and published as WO 2006/125143; and provisional application entitled "Methods for Diagnosis and Treatment of Diseases Having an Autoimmune and/or Inflammatory Component," filed Dec. 9, 2005, and assigned U.S. Patent Application No. 60/749,336, and corresponding International Patent Application No., filed May 18, 2006, and published as WO 2006/125117; the contents of each of which are herein incorporated by reference in their entirety.

The primary clinical applications of CHIR-12.12 are treatment of B-cell related malignancies, including chronic lymphocytic leukemia (CLL), multiple myeloma (MM), and non-Hodgkin's lymphoma (NHL), and autoimmune and/or inflammatory diseases associated with CD40-expressing cells. The CHIR-12.12 drug product for clinical trials is formulated at 20 mg/ml CHIR-12.12 antibody in a liquid formulation. The following studies were undertaken to determine optimal buffer, isotonizing agent, and various excipients for stabilizing the antibody in the liquid formulation.

Example 1

Effect of Various Buffer Species and Methionine on Stabilization of CHIR-12.12

Solution conditions (e.g., pH, buffer species, and ionic strength) and excipients (e.g., surfactants and stabilizers) are critical factors for stability of a protein in liquid formulation. Physicochemical stability of CHIR-12.12 is optimal at pH 5.5. However, CHIR-12.12 protein can degrade via aggregation and fragmentation under unfavorable solution conditions; it can also oxidize, especially in the presence of peroxide impurities and/or trace amounts of metals introduced with raw excipient materials such as Tween. The following experiments were conducted to identify the best buffer species and appropriate excipients to stabilize CHIR-12.12 monoclonal antibody against aggregation, fragmentation, and oxidation when formulated at the optimum pH 5.5.

Materials

The CHIR-12.12 drug substance (DS) lots for the study were CHO-derived purified bulk lot # CD021105A and lot # PD010705A. The DS lots were produced at Xoma, Ltd (Berkeley, Calif.). The formulation samples for this study were prepared by dialysis of the DS against respective buffer solutions followed by spiking with the desired amount of Tween. The concentration of CHIR-12.12 protein in all the samples was approximately 20 mg/ml.

Analytical Methods

Size-Exclusion Chromatography (SEC).

SEC-HPLC separates molecules in order of decreasing molecular weight. Consequently, CHIR-12.12 aggregates are the first to elute from the HPLC column, followed by the monomer, with the fragments eluting last. Purity, aggregation, and fragmentation of CHIR-12.12 were analyzed by a Waters Alliance HPLC using Tosohaas TSK-GEL 3000SW$_{XI}$ column, 50 mM sodium phosphate, 200 mM NaCl, pH 7.0 as mobile phase at a flow rate of 0.7 mL/min.

Hydrophobic Interaction Chromatography (HIC).

Oxidation of CHIR-12.12 was measured using a Waters Alliance HPLC system with a Tosoh TSK gel butyl-NPR column, 2 M ammonium sulfate/20 mM Tris, pH 7.0 as mobile phase A and 20 mM Tris, pH 7.0 as mobile phase B at a flow rate of 1.0 ml/min. CHIR-12.12 antibody is digested with papain to yield Fab and Fc fragments. The oxidation products of CHIR-12.12 are oxidized Fc fragments (metSO), which are pre-Fc species eluting between the main Fab species and the main Fc species from the HPLC column.

Experiments and Results

Stabilization Effect of Citrate Buffer on Aggregation and Fragmentation.

CHIR-12.12 from DS lot #PD010705A was formulated at 20 mg/ml in 10 mM citrate, acetate, succinate, or phosphate buffer solution with 150 mM NaCl, 0.1% (w/v) Tween 80 and pH 5.5. The formulation samples were filled as 1.2 ml solutions into 3 cc glass vials and stored at 5° C., 25° C., and 40° C. The CHIR-12.12 stability samples were analyzed at designated time points by SEC assay.

Figure 2:
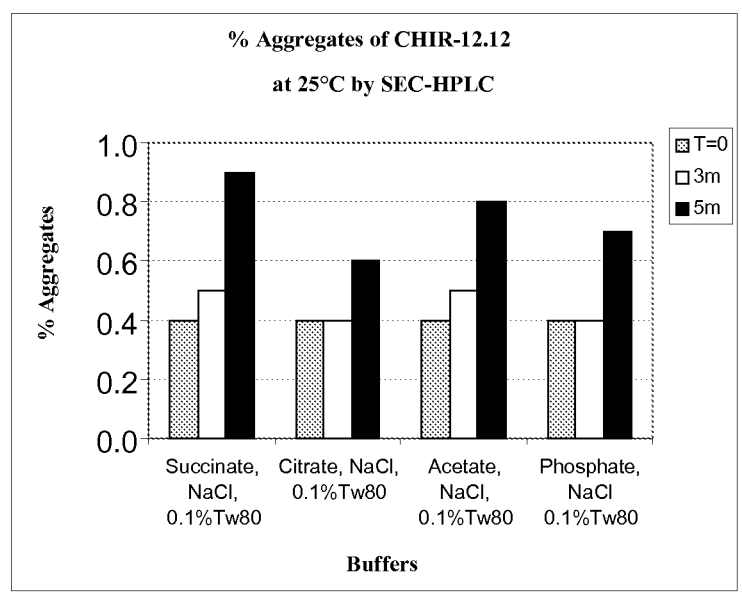
FIG. 2 shows the effect of buffer species on aggregate formation of mAb CHIR-12.12 within the various antibody formulations stored at 25° C. for 3 months or 5 months, as measured by SEC-HPLC analysis.
Figure 3:
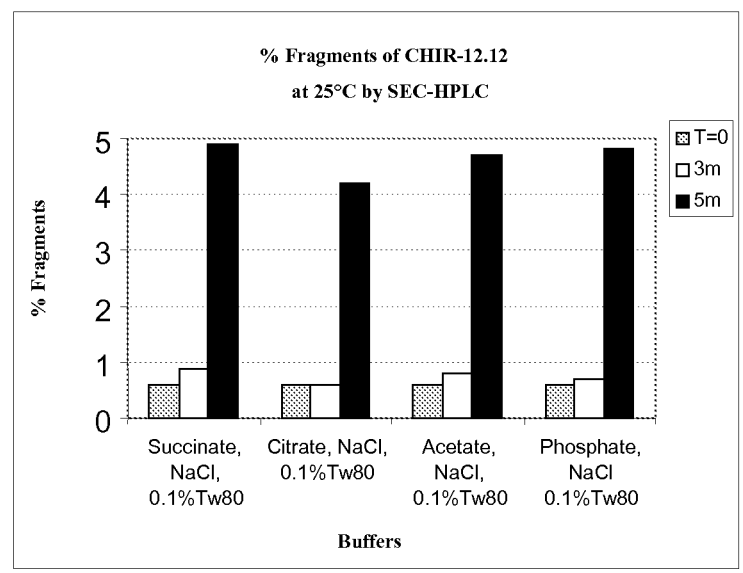
FIG. 3 shows the effect of buffer species on fragmentation of mAb CHIR-12.12 within the various antibody formulations stored at 25° C. for 3 months or 5 months, as measured by SEC-HPLC analysis.
Figure 4:
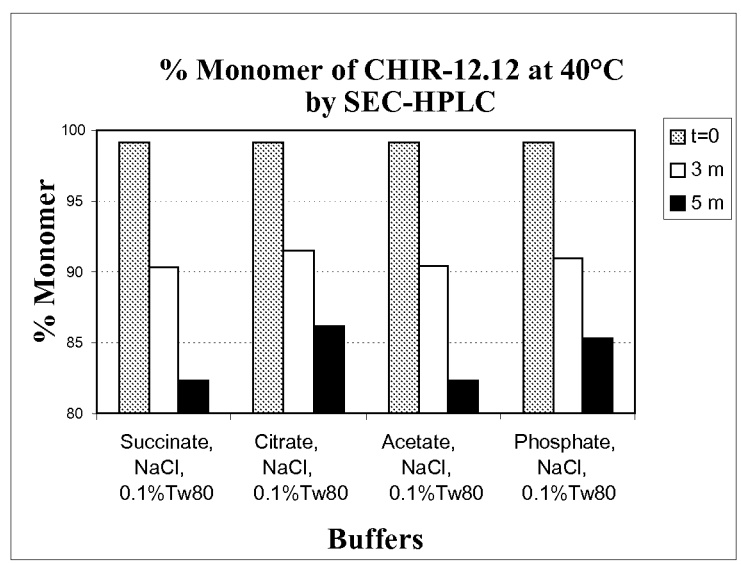
FIG. 4 shows the effect of buffer species on purity of mAb CHIR-12.12 formulations stored at 40° C. for 3 months or 5 months as measured by SEC-HPLC analysis.
Figure 5:
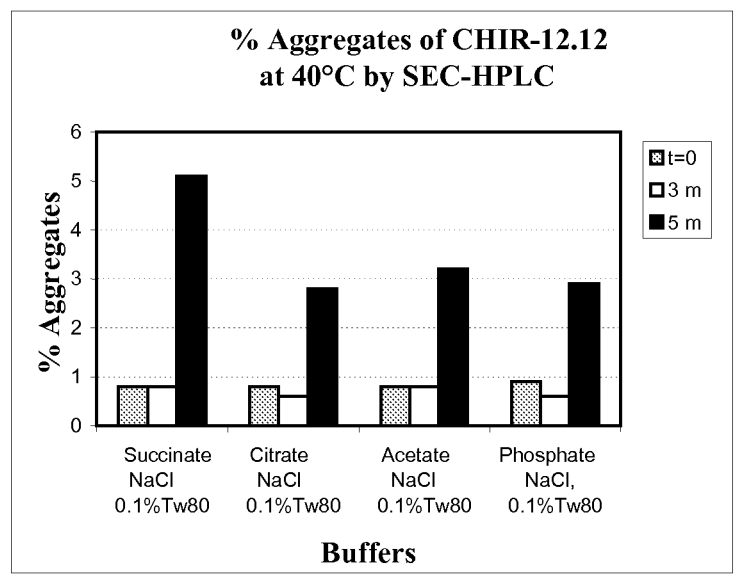
FIG. 5 shows the effect of buffer species on aggregate formation of mAb CHIR-12.12 within the various antibody formulations stored at 40° C. for 3 months or 5 months, as measured by SEC-HPLC analysis.
Figure 6:
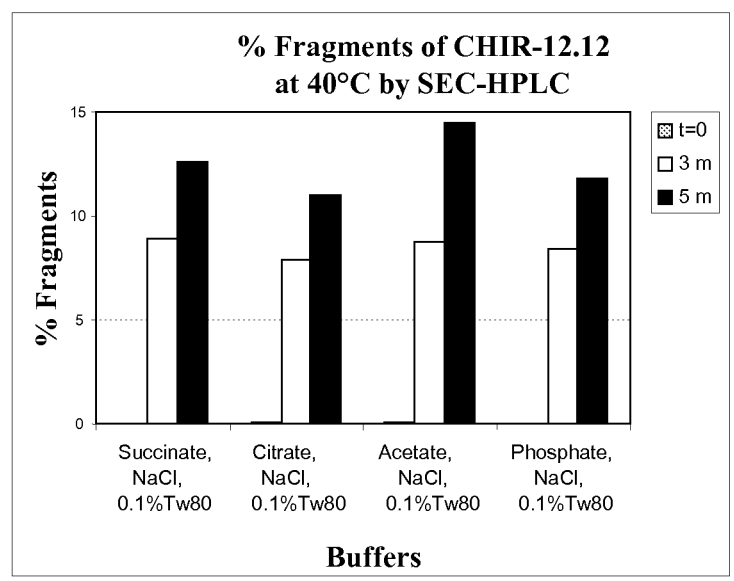
FIG. 6 shows the effect of buffer species on fragmentation of mAb CHIR-12.12 within the various antibody formulations stored at 40° C. for 3 months or 5 months, as measured by SEC-HPLC analysis.

FIGS. 1-3 show the SEC analysis for purity, aggregates, and fragments, respectively, in the samples stored at 25° C. FIGS. 4-6 summarize the SEC analysis for purity, aggregates, and fragments, respectively, in the samples stored at 40° C. All the results show that the citrate-based formulation samples remained at the highest purity and lowest aggregation and fragmentation levels among the four formulations tested. Although there was little change detected for the samples stored at 5° C. through 5 months (data not shown), the accelerated SEC data predicts that citrate buffer will likely be superior to the other three commonly used buffer species in improving the long-term real-time stability of CHIR-12.12 against aggregation and fragmentation.

Oxidation Inhibition Effect of Citrate Buffer on CHIR-12.12.

The CHIR-12.12 stability samples were prepared in citrate, acetate, and succinate buffers with 0.1% and 0.2% (w/v) Tween 80. The samples were stored at 5° C., 25° C., and 40° C. and analyzed by Hydrophobic Interaction Chromatography (HIC) for oxidation at the predetermined time points. The oxidation products of CHIR-12.12 were measured as a percentage of sums of the Pre-Fc peak species, i.e., Pre-Fc %. The results in Table 1 show that the citrate-based formulation generated fewer oxidation products than the succinate- and acetate-buffered formulations, indicating that the citrate buffer minimized the oxidation of CHIR-12.12. These results suggest that citric acid probably served as a chelating agent to inhibit trace-metal-induced oxidation of CHIR-12.12 protein.

The SEC and HIC analyses indicate that citrate buffer is superior to succinate, acetate, and phosphate buffer species in protecting CHIR-12.12 from aggregation and fragmentation. Citrate buffer is also superior to succinate and acetate buffers as it minimizes oxidation of CHIR-12.12 protein.

TABLE 1

Effect of buffer species on oxidation of CHIR-12.12 (20 mg/ml) as measured by HIC assay.

| Formulation Buffer with Tween 80 | | 10 mM Citrate 150 mM NaCl | 10 mM Acetate 150 mM NaCl | 10 mM Succinate 150 mM NaCl |
|---|---|---|---|---|
| Tween 80 Concentration | Storage | pH 5.5 Pre-Fc % | pH 5.5 Pre-Fc % | pH 5.5 Pre-Fc % |
| 0.1% (w/v) | 5° C., 5 mo | 0.0 | 0.0 | 0.0 |
|  | 25° C., 5 mo | 2.6 | 7.1 | 9.4 |
|  | 40° C., 3 mo | 5.6 | N/D* | 13.5 |
| 0.2% (w/v) | 5° C., 5 mo | 0.0 | 0.0 | N/D |
|  | 5° C., 8 mo | 2.0 | 2.0 | 2.2 |
|  | 25° C., 5 mo | 3.0 | 10.7 | 11.5 |
|  | 25° C., 8 mo | 4.8 | 18.1 | 19.4 |
|  | 40° C., 3 mo | 7.7 | N/D | 16.0 |

*N/D, not determined.

Oxidation Inhibition Effect of L-Methionine on CHIR-12.12.

DS lot #CD021105A was formulated at 20 mg/ml in 10 mM sodium citrate/citric acid, 150 mM NaCl, 0.1% Tween 80 or Tween 20 as well as various amount (0-5 mM) of L-methionine. The formulation samples were filled at 2.5 ml into 3 cc vials and stored at 40° C. Table 2 shows HIC results for the samples at initial time and at 40° C. for 3 months. At initial time, the oxidation of CHIR-12.12 in all the formulations was comparable to the original bulk drug substance (DS) lot # CD 021105A. The oxidation levels in the formulations without L-methionine were more than doubled upon storage at 40° C. for 3 months. However, the oxidation level in the formulations containing L-methionine had little change throughout 3 months storage at 40° C.

The results indicate that 5 mM L-methionine was effective and sufficient in preventing the oxidation of CHIR-12.12 under the highly stressed storage conditions. The oxidation inhibition effect of L-methionine on CHIR-12.12 was confirmed by Lyc-peptide map.

TABLE 2

Inhibition effect of L-methionine on CHIR-12.12 oxidation.

|  | Pre-Fc % | |
|---|---|---|
| Formulations with 20 mg/ml CHIR-12.12 | Time 0 | 3 mos at 40° C. |
| Bulk CHIR-12.12 DS lot# CD 021105A | 1.7 | N/D* |
| 10 mM sodium citrate/citric acid, 150 mM NaCl, 0.1% Tween-80, pH 5.5 | 1.6 | 4.2 |
| 10 mM sodium citrate/citric acid, 150 mM NaCl, 0.1% Tween-80, 2 mM L-methionine, pH 5.5 | 1.6 | 1.6 |
| 10 mM sodium citrate/citric acid, 150 mM NaCl, 0.1% Tween-20, pH 5.5 | 1.7 | 3.9 |
| 10 mM sodium citrate/citric acid, 150 mM NaCl, 0.1% Tween-20, 2 mM L-methionine, pH 5.5 | 1.5 | 1.1 |
| 10 mM sodium citrate/citric acid, 150 mM NaCl, 0.1% Tween-20, 5 mM L-methionine, pH 5.5 | 1.5 | 1.2 |

*N/D, not determined.

In summary, citrate buffer minimizes aggregation, fragmentation, and oxidation of CHIR-12.12, and therefore represents an optimal buffer for a CHIR-12.12 liquid formulation. L-methionine effectively inhibits oxidation of CHIR-12.12, with 5 mM L-methionine being preferred.

Example 2

Stabilizing Effect of Arginine-HCl on CHIR-12.12

The following study was aimed at selecting a tonicifying agent and stabilizer for long-term storage stability of CHIR-12.12 formulated as a liquid pharmaceutical composition intended for administration via intravenous infusion. Although NaCl is the most commonly used isotonizing agent for protein parenteral products, it may not have optimal stabilizing effects on antibody therapeutics. This study reports on the comparative stabilizing effects of sodium chloride and the acidic form of arginine (arginine-HCl) on CHIR-12.12 in an aqueous formation.

The CHIR-12.12 bulk antibody drug substance was formulated with a citrate buffer at pH 5.5, employing either 150 mM NaCl or 150 mM L-arginine-HCl to achieve the target osmolality of 295 mOsm/kg for the CHIR-12.12 liquid formulation. Differential Scanning Calorimetry (DSC), size-exclusion chromatograph (SEC-HPLC), SDS-PAGE, and Cation-Exchange HPLC (CIEX-HPLC) were used to evaluate biophysical and/or biochemical stability of the CHIR-12.12 antibody. The study demonstrates that 150 mM L-arginine-HCl not only renders isotonicity to a CHIR-12.12 aqueous formulation, but also increases the conformational stability of CHIR-12.12 against aggregation, fragmentation, and deamidation. L-arginine-HCl proved to be superior to NaCl under accelerated stability conditions. Furthermore, the accelerated stability data predict a longer shelf-life for the CHIR-12.12 L-arginine-HCl formulation.

Materials

The CHIR-12.12 drug substance (DS) used for this study was a CHO-derived purified bulk lot # CD021105A. The DS lot was produced at Xoma Ltd. (Berkeley, Calif.).

CHIR-12.12 from the DS lot was used in the following formulations:

Formulation 1: 20 mg/ml CHIR-12.12, 10 mM sodium citrate/citric acid, 150 mM NaCl, 0.1% Tween 80, and pH 5.5

Formulation 2: 20 mg/ml CHIR-12.12, 10 mM sodium citrate/citric acid, 150 mM L-arginine-HCl, 0.1% Tween 80, and pH 5.5

Analytical Methods

Differential Scanning Calorimetry (DSC).

Conformational stability of the CHIR-12.12 formulation samples was evaluated using a MicroCal VP-DSC upon heating 15° C. to 90° C. at 1° C./min.

Size Exclusion Chromatography (SEC-HPLC).

Purity, aggregation, and fragmentation of CHIR-12.12 were analyzed by a Waters Alliance RPLC with a Tosohaas TSK-GEL 3000SW$_{XL}$ column, 50 mM sodium, phosphate, 200 mM NaCl, pH 7.0 as mobile phase at a flow Rate of 0.7 ml/min.

SDS PAGE (Non-Reduced and Reduced).

Purity of CHIR-12.12 was also evaluated using 12% Tris-Glycine gels under non-reducing and reducing conditions. The protein was detected by Coomassie blue staining.

Cation Exchange Chromatography (CIEX-HPLC).

Charge change-related deamidation of CHIR-12.12 was measured using a Waters Alliance HPLC system with a Dionex Propac WCX-10 column, 50 mM HEPES, pH 7.3 as mobile phase A and 50 mM HEPES containing 500 mM NaCl, pH 7.3 as mobile phase B at a flow rate of 0.8 ml/min.

The following is a key to the abbreviations in the figures referred to in the results section herein below:

Succinate, NaCl, 0.1% TW80=10 mM sodium succinate/succinic acid buffer, 150 mM NaCl, 0.1% Tween 80, pH 5.5

Citrate, NaCl, 0.1% Tw80=10 mM sodium citrate/citric acid buffer, 150 mM NaCl, 0.1% Tween 80, pH 5.5

Acetate, NaCl, 0.1% Tw80=10 mM sodium acetate/acetic acid buffer, 150 mM NaCl, 0.1% Tween 80, pH 5.5

Phos, NaCl, 0.1% Tw80=10 mM sodium phosphate dibasic/sodium phosphate monobasic buffer, 150 mM NaCl, 0.1% Tween 80, pH 5.5

Citrate, Arg, 0.1% Tw80=10 mM sodium citrate/citric acid buffer, 150 mM L-arginine-HCl, 0.1% Tween 80, pH 5.5

Results

Differential Scanning Calorimetry (DSC).

Figure 7:
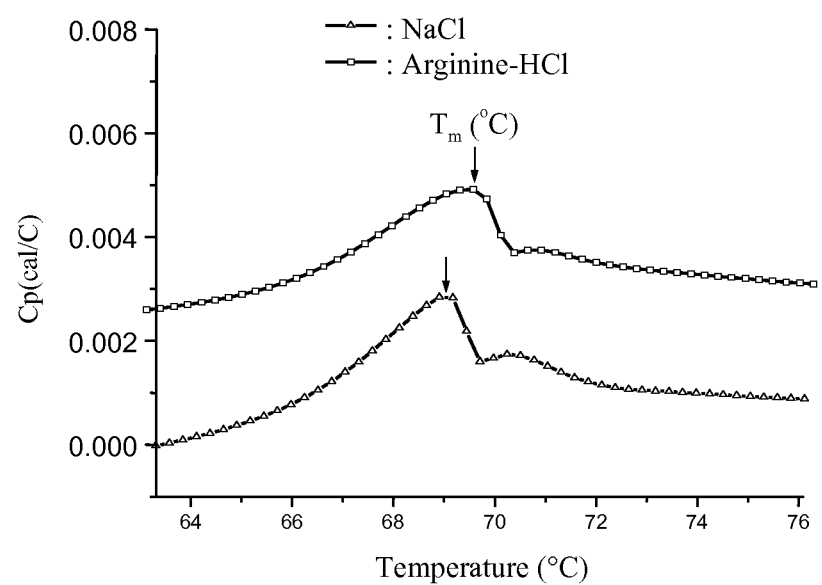
FIG. 7 shows differential scanning calorimetry thermograms for mAb CHIR-12.12 in the formulations containing either NaCl or L-arginine-HCl as the isotonizing agent.

FIG. 7 shows DSC theograms for CHIR 12.12 in the two formulations as described in the "Materials" section above. Thermal unfolding of CHIR-12.12 exhibited at least two thermal transitions, probably representing unfolding/melting of the Fab and the Fc domains, respectively. At higher temperature, the proteins presumably aggregated, resulting in loss of DSC signal. In this study, the lowest thermal transition temperature was defined as the melting temperature, $T_m$. The L-arginine-HCl-containing formulation exhibited a higher $T_m$ than the NaCl-containing formulation, suggesting that L-arginine-HCl provides CHIR-12.12 with higher conformational stability than does NaCl.

SEC-HPLC Analysis.

Figure 8:
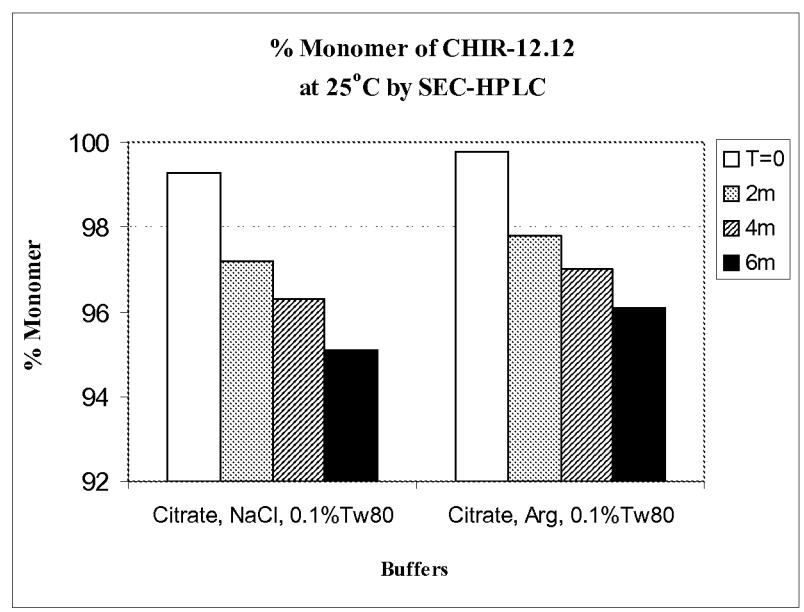
FIG. 8 shows % monomer form of mAb CHIR-12.12 remaining in formulations containing either NaCl or L-arginine-HCl as the isotonizing agent when stored at 25° C. for 2, 4, or 6 months, as measured by SEC-HPLC.
Figure 9:
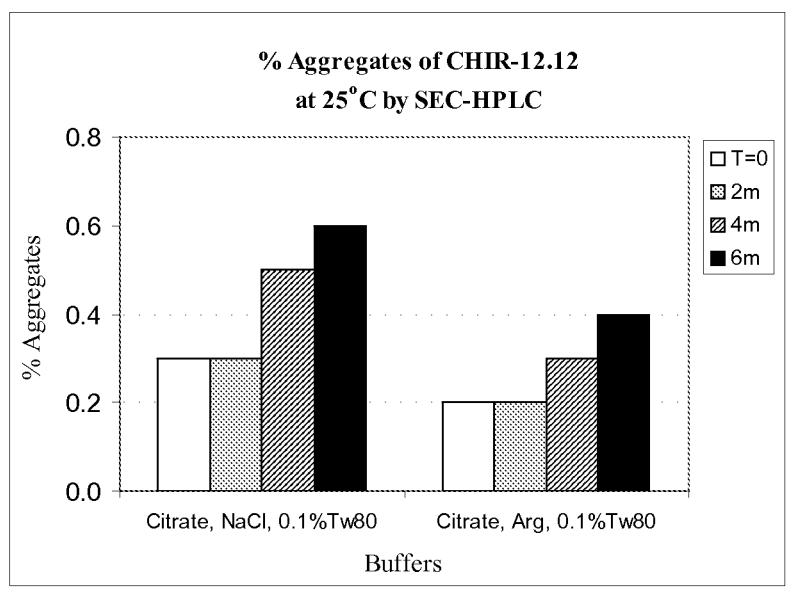
FIG. 9 shows % aggregates of mAb CHIR-12.12 in formulations containing either NaCl or L-arginine-HCl as the isotonizing agent when stored at 25° C. for 2, 4, or 6 months, as measured by SEC-HPLC.
Figure 10:
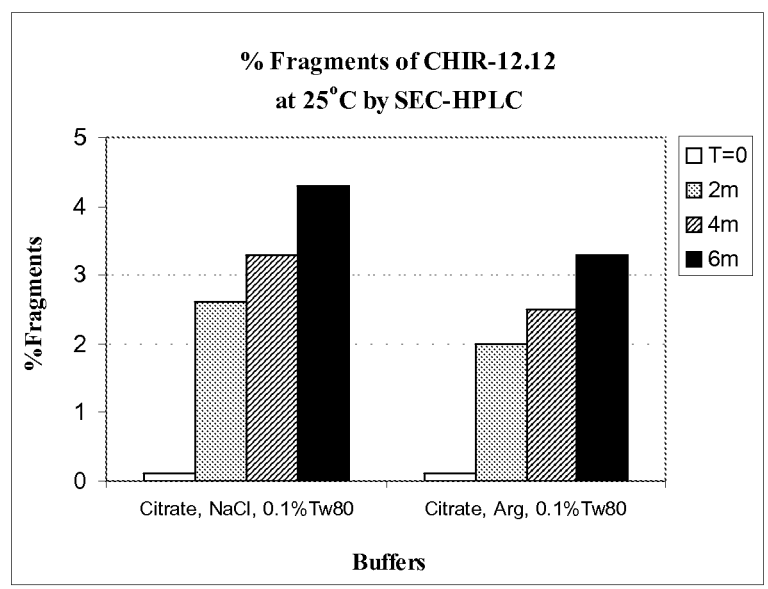
FIG. 10 shows % fragments of mAb CHIR-12.12 in formulations containing either NaCl or L-arginine-HCl as the isotonizing agent when stored at 25° C. for 2, 4, or 6 months, as measured by SEC-HPLC.
Figure 11:
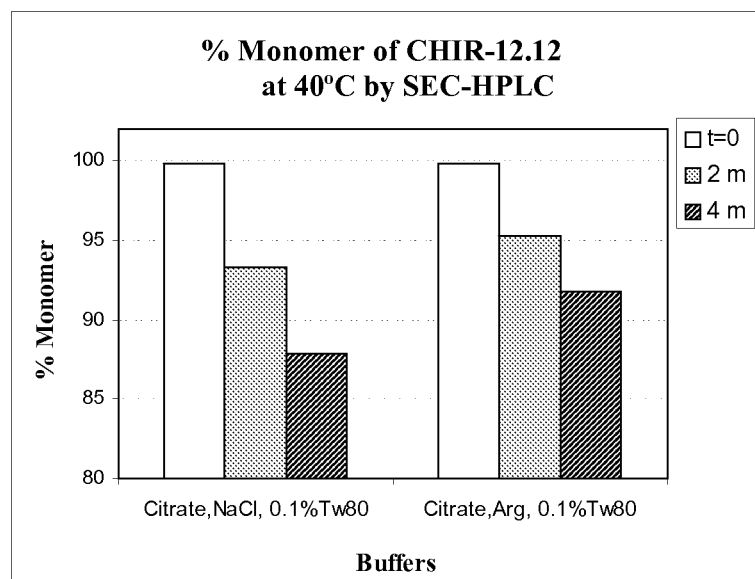
FIG. 11 shows % monomer form of mAb CHIR-12.12 remaining in formulations containing either NaCl or L-arginine-HCl as the isotonizing agent when stored at 40° C. for 2 or 4 months, as measured by SEC-HPLC.
Figure 12:
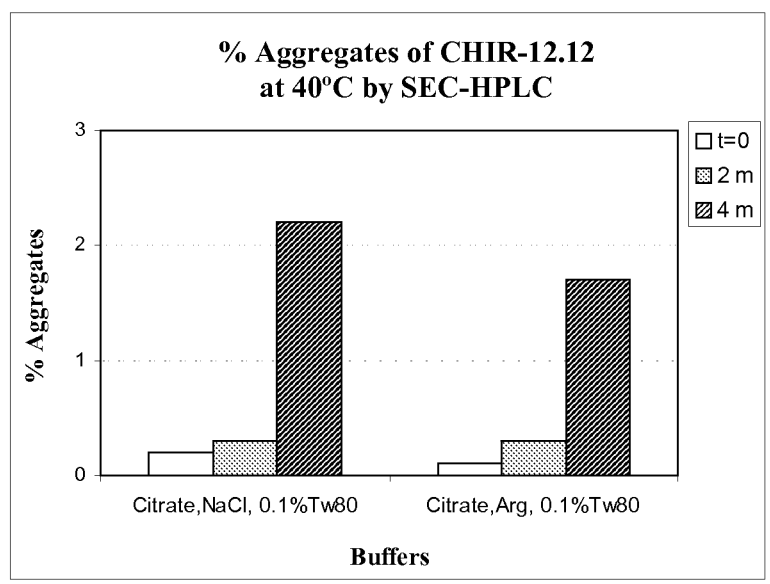
FIG. 12 shows % aggregates of mAb CHIR-12.12 in formulations containing either NaCl or L-arginine-HCl as the isotonizing agent when stored at 40° C. for 2 or 4 months, as measured by SEC-HPLC.
Figure 13:
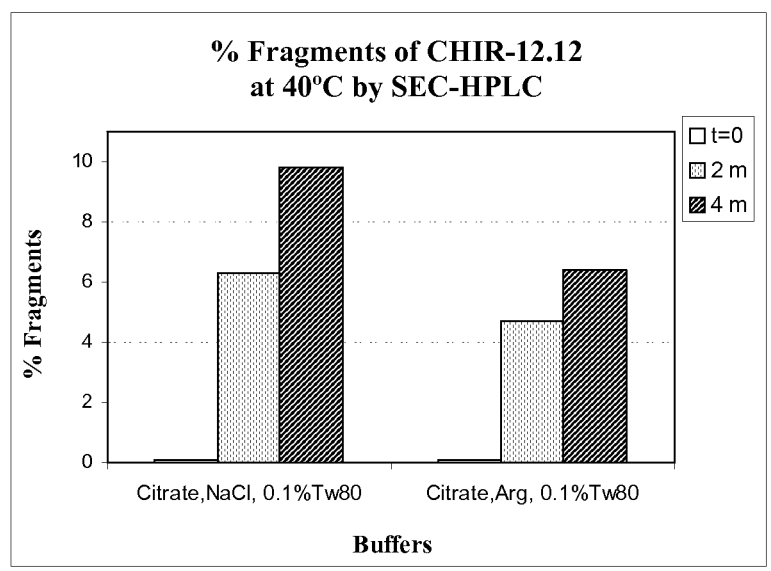
FIG. 13 shows % fragments of mAb CHIR-12.12 in formulations containing either NaCl or L-arginine-HCl as the isotonizing agent when stored at 40° C. for 2 or 4 months, as measured by SEC-HPLC.

After incubation at 5° C. through 6 months, SEC-HPLC detected negligible amounts of protein aggregates and fragments (<0.5%) in the L-arginine-HCl- and NaCl-containing formulations and no appreciable stability difference between the two formulations (data not shown). Under accelerated storage conditions, i.e., 25° C. for 6 months, the L-arginine-HCl-containing formulation contained a higher percentage of monomer, as shown in FIG. 8. At the expense of the monomer, the content of both aggregates and fragments slowly increased with storage time. However, the L-arginine-HCl-containing formulation generated less aggregates and fragments than the NaCl-containing formulation as shown in FIGS. 9 and 10, respectively. Similarly, when stored at 40° C., the L-arginine-HCl-containing formulation exhibited a higher percentage of monomer and lower percentages of aggregates and fragments than did the NaCl-containing formulation, as shown in FIGS. 11, 12, and 13, respectively. Upon storage at 40° C. for 4 months, the L-arginine-HCl-containing formulation had 91.8% monomer remaining, 1.7% aggregates, and 6.5% fragments, while the NaCl-containing formulation had 87.9% monomer, 2.2% aggregates, and 9.9% fragments. The SEC-HPLC results demonstrate L-arginine-HCl improves the stability of CHIR-12.12 protein in comparison with NaCl.

SDS-PAGE (Non-Reduced and Reduced).

Table 3 presents SDS-PAGE results for the L-arginine-HCl- and NaCl-containing formulations analyzed under non-reduced (NR) and reduced (R) conditions. The purity of CHIR-12.12 was measured as a percentage of the main band under non-reduced conditions or as a percentage of the sum of the heavy and light chain bands under reduced conditions. Except at time 0, the L-arginine-HCl-containing formulation showed higher purity than did the NaCl-containing formulation under both non-reduced and reduced conditions. The observation from SDS-PAGE was consistent with SEC-HPLC results in that L-arginine-HCl increased the stability of CHIR-12.12 over NaCl.

TABLE 3

Comparison of L-arginine-HCl and NaCl by SDS-PAGE analysis.

| Formulation with 20 mg/ml CHIR-12.12 | T = 0 | | 4 mo at 25° C. | | 4 mo at 40° C. | | 6 mo at 25° C. | |
|---|---|---|---|---|---|---|---|---|
| | R % H + L | NR % Main | R % H + L | NR % Main | R % H + L | NR % Main | R % H + L | NR % Main |
| Citrate, NaCl, 0.1% Tween 80, pH 5.5 | 98.6 | 85.0 | 97.2 | 82.5 | 91.1 | 72.1 | 96.6 | 76.2 |
| Citrate, L-arg-HCl, 0.1% Tween 80, pH 5.5 | 98.8 | 85.0 | 97.4 | 83.1 | 91.3 | 76.2 | 97.6 | 78.9 |

CIEX-HPLC Analysis.

CIEX-HPLC separates molecules based on charge so that the acidic variants elute before the main peak species and the basic variants elute after the main peak species. The purity of CHIR-12.12 and its deamidation products content were measured as percentage of main peak and percentage of acidic variants, respectively.

Figure 14:
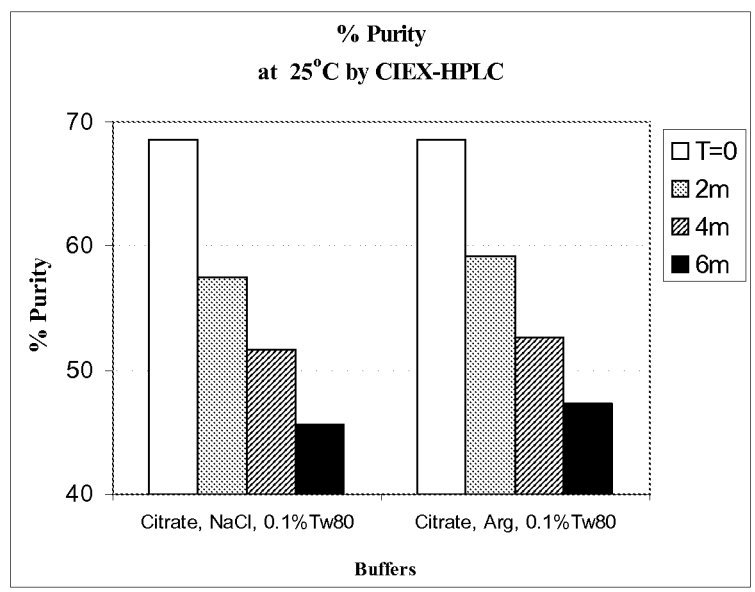
FIG. 14 shows % purity of mAb CHIR-12.12 in formulations containing either NaCl or L-arginine-HCl as the isotonizing agent when stored at 25° C. for 2, 4, or 6 months, as measured by CIEX-HPLC.
Figure 15:
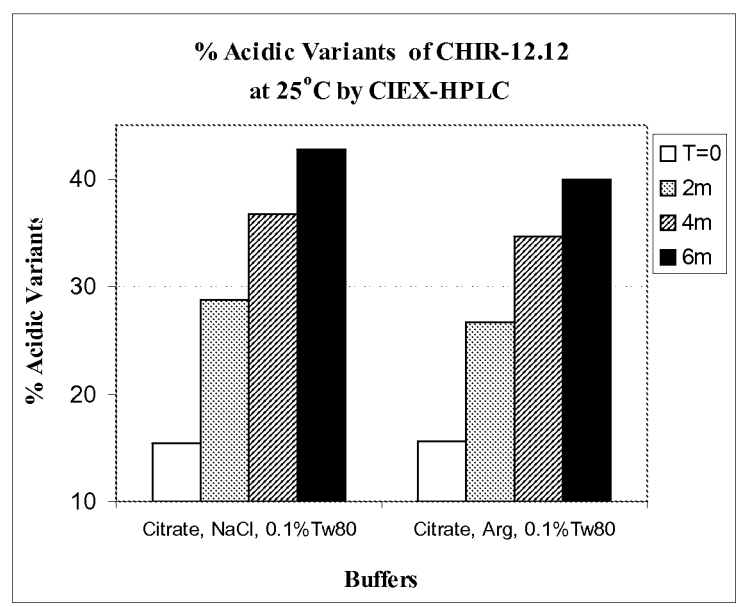
FIG. 15 shows % acidic variants of mAb CHIR-12.12 in formulations containing either NaCl or L-arginine-HCl as the isotonizing agent when stored at 25° C. for 2, 4, or 6 months, as measured by CIEX-HPLC.
Figure 16:
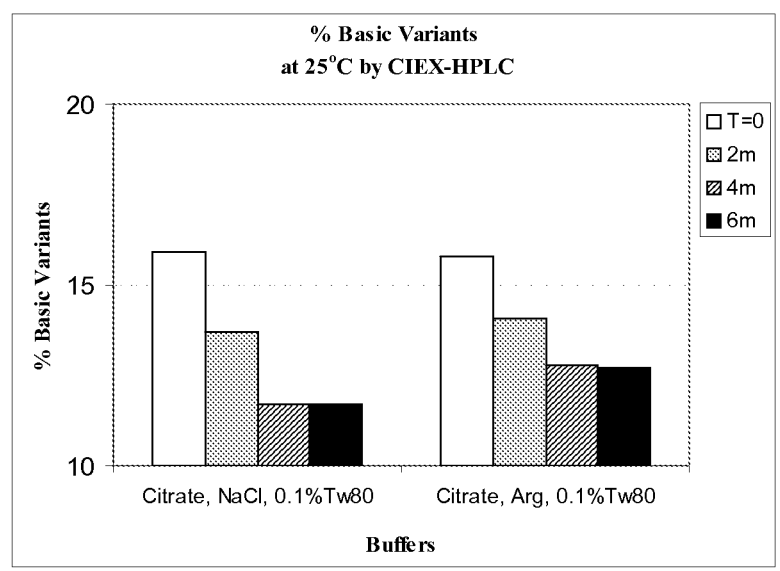
FIG. 16 shows % basic variants of mAb CHIR-12.12 in formulations containing either NaCl or L-arginine-HCl as the isotonizing agent when stored at 25° C. for 2, 4, or 6 months, as measured by CIEX-HPLC.

FIGS. 14, 15, and 16 show the purity, the content of deamidation product, and the content of basic variants, respectively, in the two formulations. At time 0, the two formulations had 68.6% purity and 15.5% deamidation product as well as 15.9% basic variants. When stored at 25° C., the L-arginine-HCl-containing formulation remained at higher purity and at higher content of basic variants, and exhibited a lower percentage of deamidation products than the NaCl-containing formulation. Upon storage at 25° C. for 6 months, the L-arginine-HCl-containing formulation had 47.3% purity, 12.5% basic variants, and 40.0% deamidation product generated, while the NaCl-containing formulation had 45.6% purity, 11.7% basic variants, and 42.7% deamidation product. Although the L-arginine-HCl- and NaCl-containing formulations showed little change throughout 6 months storage at 5° C., the CIEX-HPLC results under accelerated storage conditions (25° C.) predict that L-arginine-HCl will likely be superior to NaCl in improving the long-term real-time stability of CHIR-12.12 against deamidation.

In summary, this study demonstrates that 150 mM L-arginine-HCl not only renders isotonicity to the CHIR-12.12 liquid formulation, but also increases the conformational stability of CHIR-12.12 against aggregation, fragmentation, and deamidation. L-arginine-HCl is superior to NaCl under accelerated stability conditions, and the accelerated stability data further predict a longer shelf-life for the CHIR-12.12 L-arginine-HCl formulation.

Example 3

Effects of Tween 80 and Tween 20 in Minimizing Aggregation of CHIR-12.12 Bulk Drug Substance from Frozen Storage Frozen storage of the CHIR-12.12 bulk drug substance is preferred over liquid storage for several reasons including increased product stability and shelf life, decreased microbial growth, as well as elimination of foaming during transport.

However, freezing and subsequent thawing can induce stresses in protein solution by introducing ice-liquid interfaces and concentration gradient of solutes. The stresses may denature proteins and lead to aggregation and, in worse cases, formation of visible particulates or precipitates. As protein aggregates have been frequently associated with reduced drug potency and increased immunogenicity, minimizing aggregation by optimizing protein formulation components and freeze-thaw conditions is very critical.

Formulation excipients, such as sugars, polyhydric alcohols, amino acids, and surfactants can possibly stabilize proteins and antibodies from aggregation. In one monoclonal antibody study, a few commonly used sugars, polyhydric alcohols, and amino acids were found to be more effective than surfactants in reducing freeze-thaw triggered aggregation. However, earlier studies with CHIR-12.12 showed that the use of a sugar (e.g., trehalose), a polyhydric alcohol (e.g., sorbitol), or an amino acid (e.g. glycine) alone could not significantly reduce aggregation of CHIR-12.12 during freezing and thawing.

This study focused on formulation approaches to minimize aggregation of CHIR-12.12 during freezing and thawing. In this manner, various surfactants were evaluated in order to minimize the freeze-thaw-induced aggregation of CHIR-12.12. Although it is unlikely that the actual frozen CHIR-12.12 drug substance would experience multiple freeze-thaw cycling as evaluated in this study, extensive freeze-thaw stressing studies are worst-case scenario evaluations used to predict the potential for the formulated bulk drug to aggregate should multiple freezing and thawing inadvertently occur during long-term storage and transportation.

Materials

CHIR-12.12 bulk DS lots # UA7870, # TC23-2, # UB 1291, # PD010705A, and #CD083005A were used for this study. Tween 80, Tween 20, Brij 35, and Pluronic F68 were purchased from Sigma, J. T. Baker, Alfa Aesar, and MediaTech Cellgro, respectively. The polycarbonate (PC) bottle for frozen storage of CHIR-12.12 drug substance was purchased from Nalgene.

Methods

Except for the control samples, all other samples were subjected to complete freezing at −20° C. or −60° C. followed by complete thawing at ambient temperature for multiple cycles.

Three analytical methods were employed to detect CHIR-12.12 protein ranging from monomer to visible aggregates. Visual observation was performed under Tyndal light (M.W. Technologies, Inc.) for detecting visible particulates. Liquid Particle Counting System (HIAC/Royco) was used to count sub-visible aggregates≥10 μm and ≥25 μm. Dynamic Light Scattering Analyzer (Malvern Nano Series) was employed to determine hydrodynamic diameters of monomer and aggregates and the particle size distribution.

Visible Particle Evaluation.

The samples for the freeze-thaw study were prepared from CHIR-12.12 drug substance lot #UA7870 and lot # TC23-2. All samples were formulated in 10 mM sodium citrate/citric acid, 150 mM NaCl, and pH 5.5 buffer solution by dialysis, followed by the addition of varying percentages (0-0.5% w/v) of one of the following nonionic surfactants: Tween 80, Tween 20, Brij 35, and Pluronic F68. Each sample of 2.5 ml was filled into glass vials and subjected to overnight freezing at −60° C. and complete thawing at ambient temperature for up to eight cycles. The samples at initial time (time 0) and after each freeze-thaw cycle were visually examined for clarity and visible precipitates/aggregates.

Sub-Visible Particle Count.

CHIR-12.12 drug substance lot # UB 1291 and # PD010705A were formulated in the solution (20 mg/ml CHIR-12.12, 10 mM sodium citrate/citric acid, 150 mM NaCl, at pH 5.5), followed by the addition of 0-0.5% (w/v) of Tween 80 or Tween 20. Aliquots of 20-ml formulation samples were filled into 125 cc polycarbonate bottles and subjected to freezing at −60° C. and thawing at ambient temperature. After five cycles of freeze-thaw, the samples were measured for sub-visible aggregates≥10 μm and ≥25 μm using HIAC-Royco Liquid Particle Counting System.

Dynamic Light Scattering Analysis.

Prior to and post 5 cycles of freeze-thaw, the formulations (20 mg/ml CHIR-12.12, 10 mM sodium citrate/citric acid, 150 mM L-arginine-HCl, 5 mM L-methionine, 0-0.2% Tween 20, and pH 5.5) were evaluated for aggregates using Dynamic Light Scattering Analyzer.

Dynamic Light Scattering (DLS) spectroscopy calculates the hydrodynamic diameter of particles including monomer and aggregates from the measured diffusion coefficient of the particles using the Stokes-Einstein equation and the assumption that the particles are spherical. The number of aggregates species and polydispersity are also obtained from DLS studies.

Results

Visible Particle Evaluation.

Table 4 summarizes the results of the visual observation. At time 0, which was prior to initiating the freeze-thaw cycles, all the samples were slightly opalescent without visible aggregates/precipitates. After one freeze-thaw cycle, a few visible aggregates/precipitates formed in all the formulations without any added surfactant, and in the formulations containing 0-0.05% (w/v) of Tween 80 and in the formulations containing 0-0.1% (w/v) Brij 35 as well as in the samples containing 0-0.5% (w/v) Pluronic F68. The samples containing 0.05%-0.5% (w/v) Tween 20 did not show any aggregates or precipitates throughout the eight cycles of freeze-thaw. This suggests Tween 20 is more effective than Tween 80 in preventing the formation of large insoluble aggregates from multiple freeze-thaw cycles. Brij 35 and Pluronic F68 were much less effective than Tween 80 and Tween 20.

TABLE 4

Visual appearance of CHIR-12.12 in the citrate-buffered formulations with varying concentrations of surfactant.

Formulation 20 mg/ml CHIR-12.12, 10 mM Citrate/Citric Acid, 150 mM NaCl, Tween 80, pH 5.5

| Tween 80 Conc. (w/v) | T = 0 | 1XFT* | XFT | 4XFT | 5XFT | 6XFT | 8XFT |
|---|---|---|---|---|---|---|---|
| 0% | SO | SO, a few ppt | SO, ppt | SO, ppt | SO, ppt | SO, ppt | SO, ppt |
| 0.05% | SO | SO, a few ppt | SO, a few ppt | SO, ppt | SO, ppt | SO, ppt | SO, ppt |
| 0.10% | SO | SO | SO | SO, a few | SO, a few ppt | SO, a few ppt | SO, a few ppt |

TABLE 4-continued

Visual appearance of CHIR-12.12 in the citrate-buffered formulations with varying concentrations of surfactant.

| | | | | | | | |
|---|---|---|---|---|---|---|---|
| 0.20% | SO | SO | SO | SO | SO, a few ppt | SO, a few ppt | SO, a few ppt |
| 0.50% | SO | SO | SO | SO | SO, a few ppt | SO, a few ppt | SO, a few ppt |

Formulation 20 mg/ml CHIR-12.12, 10 mM Citrate/Citric Acid, 150 mM NaCl, Tween 20, pH 5.5

| Tween 20 Conc. (w/v) | T = 0 | 1XFT | 2XFT | 4XFT | 5XFT | 6XFT | 8XFT |
|---|---|---|---|---|---|---|---|
| 0% | SO | SO, a few ppt | SO, a few ppt | SO, ppt | SO., ppt | SO, ppt | SO, ppt |
| 0.01% | SO | SO | SO | SO | SO, a few ppt | SO, a few ppt | SO, ppt |
| 0.05% | SO | SO | SO | SO | SO | SO | SO |
| 0.10% | SO | SO | SO | SO | SO | SO | SO |
| 0.20% | SO | SO | SO | SO | SO | SO | SO |
| 0.50% | SO | SO | SO | SO | SO | SO | SO |

Formulation 20 mg/ml CHIR-12.12, 10 mM Citrate/Citric Acid, 150 mM NaCl, Brij 35, pH 5.5

| Brij 35 Conc. (w/v) | T = 0 | 1XFT | 2XFT | 4XFT | 5XFT | 6XFT | 8XFT |
|---|---|---|---|---|---|---|---|
| 0% | SO | SO, ppt | SO, ppt | SO, ppt | SO, ppt | SO, ppt | SO, ppt |
| 0.01% | SO | SO, a few ppt | SO, a few ppt | SO, a few ppt | SO, a few ppt | SO, a few ppt | SO, a few ppt |
| 0.10% | SO | SO, a few ppt | SO, a few ppt | SO, a few ppt | SO, a few ppt | SO, a few ppt | SO, a few ppt |
| 0.20% | SO | SO | SO | SO | SO | SO, a few ppt | SO, a few ppt |
| 0.50% | SO | SO | SO | SO | SO | SO, a few ppt | SO, a few ppt |

Formulation 20 mg/ml CHIR-12.12, 10 mM Citrate/Citric Acid, 150 mM NaCl, Pluronic F68, pH 5.5

| Plur. F68 Conc. (w/v) | T = 0 | 1XFT | 2XFT | 4XFT | 5XFT | 6XFT | 8XFT |
|---|---|---|---|---|---|---|---|
| 0% | SO | SO, ppt | SO, ppt | SO, ppt | SO, ppt | SO, ppt | SO, ppt |
| 0.01% | SO | SO, a few ppt | SO, a few ppt | SO, a few ppt | SO, a few ppt | SO, a few ppt | SO, a few ppt |
| 0.10% | SO | SO, a few ppt | SO, a few ppt | SO, a few ppt | SO, a few ppt | SO, a few ppt | SO, a few ppt |
| 0.20% | SO | SO, a few ppt | SO, a few ppt | SO, a few ppt | SO, a few ppt | SO, a few ppt | SO, a few ppt |
| 0.50% | SO | SO, a few ppt | SO, a few ppt | SO, a few ppt | SO, a few ppt | SO, a few ppt | SO, a few ppt |

Keys:
XFT = no. of freeze-thaw cycles;
SO = slightly opalescent;
ppt = precipitate/aggregate Sub-Visible Particle Count.

Table 5 shows the sub-visible aggregates counts per ml of citrate/citric acid-buffered formulations containing varying concentrations of Tween 80. A downward trend in the sub-visible particle counts was observed as the Tween 80 concentration increased; the decrease in the sub-visible particle counts was modest when Tween 80 was above 0.1% (w/v), suggesting the appropriate concentration for the use of Tween 80 was 0.1-0.2% (w/v).

TABLE 5

Sub-visible particle counts in the formulations containing 20 mg/ml CHIR-12.12, 10 mM sodium citrate/citric acid, 150 mM NaCl, and varying concentrations (0-0.2% w/v) of Tween 80 at pH 5.5.

| Concentration of Tween 80 (w/v) | Sub-Visible Particle Counts/ml after 5 Freeze-Thaw Cycles | |
|---|---|---|
| | ≥10 μm | ≥25 μm |
| 0% Tween 80 | 1439 | 23 |
| 0.05% Tween 80 | 148 | 3 |
| 0.10% Tween 80 | 44 | 1 |
| 0.20% Tween 80 | 39 | 1 |

Table 6 shows the sub-visible aggregates counts per ml of the citrate/citric acid-buffered formulations with or without Tween 20. The aggregate counts were greatly reduced with addition of Tween 20 in the formulation. When Tween 20 was 0.05% (w/v) and above, the decrease in the sub-visible aggregates counts almost reached a plateau, suggesting the appropriate concentration of Tween 20 was around 0.05-0.2% (w/v).

TABLE 6

Sub-visible particle counts in the formulations containing 20 mg/ml CHIR-12.12, 10 mM sodium citrate/citric acid, 150 mM NaCl, and varying concentrations (0-0.2% w/v) of Tween 20 at pH 5.5.

| Concentration of Tween 20 (w/v) | Sub-Visible Particle Counts/ml after 5 Freeze-Thaw Cycles | |
|---|---|---|
| | ≥10 μm | ≥10 μm |
| 0% Tween 20 | 1671 | 41 |
| 0.01% Tween 20 | 46 | 2 |
| 0.05% Tween 20 | 32 | 3 |
| 0.1% Tween 20 | 11 | 1 |
| 0.2% Tween 20 | 25 | 1 |

Additionally, Tables 5 and Table 6 show both Tween 80- and Tween 20-containing formulations generated very few aggregates≥25 μm, and the Tween 20-containing formulation generated fewer aggregates≥10 μm than did the Tween 80-containing formulation after 5 cycles of freeze-thaw. The results indicate Tween 20 is more effective than Tween 80 in minimizing the formation of sub-visible aggregates in the CHIR-12.12 citrate/citric acid-buffered formulation.

Based on the results in Tables 4, 5, and 6, Tween-20 represents a preferred excipient over Tween 80 to minimize the formation of aggregates in CHIR-12.12 formulations. Accordingly, additional studies were conducted to further optimize the concentrations of Tween-20 needed to obviate the formation of aggregates in CHIR-12.12 formulations. The formulations (20 mg/ml CHIR-12.12, 10 mM sodium citrate/citric acid, 150 mM L-arginine-HCl, 5 mM L-methionine, 0-0.2% Tween 20, at pH 5.5) were prepared from CHIR-12.12 drug substance lot # CD083005A. 20 ml formulation samples were filled into 125 cc polycarbonate bottles and subjected to freezing at −20° C. and thawing at ambient temperature. Prior to and post five freeze-thaw cycles, the formulation samples were measured for sub-visible particle counts using HIAC-Royco liquid particle counter. The results are summarized in Table 7.

TABLE 7

Sub-visible particle counts in the formulations containing 20 mg/ml CHIR-12.12, 10 mM sodium citrate/citric acid, 150 mM L-arginine-HCl, 5 mM L-methionine, 0-0.2% Tween 20, at pH 5.5.

| Concentration of Tween 20 (w/v) | Particle Counts/ml ≥10 μm | | Particle Counts/ml ≥25 μm | |
|---|---|---|---|---|
| | Prior to FT | Post 5XFT* | Prior to FT | Post 5XFT |
| 0% Tween 20 | 23 | 169 | 7 | 5 |
| 0.005% Tween 20 | 4 | 24 | 0 | 2 |
| 0.025% Tween 20 | 5 | 6 | 1 | 1 |
| 0.05% Tween 20 | 2 | 9 | 0 | 1 |
| 0.1% Tween 20 | 6 | 7 | 1 | 1 |
| 0.2% Tween 20 | 10 | 64 | 1 | 5 |

*Key: XFT = no. of freeze-thaw cycles.

After five cycles of freeze-thaw, the samples containing L-arginine-HCl and L-methionine generated much less aggregates than the formulation without L-arginine-HCl and L-methionine, i.e., 169 particles/ml≥10 μm versus 1439 or 1671 particles/ml≥10 μm in the absence of Tween 20 (see Tables 6 and 7). However, until Tween 20 was introduced, L-arginine-HCl and L-methionine did not significantly reduce the freeze-thaw-induced aggregates to a minimum level. This suggests that L-arginine-HCl and L-methionine are not sufficiently effective in minimizing freeze-thaw-induced aggregation of CHIR-12.12.

From the data summarized in Tables 5-7, the sub-visible aggregates counts of freeze-thawed samples containing 0.025-0.1% (w/v) Tween 20 remained comparable to the respective samples prior to freeze-thaw cycling. This indicates that formulations containing Tween 20 in combination with L-arginine-HCl and L-methionine generated minimum sub-visible aggregates. Thus, Tween 20 is the excipient in the formulation that effectively minimizes CHIR-12.12 from generating sub-visible aggregates during freezing and thawing. The effective concentration of Tween 20 was determined to be 0.025-0.1% (w/v).

Dynamic Light Scattering Analysis.

Table 8 shows the mean hydrodynamic diameter of the particles, polydispersity, and percent intensity of the monomer species of CHIR-12.12. The Dynamic Light Scattering analysis detected only monomer species in all the samples prior to and post five cycles of freeze-thaw, as shown by 100% intensity of the monomer species. This suggests all the samples were mainly composed of monomers. After 5 cycles of freeze-thaw studies, a few aggregates (possibly dimer or trimer) might coexist with the monomer in the samples without Tween 20 and with 0.005% (w/v) Tween 20, as shown by the increases in hydrodynamic diameter and polydispersity. The samples containing 0.025-0.1% (w/v) Tween 20 showed little change in hydrodynamic diameter and the polydispersity values, indicating they remained at the previous levels of monomers without appreciable aggregate formation.

TABLE 8

Dynamic Light Scattering analysis of CHIR-12.12 before and after five cycles of freeze-thaw of the formulation containing 20 mg/ml CHIR-12.12, 10 mM sodium citrate/citric acid, 150 mM L-arginine-HCl, 5 mM L-methionine, and varying concentrations (0-0.2%) of Tween 20, at pH 5.5)

| Concentration of Tween 20 (w/v) | Mean Hydrodynamic Diameter (mm) | | Polydispersity | | Intensity % of Monomer Species | |
|---|---|---|---|---|---|---|
| | Prior to FT* | Post 5XFT* | Prior to FT | Post 5XFT | Prior to FT | Post 5XFT |
| 0% Tween 20 | 12.2 | 12.4 | 0.047 | 0.055 | 100.0 | 100.0 |
| 0.005% Tween 20 | 12.2 | 12.4 | 0.045 | 0.045 | 100.0 | 100.0 |
| 0.025% Tween 20 | 12.3 | 12.4 | 0.035 | 0.034 | 100.0 | 100.0 |
| 0.05% Tween 20 | 12.3 | 12.2 | 0.035 | 0.031 | 100.0 | 100.0 |
| 0.1% Tween 20 | 12.4 | 12.4 | 0.035 | 0.039 | 100.0 | 100.0 |
| 0.2% Tween 20 | 12.3 | 12.2 | 0.036 | 0.043 | 100.0 | 100.0 |

*Key: FT = freeze-thaw; XFT = no. of freeze-thaw cycles.

Based on the visual observation, sub-visible particle counts, and the Dynamic Light Scattering analysis, the optimum concentration of Tween 20 was determined to be 0.025-0.1% (w/v) for minimizing CHIR-12.12 from freeze-thaw-induced aggregation.

In summary, both Tween 20 and Tween 80 have been found to minimize CHIR-12.12 aggregation during freezing and thawing. The optimum concentrations of Tween 20 and Tween 80 are 0.025-0.1% (w/v) and 0.1-0.2 (w/v) %, respectively. Tween 20 is more effective than Tween 80 in that a lower concentration of Tweeze 20 reduces the number and extent of the formation of aggregates to a lower level. This study has demonstrated that the addition of an optimum concentration of Tween, preferably in combination with L-arginine-HCl and L-methionine, enables the storage of the citrate/citric acid-buffered CHIR-12.12 bulk drug substance at −20° C. or below without significant aggregation.

Example 4

Assays for Antagonist Activity of Anti-CD40 Antibodies

The following assays can be used to assess the antagonist activity of an anti-CD40 antibody. Human B cells for these assays can be obtained, for example, by isolation from tonsils obtained from individuals undergoing tonsillectomies, essentially as described in De Groot et al. (1990) *Lymphokine Research* (1990) 9:321. Briefly, the tissue is dispersed with scalpel blades, phagocytic and NK cells are depleted by treatment with 5 mM L-leucine methyl ester and T cells are removed by one cycle of rosetting with sheep erythrocytes (SRBC) treated with 2-aminoethyl isothiouronium bromide. The purity of the resulting B lymphocyte preparations can be checked by indirect immunofluorescent labelling with anti-(CD20) mAb B1 (Coulter Clone, Hialeah, Fla.) or anti-(CD3) mAb OKT3 (Ortho, Raritan, N.J.) and a FITC-conjugated F(ab')$_2$ fragment of rabbit anti-(mouse Ig) (Zymed, San Francisco, Calif.), and FACS analysis.

B-Cell Proliferation Assay.

B cells (4×10⁴ per well) are cultured in 200 μl IMDM supplemented with 10% fetal calf serum in flat bottom 96-well microtiter plates. B cells are stimulated by addition of immobilized anti-(IgM) antibodies (Immunobeads; 5 μg/ml; BioRad, Richmond, Calif.). Where desired, 100 U/ml recombinant IL-2 is added. Varying concentrations of test monoclonal antibodies (mAbs) are added at the onset of the microcultures and proliferation is assessed at day 3 by measurement of the incorporation of (3H)-thymidine after 18 hour pulsing.

An antagonist anti-CD40 antibody does not significantly costimulate human B-cell proliferation in the presence of immobilized anti-IgM or in the presence of immobilized anti-IgM and IL-2.

Banchereau-Like B-Cell Proliferation Assay.

For testing the ability of anti-CD40 monoclonal antibodies to stimulate B-cell proliferation in a culture system analogous to that described by Banchereau et al. (1991) *Science* (1991) 251:70, mouse 3T6 transfectant cells expressing the HR allellic form of human FcγRII are used. B cells (2×10⁴ per well) are cultured in flat-bottom microwells in the presence of 1×10⁴ transfectant cells (irradiated with 5000 Rad) in 200 μl IMDM supplemented with 10% fetal calf serum and 100 U/ml recombinant IL-4. Before addition of the B cells, the 3T6 cells are allowed to adhere to the culture plastic for at least 5 hours. Anti-CD40 mAbs are added at concentrations varying from 15 ng/ml to 2000 ng/ml and proliferation of B cells is assessed by measurement of thymidine incorporation at day 7, upon 18 hour pulsing with [³H]thymidine.

Inhibition of S2C6-Stimulated B-Cell Proliferation Using Antagonist Anti-CD40 mAbs.

Antagonist anti-CD40 monoclonal antibodies (mAbs) can also be characterized by their ability to inhibit stimulation of B-cell proliferation by an anti-CD40 antibody such as S2C6 (also known as SGN-14, which is reportedly an agonist of CD40 stimulation of proliferation of normal B cells; Francisco et al. (2000) *Cancer Res.* 60:3225-3231) using the B-cell Proliferation Assay described above. Human tonsillar B cells (4×10⁴ per well) are cultured in 200 μl in microwells in the presence of anti-IgM coupled to Sepharose beads (5 μg/ml) and anti-CD40 mAb S2C6 (1.25 μg/ml). Varying concentrations of an anti-CD40 mAb of interest are added and [³H]-thymidine incorporation is assessed after 3 days. As a control anti-(glucocerebrosidase) mAb 8E4 can be added in similar concentrations. Barneveld et al. (1983) *Eur. J. Biochem.* 134:585. An antagonist anti-CD40 antibody can inhibit the costimulation of anti-IgM induced human B-cell proliferation by mAb S2C6, for example, by at least 75% or more (i.e., S2C6-stimulated proliferation in the presence of an antagonist anti-CD40 antibody is no more than 25% of that observed in the absence of the antagonist anti-CD40 antibody). In contrast, no significant inhibition would be seen with equivalent amounts of non-relevant mAb 8E4, directed to β-glucocerebrosidase. Barneveld et al., supra. Such a result would indicate that the anti-CD40 mAbs does not deliver stimulatory signals for the proliferation of human B cells, but, conversely, can inhibit stimulatory signals exerted by triggering CD40 with another mAb.

B-Cell Activation Assay with EL4B5 Cells.

Zubler et al. (1985) *J. Immunol.* (1985) 134:3662 observed that a mutant subclone of the mouse thymoma EL-4 line, known as EL4B5, could strongly stimulate B cells of both murine and human origin to proliferate and differentiate into immunoglobulin-secreting plasma cells in vitro. This activation was found to be antigen-independent and not MHC restricted. For optimal stimulation of human B cells, the presence of supernatant from activated human T cells was needed but a B-cell response also occurred when EL4B5 cells were preactivated with phorbol-12-myristate 13-acetate (PMA) or IL-1. Zubler et al. (1987) *Immunological Reviews* 99:281; and Zhang et al. (1990) *J. Immunol.* 144:2955. B-cell activation in this culture system is efficient—limiting dilution experiments have shown that the majority of human B cells can be activated to proliferate and differentiate into antibody-secreting cells. Wen et al. (1987) *Eur. J. Immunol.* 17:887.

B cells (1000 per well) are cultured together with irradiated (5000 Rad) EL4B5 cells (5×10⁴ per well) in flat bottom microtiter plates in 200 μl IMDM supplemented with 10% heat-inactivated fetal calf serum, 5 ng/ml phorbol-12-myristate 13-acetate (Sigma) and 5% human T-cell supernatants mAbs are added at varying concentrations at the onset of the cultures and thymidine incorporation is assessed at day 6 after 18 hour pulsing with [³H]-thymidine. For the preparation of T-cell supernatant, purified T cells are cultured at a density of 10⁶/ml for 36 hours in the presence of 1 μg/ml PHA and 10 ng/ml PMA. Wen et al. (1987) *Eur. J. Immunol.* (1987) 17:887. T-cell supernatant is obtained by centrifugation of the cells and stored at −20° C. The effectiveness of T-cell supernatants in enhancing proliferation of human B cells in EL4B5-B cell cultures is tested and the most effective supernatants are pooled for use in experiments. When assessing the effect of an anti-CD40 antibody on EL4B5-induced human B-cell proliferation, a monoclonal antibody such as MOPC-141 (IgG2b) can be added as a control.

An antagonist anti-CD40 antibody can inhibit B-cell proliferation stimulated by the EL4B5 cell line, for example, by at least 75% or more (i.e., EL4B5-induced B cell proliferation in the presence of an antagonist anti-CD40 antibody is no more than 25% of that observed in the absence of the antagonist anti-CD40 antibody). In contrast, a control antibody such as MOPC-141 would have no significant effect on EL4B5-induced B cell proliferation.

Human T Cell Helper Assay for Antibody Production by B Cells.

An antagonist anti-CD40 antibody can function as an antagonist of immunoglobulin production by B cells. An anti-CD40 antibody can be tested for this type of antagonist activity by assessing the antibody's ability to inhibit immunoglobulin production by B cells that have been stimulated in a contact-dependent manner with activated T cells in a T cell helper assay. In this manner, 96-well tissue culture plates are coated with a 1:500 dilution of ascites fluid of anti-CD3 mAb CLB-T3/3 (CLB, Amsterdam, The Netherlands). As indicated costimulatory mAbs are added: anti CD2 mAbs CLB-T11.1/1 and CLB-T11.2/1 (CLB, Amsterdam, The Netherlands), both ascites 1:1000 and anti-CD28 mAb CLB-28/1 (CLB, Amsterdam, The Netherlands). Subsequently, tonsillar T cells (irradiated, 3000 Rad; 10⁵ per well), tonsillar B cells (10⁴ per well), and rIL-2 (20 U/ml) are added. The final volume of each cell culture is 200 μl. After 8 days, cells are spun down, and cell-free supernatant is harvested. The concentrations of human IgM and IgG in (diluted) samples is estimated by ELISA as described below.

In one embodiment, human tonsillar B cells (10⁴/well) are cultured together with irradiated purified T cells (3000 rad, 10⁵/well) in 96-well plates, coated with anti-CD3 mAb and with or without different mAbs to costimulate the T cells. After 8 days of culture the supernatants are harvested for the determination of immunoglobulin production by the B cells. Immunoglobulin production by the B cells is assessed by the ELISA assay described below. The anti-CD40 antibody of interest is added in varying concentrations from the onset of the cultures. As a control, mAb MOPC-141 can be added.

An antagonist anti-CD40 antibody can inhibit IgG and IgM antibody production of B cells stimulated by human T cells by at least 50% or more (i.e., T cell-induced antibody production by B cells in the presence of an antagonist anti-CD40 antibody is no more than 50% of that observed in the absence of the antagonist anti-CD40 antibody). In contrast, a control antibody such as MOPC-141 would have no significant effect on T cell-induced antibody production by B cells.

ELISA Assay for Immunoglobulin Quantification.

The concentrations of human IgM and IgG are estimated by ELISA. 96-well ELISA plates are coated with 4 µg/ml mouse anti-human IgG mAb MH 16-01 (CLB, Amsterdam, The Netherlands) or with 1.2 µg/ml mouse anti-human IgM mAb 4102 (Tago, Burlingame, Calif.) in 0.05 M carbonate buffer (pH=9.6), by incubation for 16 h at 4° C. Plates are washed 3 times with PBS-0.05% Tween-20 (PBS-Tween) and saturated with BSA for 1 hour. After 2 washes the plates are incubated for 1 h at 37° C. with different dilutions of the test samples. After 3 washes, bound Ig is detected by incubation for 1 h at 37° C. with 1 µg/ml peroxidase-labeled mouse anti-human IgG mAb MH 16-01 (CLB) or mouse anti-human IgM mAb MH 15-01 (CLB). Plates are washed 4 times and bound peroxidase activity is revealed by the addition of O-phenylenediamine as a substrate. Human standard serum (H00, CLB) is used to establish a standard curve for each assay.

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A stable liquid pharmaceutical composition comprising:
   a) an antagonist anti-CD40 monoclonal antibody as a therapeutically or prophylactically active component, wherein said monoclonal antibody is capable of specifically binding to a human CD40 antigen expressed on the surface of a human B cell, said monoclonal antibody being free of significant agonist activity when bound to the CD40 antigen expressed on the surface of said B cell;
   b) an amount of an isotonizing agent sufficient to render said composition as having an osmolality of about 240 mmol/kg to about 360 mmol/kg, wherein said isotonizing agent is arginine in its acidic form (arginine-HCl), and wherein said composition does not include NaCl as an additional isotonizing agent; and
   c) a buffering agent to maintain the pH of said composition within a range from about pH 5.0 to about pH 7.0, wherein said buffering agent is a citrate/citric acid buffer;
   wherein said antagonist anti-CD40 monoclonal antibody is present in said composition at a concentration of about 0.1 mg/ml to about 50.0 mg/ml and is selected from the group consisting of:
   i) a monoclonal antibody comprising the variable and constant region sequences shown in SEQ ID NO:2 and the variable and constant region sequences shown in SEQ ID NO:4;
   ii) a monoclonal antibody comprising the variable and constant region sequences shown in SEQ ID NO:2 and the variable and constant region sequences shown in SEQ ID NO:5;
   iii) a monoclonal antibody comprising the leader, variable and constant region sequences shown in SEQ ID NO:2 and the leader, variable and constant region sequences shown in SEQ ID NO:4; and
   iv) a monoclonal antibody comprising the leader, variable and constant region sequences shown in SEQ ID NO:2 and the leader, variable and constant region sequences shown in SEQ ID NO:5;
   wherein the concentration of said buffering agent is about 5 mM to about 100 mM, and wherein said composition comprises arginine-HCl at a concentration of about 50 mM to about 200 mM.

2. The composition of claim 1, wherein the concentration of said buffering agent is about 5 mM to about 20 mM.

3. The composition of claim 2, wherein the concentration of said buffering agent is about 10 mM.

4. The composition of claim 1, wherein said buffering agent is a sodium citrate/citric acid buffer.

5. The composition of claim 4, wherein said composition has a pH of about pH 5.5.

6. The composition of claim 1, wherein said composition comprises arginine-HCl at a concentration of about 100 mM to about 175 mM.

7. The composition of claim 6, wherein said composition comprises arginine-HCl at a concentration of about 150 mM.

8. The composition of claim 1, wherein said buffering agent is a sodium citrate/citric acid buffer, and wherein the concentration of said buffering agent is about 10 mM, and said composition has a pH of about pH 5.5.

9. The composition of claim 8, wherein said composition comprises arginine-HCl at a concentration of about 150 mM.

10. The composition of claim 1, further comprising a surfactant.

11. The composition of claim 10, wherein said surfactant is polysorbate 20.

12. The composition of claim 11, wherein said surfactant is polysorbate 20 at a concentration of about 0.001% to about 1.0% (w/v).

13. The composition of claim 12, wherein said composition comprises polysorbate 20 at a concentration of about 0.025% to about 0.1% (w/v).

14. The composition of claim 1, further comprising methionine in an amount sufficient to inhibit oxidation of at least one oxidizable amino acid residue in said anti-CD40 monoclonal antibody during storage of said composition.

15. The composition of claim 14, wherein said composition comprises methionine at a concentration of about 0.5 mM to about 20.0 mM.

16. The composition of claim 15, wherein said composition comprises methionine at a concentration of about 1.0 mM to about 20.0 mM.

17. The composition of claim 16, wherein said composition comprises methionine at a concentration of about 5.0 mM.

18. The composition of claim 1, wherein said antagonist anti-CD40 monoclonal antibody is present in said composition at a concentration of about 1.0 mg/ml to about 35.0 mg/ml.

19. The composition of claim 18, wherein said antagonist anti-CD40 monoclonal antibody is present in said composition at a concentration of about 10.0 mg/ml to about 35.0 mg/ml.

20. The composition of claim 1, wherein said composition is stable at a temperature of about 2° C. to about 8° C. for a period of at least 18 months.

21. The composition of claim 1, wherein said composition is stable at about 25° C. for a period of at least 3 months.

22. The composition of claim 1, wherein said composition comprises arginine-HCl at a concentration of about 150 mM, and the buffering agent is sodium citrate/citric acid at a concentration of about 5 mM to about 20 mM, wherein said composition has a pH of about 5.0 to about 6.0 and an osmolality of about 250 mmol/kg to about 330 mmol/kg.

23. The composition of claim 1, wherein said composition further comprises methionine, polysorbate 20, or both methionine and polysorbate 20, wherein said methionine when present is present in said composition at a concentration of about 0.5 mM to about 20.0 mM, and wherein said polysorbate 20 when present is present in said composition at a concentration of about 0.025% to about 0.1% (w/v).

24. The composition of claim 22, wherein said antagonist anti-CD40 monoclonal antibody is present in said composition at a concentration of about 10.0 mg/ml to about 35.0 mg/ml.

25. The composition of claim 24, wherein said antagonist anti-CD40 monoclonal antibody is the monoclonal antibody CHIR-12.12 produced by the hybridoma cell line deposited with the ATCC as Patent Deposit No. PTA-5543.

26. A method for increasing stability of an anti-CD40 monoclonal antibody in a liquid pharmaceutical composition, said method comprising formulating said composition by combining said anti-CD40 monoclonal antibody, an amount of an isotonizing agent sufficient to render to said composition as having an osmolality of about 240 mmol/kg to about 360 mmol/kg, wherein said isotonizing agent is arginine in its acidic form (arginine-HCl) and wherein said composition does not include NaCl as an additional isotonizing agent, and a buffering agent to maintain the pH of said composition between about pH 5.0 and about pH 7.0, wherein said buffering agent is a citrate/citric acid buffer, and wherein said anti-CD40 monoclonal antibody is present in said composition at a concentration of about 0.1 mg/ml to about 50.0 mg/ml and is selected from the group consisting of:
  i) a monoclonal antibody comprising the variable and constant region sequences shown in SEQ ID NO:2 and the variable and constant region sequences shown in SEQ ID NO:4;
  ii) a monoclonal antibody comprising the variable and constant region sequences shown in SEQ ID NO:2 and the variable and constant region sequences shown in SEQ ID NO:5;
  iii) a monoclonal antibody comprising the leader, variable and constant region sequences shown in SEQ ID NO:2 and the leader, variable and constant region sequences shown in SEQ ID NO:4; and
  iv) a monoclonal antibody comprising the leader, variable and constant region sequences shown in SEQ ID NO:2 and the leader, variable and constant region sequences shown in SEQ ID NO:5;
  wherein the concentration of said buffering agent is about 5 mM to about 100 mM, and wherein said composition comprises arginine-HCl at a concentration of about 50 mM to about 200 mM.

27. A method for preparing a liquid pharmaceutical composition comprising an anti-CD40 monoclonal antibody, said method comprising formulating said composition by combining said anti-CD40 monoclonal antibody, an amount of an isotonizing agent sufficient to render to said composition as having an osmolality of about 240 mmol/kg to about 360 mmol/kg, wherein said isotonizing agent is arginine in its acidic form (arginine-HCl) and wherein said composition does not include NaCl as an additional isotonizing agent, and a buffering agent to maintain the pH of said composition between about pH 5.0 and about pH 7.0, wherein said buffering agent is a citrate/citric acid buffer, wherein said anti-CD40 monoclonal antibody is present in said composition at a concentration of about 0.1 mg/ml to about 50.0 mg/ml and is selected from the group consisting of:
  i) a monoclonal antibody comprising the variable and constant region sequences shown in SEQ ID NO:2 and the variable and constant region sequences shown in SEQ ID NO:4;
  ii) a monoclonal antibody comprising the variable and constant region sequences shown in SEQ ID NO:2 and the variable and constant region sequences shown in SEQ ID NO:5;
  iii) a monoclonal antibody comprising the leader, variable and constant region sequences shown in SEQ ID NO:2 and the leader, variable and constant region sequences shown in SEQ ID NO:4; and
  iv) a monoclonal antibody comprising the leader, variable and constant region sequences shown in SEQ ID NO:2 and the leader, variable and constant region sequences shown in SEQ ID NO:5;
  wherein the concentration of said buffering agent is about 5 mM to about 100 mM, and wherein said composition comprises arginine-HCl at a concentration of about 50 mM to about 200 mM.

28. The method of claim 26, wherein the concentration of said buffering agent is about 5 mM to about 20 mM, and wherein said composition comprises about 100 mM to about 175 mM arginine-HCl.

29. The method of claim 28, wherein the concentration of said buffering agent is about 10 mM, and wherein said composition comprises about 150 mM arginine-HCl.

30. The method of claim 26, wherein said buffering agent is a sodium citrate/citric acid buffer.

31. The method of claim 30, wherein said composition has a pH of about pH 5.5.

32. The method of claim 26, wherein said composition is formulated to further comprise methionine, polysorbate 20, or both methionine and polysorbate 20, wherein said methionine when present is present in said composition at a concentration of about 0.5 mM to about 20.0 mM, and wherein said polysorbate 20 when present is present in said composition at a concentration of about 0.025% to about 0.1% (w/v).

33. The method of claim 26, wherein said antagonist anti-CD40 monoclonal antibody is present in said composition at a concentration of about 10.0 mg/ml to about 35.0 mg/ml.

34. The method of claim 26, wherein said anti-CD40 monoclonal antibody is the monoclonal antibody CHIR-12.12 produced by the hybridoma cell line deposited with the ATCC as Patent Deposit No. PTA-5543, and wherein said monoclonal antibody is combined with about 50 mM to about 200 mM arginine-HCL and sodium citrate/citric acid buffer at a concentration of about 5 mM to about 20 mM.

35. The method of claim 27, wherein said anti-CD40 monoclonal antibody is the monoclonal antibody CHIR-12.12 produced by the hybridoma cell line deposited with the ATCC as Patent Deposit No. PTA-5543, wherein said monoclonal antibody is combined with about 50 mM to about 200 mM arginine-HCL and sodium citrate/citric acid buffer at a concentration of about 5 mM to about 20 mM.

36. The composition of claim 1, wherein said antagonist anti-CD40 monoclonal antibody is the monoclonal antibody CHIR-12.12 produced by the hybridoma cell line deposited with the ATCC as Patent Deposit No. PTA-5543.

37. The composition of claim 1, wherein said antagonist anti-CD40 monoclonal antibody is produced in a CHO cell line.

* * * * *

SEQUENCE LISTING

```
<160> NUMBER OF SEQ ID NOS: 12

<210> SEQ ID NO 1
<211> LENGTH: 720
<212> TYPE: DNA
<213> ORGANISM: Artificial Sequence
<220> FEATURE:
<223> OTHER INFORMATION: Coding sequence for light chain of 12.12 human
      anti-CD40 antibody
<221> NAME/KEY: CDS
<222> LOCATION: (1)...(720)

<400> SEQUENCE: 1 atg gcg ctc cct gct cag ctc ctg ggg ctg cta atg ctc tgg gtc tct         48
Met Ala Leu Pro Ala Gln Leu Leu Gly Leu Leu Met Leu Trp Val Ser
1               5                   10                  15 gga tcc agt ggg gat att gtg atg act cag tct cca ctc tcc ctg acc         96
Gly Ser Ser Gly Asp Ile Val Met Thr Gln Ser Pro Leu Ser Leu Thr
            20                  25                  30 gtc acc cct gga gag ccg gcc tcc atc tcc tgc agg tcc agt cag agc        144
Val Thr Pro Gly Glu Pro Ala Ser Ile Ser Cys Arg Ser Ser Gln Ser
        35                  40                  45 ctc ctg tat agt aat gga tac aac tat ttg gat tgg tac ctg cag aag        192
Leu Leu Tyr Ser Asn Gly Tyr Asn Tyr Leu Asp Trp Tyr Leu Gln Lys
    50                  55                  60 cca ggg cag tct cca cag gtc ctg atc tct ttg ggt tct aat cgg gcc        240
Pro Gly Gln Ser Pro Gln Val Leu Ile Ser Leu Gly Ser Asn Arg Ala
65                  70                  75                  80 tcc ggg gtc cct gac agg ttc agt ggc agt gga tca ggc aca gat ttt        288
Ser Gly Val Pro Asp Arg Phe Ser Gly Ser Gly Ser Gly Thr Asp Phe
                85                  90                  95 aca ctg aaa atc agc aga gtg gag gct gag gat gtt ggg gtt tat tac        336
Thr Leu Lys Ile Ser Arg Val Glu Ala Glu Asp Val Gly Val Tyr Tyr
            100                 105                 110 tgc atg caa gct cga caa act cca ttc act ttc ggc cct ggg acc aaa        384
Cys Met Gln Ala Arg Gln Thr Pro Phe Thr Phe Gly Pro Gly Thr Lys
        115                 120                 125 gtg gat atc aga cga act gtg gct gca cca tct gtc ttc atc ttc ccg        432
Val Asp Ile Arg Arg Thr Val Ala Ala Pro Ser Val Phe Ile Phe Pro
    130                 135                 140
```

```
cca tct gat gag cag ttg aaa tct gga act gcc tct gtt gtg tgc ctg        480
Pro Ser Asp Glu Gln Leu Lys Ser Gly Thr Ala Ser Val Val Cys Leu
145                 150                 155                 160 ctg aat aac ttc tat ccc aga gag gcc aaa gta cag tgg aag gtg gat        528
Leu Asn Asn Phe Tyr Pro Arg Glu Ala Lys Val Gln Trp Lys Val Asp
                165                 170                 175 aac gcc ctc caa tcg ggt aac tcc cag gag agt gtc aca gag cag gac        576
Asn Ala Leu Gln Ser Gly Asn Ser Gln Glu Ser Val Thr Glu Gln Asp
            180                 185                 190 agc aag gac agc acc tac agc ctc agc agc acc ctg acg ctg agc aaa        624
Ser Lys Asp Ser Thr Tyr Ser Leu Ser Ser Thr Leu Thr Leu Ser Lys
        195                 200                 205 gca gac tac gag aaa cac aaa gtc tac gcc tgc gaa gtc acc cat cag        672
Ala Asp Tyr Glu Lys His Lys Val Tyr Ala Cys Glu Val Thr His Gln
    210                 215                 220 ggc ctg agc tcg ccc gtc aca aag agc ttc aac agg gga gag tgt tag        720
Gly Leu Ser Ser Pro Val Thr Lys Ser Phe Asn Arg Gly Glu Cys *
225                 230                 235
```

<210> SEQ ID NO 2
<211> LENGTH: 239
<212> TYPE: PRT
<213> ORGANISM: Artificial Sequence
<220> FEATURE:
<223> OTHER INFORMATION: Light chain of 12.12 human anti-CD40 antibody

<400> SEQUENCE: 2

```
Met Ala Leu Pro Ala Gln Leu Leu Gly Leu Leu Met Leu Trp Val Ser
1               5                   10                  15

Gly Ser Ser Gly Asp Ile Val Met Thr Gln Ser Pro Leu Ser Leu Thr
                20                  25                  30

Val Thr Pro Gly Glu Pro Ala Ser Ile Ser Cys Arg Ser Ser Gln Ser
            35                  40                  45

Leu Leu Tyr Ser Asn Gly Tyr Asn Tyr Leu Asp Trp Tyr Leu Gln Lys
        50                  55                  60

Pro Gly Gln Ser Pro Gln Val Leu Ile Ser Leu Gly Ser Asn Arg Ala
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Met Gln Ala Arg Gln Thr Pro Phe Thr Phe Gly Pro Gly Thr Lys
        115                 120                 125

Val Asp Ile Arg Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

```
<210> SEQ ID NO 3
<211> LENGTH: 2016
<212> TYPE: DNA
<213> ORGANISM: Artificial Sequence
<220> FEATURE:
<223> OTHER INFORMATION: Coding sequence for heavy chain of 12.12 human
      anti-CD40 antibody (with introns)

<400> SEQUENCE: 3
```

| | |
|---|---:|
| atg gag ttt ggg ctg agc tgg gtt ttc ctt gtt gct att tta aga ggt | 48 |
| gtc cag tgt cag gtg cag ttg gtg gag tct ggg gga ggc gtg gtc cag | 96 |
| cct ggg agg tcc ctg aga ctc tcc tgt gca gcc tct gga ttc acc ttc | 144 |
| agt agc tat ggc atg cac tgg gtc cgc cag gct cca ggc aag ggg ctg | 192 |
| gag tgg gtg gca gtt ata tca tat gag gaa agt aat aga tac cat gca | 240 |
| gac tcc gtg aag ggc cga ttc acc atc tcc aga gac aat tcc aag atc | 288 |
| acg ctg tat ctg caa atg aac agc ctc aga act gag gac acg gct gtg | 336 |
| tat tac tgt gcg aga gat ggg ggt ata gca gca cct ggg cct gac tac | 384 |
| tgg ggc cag gga acc ctg gtc acc gtc tcc tca gca agt acc aag ggc | 432 |
| cca tcc gtc ttc ccc ctg gcg ccc gct agc aag agc acc tct ggg ggc | 480 |
| aca gcg gcc ctg ggc tgc ctg gtc aag gac tac ttc ccc gaa ccg gtg | 528 |
| acg gtg tcg tgg aac tca ggc gcc ctg acc agc ggc gtg cac acc ttc | 576 |
| ccg gct gtc cta cag tcc tca gga ctc tac tcc ctc agc agc gtg gtg | 624 |
| acc gtg ccc tcc agc agc ttg ggc acc cag acc tac atc tgc aac gtg | 672 |
| aat cac aag ccc agc aac acc aag gtg gac aag aga gtt ggt gag agg | 720 |
| cca gca cag gga ggg agg gtg tct gct gga agc cag gct cag cgc tcc | 768 |
| tgc ctg gac gca tcc cgg cta tgc agt ccc agt cca ggg cag caa ggc | 816 |
| agg ccc cgt ctg cct ctt cac ccg gag gcc tct gcc cgc ccc act cat | 864 |
| gct cag gga gag ggt ctt ctg gct ttt ccc cag gct ctg ggc agg cac | 912 |
| agg cta ggt gcc cct aac cca ggc cct gca caa agg ggc agg tgc | 960 |
| tgg gct cag acc tgc caa gag cca tat ccg gga gga ccc tgc ccc tga | 1008 |
| cct aag ccc acc cca aag gcc aaa ctc tcc act ccc tca gct cgg aca | 1056 |
| cct tct ctc ctc cca gat tcc agt aac tcc caa tct tct ctc tgc aga | 1104 |
| gcc caa atc ttg tga caa aac tca cac atg ccc acc gtg ccc agg taa | 1152 |
| gcc agc cca ggc ctc gcc ctc cag ctc aag gcg gga cag gtg ccc tag | 1200 |
| agt agc ctg cat cca ggg aca ggc ccc agc cgg gtg ctg aca cgt cca | 1248 |
| cct cca tct ctt cct cag cac ctg aac tcc tgg ggg gac cgt cag tct | 1296 |
| tcc tct tcc ccc caa aac cca agg aca ccc tca tga tct ccc gga ccc | 1344 |
| ctg agg tca cat gcg tgg tgg tgg acg tga gcc acg aag acc ctg agg | 1392 |
| tca agt tca act ggt acg tgg acg gcg tgg agg tgc ata atg cca aga | 1440 |
| caa agc cgc ggg agg agc agt aca aca gca cgt acc gtg tgg tca gcg | 1488 |
| tcc tca ccg tcc tgc acc agg act ggc tga atg gca agg agt aca agt | 1536 |
| gca agg tct cca aca agc cct cca gcc cca tcg aga aaa cca tct | 1584 |
| cca aag cca aag gtg gga ccc gtg ggg tgc gag ggc cac atg gac aga | 1632 |
| ggc cgg ctc ggc cca ccc tct gcc ctg aga gtg acc gct gta cca acc | 1680 |

```
tct gtc cct aca ggg cag ccc cga gaa cca cag gtg tac acc ctg ccc      1728 cca tcc cgg gag gag atg acc aag aac cag gtc agc ctg acc tgc ctg      1776 gtc aaa ggc ttc tat ccc agc gac atc gcc gtg gag tgg gag agc aat      1824 ggg cag ccg gag aac aac tac aag acc acg cct ccc gtg ctg gac tcc      1872 gac ggc tcc ttc ttc ctc tat agc aag ctc acc gtg gac aag agc agg      1920 tgg cag cag ggg aac gtc ttc tca tgc tcc gtg atg cat gag gct ctg      1968 cac aac cac tac acg cag aag agc ctc tcc ctg tct ccg ggt aaa tga      2016
```

<210> SEQ ID NO 4
<211> LENGTH: 469
<212> TYPE: PRT
<213> ORGANISM: Artificial Sequence
<220> FEATURE:
<223> OTHER INFORMATION: Heavy chain of 12.12 human anti-CD40 antibody

<400> SEQUENCE: 4

Met Glu Phe Gly Leu Ser Trp Val Phe Leu Val Ala Ile Leu Arg Gly
 1               5                  10                  15

Val Gln Cys Gln Val Gln Leu Val Glu Ser Gly Gly Gly Val Val Gln
                20                  25                  30

Pro Gly Arg Ser Leu Arg Leu Ser Cys Ala Ala Ser Gly Phe Thr Phe
            35                  40                  45

Ser Ser Tyr Gly Met His Trp Val Arg Gln Ala Pro Gly Lys Gly Leu
        50                  55                  60

Glu Trp Val Ala Val Ile Ser Tyr Glu Glu Ser Asn Arg Tyr His Ala
65                  70                  75                  80

Asp Ser Val Lys Gly Arg Phe Thr Ile Ser Arg Asp Asn Ser Lys Ile
                85                  90                  95

Thr Leu Tyr Leu Gln Met Asn Ser Leu Arg Thr Glu Asp Thr Ala Val
            100                 105                 110

Tyr Tyr Cys Ala Arg Asp Gly Gly Ile Ala Ala Pro Gly Pro Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

```
Ser His Glu Asp Pro Glu Val Lys Phe Asn Trp Tyr Val Asp Gly Val
290                 295                 300
Glu Val His Asn Ala Lys Thr Lys Pro Arg Glu Glu Gln Tyr Asn Ser
305                 310                 315                 320
Thr Tyr Arg Val Val Ser Val Leu Thr Val Leu His Gln Asp Trp Leu
            325                 330                 335
Asn Gly Lys Glu Tyr Lys Cys Lys Val Ser Asn Lys Ala Leu Pro Ala
            340                 345                 350
Pro Ile Glu Lys Thr Ile Ser Lys Ala Lys Gly Gln Pro Arg Glu Pro
            355                 360                 365
Gln Val Tyr Thr Leu Pro Pro Ser Arg Glu Glu Met Thr Lys Asn Gln
370                 375                 380
Val Ser Leu Thr Cys Leu Val Lys Gly Phe Tyr Pro Ser Asp Ile Ala
385                 390                 395                 400
Val Glu Trp Glu Ser Asn Gly Gln Pro Glu Asn Asn Tyr Lys Thr Thr
                405                 410                 415
Pro Pro Val Leu Asp Ser Asp Gly Ser Phe Phe Leu Tyr Ser Lys Leu
            420                 425                 430
Thr Val Asp Lys Ser Arg Trp Gln Gln Gly Asn Val Phe Ser Cys Ser
            435                 440                 445
Val Met His Glu Ala Leu His Asn His Tyr Thr Gln Lys Ser Leu Ser
450                 455                 460
Leu Ser Pro Gly Lys
465

<210> SEQ ID NO 5
<211> LENGTH: 469
<212> TYPE: PRT
<213> ORGANISM: Artificial Sequence
<220> FEATURE:
<223> OTHER INFORMATION: Heavy chain of variant of 12.12 human anti-CD40
      antibody

<400> SEQUENCE: 5

Met Glu Phe Gly Leu Ser Trp Val Phe Leu Val Ala Ile Leu Arg Gly
1               5                   10                  15
Val Gln Cys Gln Val Gln Leu Val Glu Ser Gly Gly Gly Val Val Gln
                20                  25                  30
Pro Gly Arg Ser Leu Arg Leu Ser Cys Ala Ala Ser Gly Phe Thr Phe
            35                  40                  45
Ser Ser Tyr Gly Met His Trp Val Arg Gln Ala Pro Gly Lys Gly Leu
    50                  55                  60
Glu Trp Val Ala Val Ile Ser Tyr Glu Glu Ser Asn Arg Tyr His Ala
65                  70                  75                  80
Asp Ser Val Lys Gly Arg Phe Thr Ile Ser Arg Asp Asn Ser Lys Ile
                85                  90                  95
Thr Leu Tyr Leu Gln Met Asn Ser Leu Arg Thr Glu Asp Thr Ala Val
            100                 105                 110
Tyr Tyr Cys Ala Arg Asp Gly Gly Ile Ala Ala Pro Gly Pro Asp Tyr
        115                 120                 125
Trp Gly Gln Gly Thr Leu Val Thr Val Ser Ser Ala Ser Thr Lys Gly
    130                 135                 140
Pro Ser Val Phe Pro Leu Ala Pro Ser Ser Lys Ser Thr Ser Gly Gly
145                 150                 155                 160
Thr Ala Ala Leu Gly Cys Leu Val Lys Asp Tyr Phe Pro Glu Pro Val
                165                 170                 175
```

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 6
<211> LENGTH: 239
<212> TYPE: PRT
<213> ORGANISM: Artificial Sequence
<220> FEATURE:
<223> OTHER INFORMATION: Light chain of 5.9 human anti-CD40 antibody

<400> SEQUENCE: 6

Met Ala Leu Leu Ala Gln Leu Gly Leu Leu Met Leu Trp Val Pro
1               5                   10                  15

Gly Ser Ser Gly Ala Ile Val Met Thr Gln Pro Pro Leu Ser Ser Pro
            20                  25                  30

Val Thr Leu Gly Gln Pro Ala Ser Ile Ser Cys Arg Ser Ser Gln Ser
        35                  40                  45

Leu Val His Ser Asp Gly Asn Thr Tyr Leu Asn Trp Leu Gln Gln Arg
    50                  55                  60

```
Pro Gly Gln Pro Pro Arg Leu Leu Ile Tyr Lys Phe Phe Arg Arg Leu
 65                  70                  75                  80

Ser Gly Val Pro Asp Arg Phe Ser Gly Ser Gly Ala Gly Thr Asp Phe
             85                  90                  95

Thr Leu Lys Ile Ser Arg Val Glu Ala Glu Asp Val Gly Val Tyr Tyr
            100                 105                 110

Cys Met Gln Val Thr Gln Phe Pro His Thr Phe Gly Gln Gly Thr Arg
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 7
<211> LENGTH: 474
<212> TYPE: PRT
<213> ORGANISM: Artificial Sequence
<220> FEATURE:
<223> OTHER INFORMATION: Heavy chain of 5.9 human anti-CD40 antibody

<400> SEQUENCE: 7

Met Gly Ser Thr Ala Ile Leu Ala Leu Leu Leu Ala Val Leu Gln Gly
  1               5                  10                  15

Val Cys Ala Glu Val Gln Leu Val Gln Ser Gly Ala Glu Val Lys Lys
             20                  25                  30

Pro Gly Glu Ser Leu Lys Ile Ser Cys Lys Gly Ser Gly Tyr Ser Phe
         35                  40                  45

Thr Ser Tyr Trp Ile Gly Trp Val Arg Gln Met Pro Gly Lys Gly Leu
     50                  55                  60

Glu Trp Met Gly Ile Ile Tyr Pro Gly Asp Ser Asp Thr Arg Tyr Ser
 65                  70                  75                  80

Pro Ser Phe Gln Gly Gln Val Thr Ile Ser Ala Asp Lys Ser Ile Ser
             85                  90                  95

Thr Ala Tyr Leu Gln Trp Ser Ser Leu Lys Ala Ser Asp Thr Ala Met
            100                 105                 110

Tyr Tyr Cys Ala Arg Gly Thr Ala Ala Gly Arg Asp Tyr Tyr Tyr Tyr
        115                 120                 125

Tyr Gly Met Asp Val Trp Gly Gln Gly Thr Thr Val Thr Val Ser Ser
    130                 135                 140

Ala Ser Thr Lys Gly Pro Ser Val Phe Pro Leu Ala Pro Ala Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190
```

-continued

```
Gly Val His Thr Phe Pro Ala Val Leu Gln Ser Ser Gly Leu Tyr Ser
            195                 200                 205
Leu Ser Ser Val Val Thr Val Pro Ser Ser Leu Gly Thr Gln Thr
    210                 215                 220
Tyr Ile Cys Asn Val Asn His Lys Pro Ser Asn Thr Lys Val Asp Lys
225                 230                 235                 240
Arg Val Glu Pro Lys Ser Cys Asp Lys Thr His Thr Cys Pro Pro Cys
            245                 250                 255
Pro Ala Pro Glu Leu Leu Gly Gly Pro Ser Val Phe Leu Phe Pro Pro
            260                 265                 270
Lys Pro Lys Asp Thr Leu Met Ile Ser Arg Thr Pro Glu Val Thr Cys
            275                 280                 285
Val Val Val Asp Val Ser His Glu Asp Pro Glu Val Lys Phe Asn Trp
290                 295                 300
Tyr Val Asp Gly Val Glu Val His Asn Ala Lys Thr Lys Pro Arg Glu
305                 310                 315                 320
Glu Gln Tyr Asn Ser Thr Tyr Arg Val Val Ser Val Leu Thr Val Leu
            325                 330                 335
His Gln Asp Trp Leu Asn Gly Lys Glu Tyr Lys Cys Lys Val Ser Asn
            340                 345                 350
Lys Ala Leu Pro Ala Pro Ile Glu Lys Thr Ile Ser Lys Ala Lys Gly
            355                 360                 365
Gln Pro Arg Glu Pro Gln Val Tyr Thr Leu Pro Pro Ser Arg Glu Glu
            370                 375                 380
Met Thr Lys Asn Gln Val Ser Leu Thr Cys Leu Val Lys Gly Phe Tyr
385                 390                 395                 400
Pro Ser Asp Ile Ala Val Glu Trp Glu Ser Asn Gly Gln Pro Glu Asn
            405                 410                 415
Asn Tyr Lys Thr Thr Pro Pro Val Leu Asp Ser Asp Gly Ser Phe Phe
            420                 425                 430
Leu Tyr Ser Lys Leu Thr Val Asp Lys Ser Arg Trp Gln Gln Gly Asn
            435                 440                 445
Val Phe Ser Cys Ser Val Met His Glu Ala Leu His Asn His Tyr Thr
            450                 455                 460
Gln Lys Ser Leu Ser Leu Ser Pro Gly Lys
465                 470

<210> SEQ ID NO 8
<211> LENGTH: 474
<212> TYPE: PRT
<213> ORGANISM: Artificial Sequence
<220> FEATURE:
<223> OTHER INFORMATION: Heavy chain of variant of 5.9 human anti-CD40
      antibody

<400> SEQUENCE: 8

Met Gly Ser Thr Ala Ile Leu Ala Leu Leu Leu Ala Val Leu Gln Gly
1               5                   10                  15
Val Cys Ala Glu Val Gln Leu Val Gln Ser Gly Ala Glu Val Lys Lys
            20                  25                  30
Pro Gly Glu Ser Leu Lys Ile Ser Cys Lys Gly Ser Gly Tyr Ser Phe
        35                  40                  45
Thr Ser Tyr Trp Ile Gly Trp Val Arg Gln Met Pro Gly Lys Gly Leu
    50                  55                  60
Glu Trp Met Gly Ile Ile Tyr Pro Gly Asp Ser Asp Thr Arg Tyr Ser
65                  70                  75                  80
```

-continued

```
Pro Ser Phe Gln Gly Gln Val Thr Ile Ser Ala Asp Lys Ser Ile Ser
                 85                  90                  95
Thr Ala Tyr Leu Gln Trp Ser Ser Leu Lys Ala Ser Asp Thr Ala Met
            100                 105                 110
Tyr Tyr Cys Ala Arg Gly Thr Ala Ala Gly Arg Asp Tyr Tyr Tyr Tyr
        115                 120                 125
Tyr Gly Met Asp Val Trp Gly Gln Gly Thr Thr Val Thr Val Ser Ser
130                 135                 140
Ala Ser Thr Lys Gly Pro Ser Val Phe Pro Leu Ala Pro Ser Ser Lys
145                 150                 155                 160
Ser Thr Ser Gly Gly Thr Ala Ala Leu Gly Cys Leu Val Lys Asp Tyr
                165                 170                 175
Phe Pro Glu Pro Val Thr Val Ser Trp Asn Ser Gly Ala Leu Thr Ser
            180                 185                 190
Gly Val His Thr Phe Pro Ala Val Leu Gln Ser Ser Gly Leu Tyr Ser
        195                 200                 205
Leu Ser Ser Val Val Thr Val Pro Ser Ser Ser Leu Gly Thr Gln Thr
210                 215                 220
Tyr Ile Cys Asn Val Asn His Lys Pro Ser Asn Thr Lys Val Asp Lys
225                 230                 235                 240
Arg Val Glu Pro Lys Ser Cys Asp Lys Thr His Thr Cys Pro Pro Cys
                245                 250                 255
Pro Ala Pro Glu Leu Leu Gly Gly Pro Ser Val Phe Leu Phe Pro Pro
            260                 265                 270
Lys Pro Lys Asp Thr Leu Met Ile Ser Arg Thr Pro Glu Val Thr Cys
        275                 280                 285
Val Val Val Asp Val Ser His Glu Asp Pro Glu Val Lys Phe Asn Trp
290                 295                 300
Tyr Val Asp Gly Val Glu Val His Asn Ala Lys Thr Lys Pro Arg Glu
305                 310                 315                 320
Glu Gln Tyr Asn Ser Thr Tyr Arg Val Val Ser Val Leu Thr Val Leu
                325                 330                 335
His Gln Asp Trp Leu Asn Gly Lys Glu Tyr Lys Cys Lys Val Ser Asn
            340                 345                 350
Lys Ala Leu Pro Ala Pro Ile Glu Lys Thr Ile Ser Lys Ala Lys Gly
        355                 360                 365
Gln Pro Arg Glu Pro Gln Val Tyr Thr Leu Pro Pro Ser Arg Glu Glu
370                 375                 380
Met Thr Lys Asn Gln Val Ser Leu Thr Cys Leu Val Lys Gly Phe Tyr
385                 390                 395                 400
Pro Ser Asp Ile Ala Val Glu Trp Glu Ser Asn Gly Gln Pro Glu Asn
                405                 410                 415
Asn Tyr Lys Thr Thr Pro Pro Val Leu Asp Ser Asp Gly Ser Phe Phe
            420                 425                 430
Leu Tyr Ser Lys Leu Thr Val Asp Lys Ser Arg Trp Gln Gln Gly Asn
        435                 440                 445
Val Phe Ser Cys Ser Val Met His Glu Ala Leu His Asn His Tyr Thr
450                 455                 460
Gln Lys Ser Leu Ser Leu Ser Pro Gly Lys
465                 470
```

-continued

```
<210> SEQ ID NO 9
<211> LENGTH: 612
<212> TYPE: DNA
<213> ORGANISM: Homo sapiens
<220> FEATURE:
<221> NAME/KEY: CDS
<222> LOCATION: (1)...(612)
<221> NAME/KEY: misc_feature
<222> LOCATION: (0)...(0)
<223> OTHER INFORMATION: Coding sequence for short isoform of human CD40

<400> SEQUENCE: 9 atg gtt cgt ctg cct ctg cag tgc gtc ctc tgg ggc tgc ttg ctg acc      48
Met Val Arg Leu Pro Leu Gln Cys Val Leu Trp Gly Cys Leu Leu Thr
1               5                   10                  15 gct gtc cat cca gaa cca ccc act gca tgc aga gaa aaa cag tac cta      96
Ala Val His Pro Glu Pro Pro Thr Ala Cys Arg Glu Lys Gln Tyr Leu
            20                  25                  30 ata aac agt cag tgc tgt tct ttg tgc cag cca gga cag aaa ctg gtg      144
Ile Asn Ser Gln Cys Cys Ser Leu Cys Gln Pro Gly Gln Lys Leu Val
        35                  40                  45 agt gac tgc aca gag ttc act gaa acg gaa tgc ctt cct tgc ggt gaa      192
Ser Asp Cys Thr Glu Phe Thr Glu Thr Glu Cys Leu Pro Cys Gly Glu
50                  55                  60 agc gaa ttc cta gac acc tgg aac aga gag aca cac tgc cac cag cac      240
Ser Glu Phe Leu Asp Thr Trp Asn Arg Glu Thr His Cys His Gln His
65                  70                  75                  80 aaa tac tgc gac ccc aac cta ggg ctt cgg gtc cag cag aag ggc acc      288
Lys Tyr Cys Asp Pro Asn Leu Gly Leu Arg Val Gln Gln Lys Gly Thr
                85                  90                  95 tca gaa aca gac acc atc tgc acc tgt gaa gaa ggc tgg cac tgt acg      336
Ser Glu Thr Asp Thr Ile Cys Thr Cys Glu Glu Gly Trp His Cys Thr
            100                 105                 110 agt gag gcc tgt gag agc tgt gtc ctg cac cgc tca tgc tcg ccc ggc      384
Ser Glu Ala Cys Glu Ser Cys Val Leu His Arg Ser Cys Ser Pro Gly
        115                 120                 125 ttt ggg gtc aag cag att gct aca ggg gtt tct gat acc atc tgc gag      432
Phe Gly Val Lys Gln Ile Ala Thr Gly Val Ser Asp Thr Ile Cys Glu
    130                 135                 140 ccc tgc cca gtc ggc ttc ttc tcc aat gtg tca tct gct ttc gaa aaa      480
Pro Cys Pro Val Gly Phe Phe Ser Asn Val Ser Ser Ala Phe Glu Lys
145                 150                 155                 160 tgt cac cct tgg aca agg tcc cca gga tcg gct gag agc cct ggt ggt      528
Cys His Pro Trp Thr Arg Ser Pro Gly Ser Ala Glu Ser Pro Gly Gly
                165                 170                 175 gat ccc cat cat ctt cgg gat cct gtt tgc cat cct ctt ggt gct ggt      576
Asp Pro His His Leu Arg Asp Pro Val Cys His Pro Leu Gly Ala Gly
            180                 185                 190 ctt tat caa aaa ggt ggc caa gaa gcc aac caa taa                      612
Leu Tyr Gln Lys Gly Gly Gln Glu Ala Asn Gln *
        195                 200

<210> SEQ ID NO 10
<211> LENGTH: 203
<212> TYPE: PRT
<213> ORGANISM: Homo sapiens

<400> SEQUENCE: 10

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30
```

```
Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
 50                  55                  60

Ser Glu Phe Leu Asp Thr Trp Asn Arg Glu Thr His Cys His Gln His
 65                  70                  75                  80

Lys Tyr Cys Asp Pro Asn Leu Gly Leu Arg Val Gln Gln Lys Gly Thr
                 85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Arg Ser Pro Gly Ser Ala Glu Ser Pro Gly Gly
                165                 170                 175

Asp Pro His His Leu Arg Asp Pro Val Cys His Pro Leu Gly Ala Gly
            180                 185                 190

Leu Tyr Gln Lys Gly Gly Gln Glu Ala Asn Gln
        195                 200

<210> SEQ ID NO 11
<211> LENGTH: 834
<212> TYPE: DNA
<213> ORGANISM: Homo sapiens
<220> FEATURE:
<221> NAME/KEY: CDS
<222> LOCATION: (1)...(834)
<221> NAME/KEY: misc_feature
<222> LOCATION: (0)...(0)
<223> OTHER INFORMATION: Coding sequence for long isoform of human CD40

<400> SEQUENCE: 11 atg gtt cgt ctg cct ctg cag tgc gtc ctc tgg ggc tgc ttg ctg acc      48
Met Val Arg Leu Pro Leu Gln Cys Val Leu Trp Gly Cys Leu Leu Thr
  1               5                  10                  15 gct gtc cat cca gaa cca ccc act gca tgc aga gaa aaa cag tac cta      96
Ala Val His Pro Glu Pro Pro Thr Ala Cys Arg Glu Lys Gln Tyr Leu
             20                  25                  30 ata aac agt cag tgc tgt tct ttg tgc cag cca gga cag aaa ctg gtg     144
Ile Asn Ser Gln Cys Cys Ser Leu Cys Gln Pro Gly Gln Lys Leu Val
        35                  40                  45 agt gac tgc aca gag ttc act gaa acg gaa tgc ctt cct tgc ggt gaa     192
Ser Asp Cys Thr Glu Phe Thr Glu Thr Glu Cys Leu Pro Cys Gly Glu
 50                  55                  60 agc gaa ttc cta gac acc tgg aac aga gag aca cac tgc cac cag cac     240
Ser Glu Phe Leu Asp Thr Trp Asn Arg Glu Thr His Cys His Gln His
 65                  70                  75                  80 aaa tac tgc gac ccc aac cta ggg ctt cgg gtc cag cag aag ggc acc     288
Lys Tyr Cys Asp Pro Asn Leu Gly Leu Arg Val Gln Gln Lys Gly Thr
                 85                  90                  95 tca gaa aca gac acc atc tgc acc tgt gaa gaa ggc tgg cac tgt acg     336
Ser Glu Thr Asp Thr Ile Cys Thr Cys Glu Glu Gly Trp His Cys Thr
            100                 105                 110 agt gag gcc tgt gag agc tgt gtc ctg cac cgc tca tgc tcg ccc ggc     384
Ser Glu Ala Cys Glu Ser Cys Val Leu His Arg Ser Cys Ser Pro Gly
        115                 120                 125
```

```
ttt ggg gtc aag cag att gct aca ggg gtt tct gat acc atc tgc gag    432
Phe Gly Val Lys Gln Ile Ala Thr Gly Val Ser Asp Thr Ile Cys Glu
    130                 135                 140 ccc tgc cca gtc ggc ttc ttc tcc aat gtg tca tct gct ttc gaa aaa    480
Pro Cys Pro Val Gly Phe Phe Ser Asn Val Ser Ser Ala Phe Glu Lys
145                 150                 155                 160 tgt cac cct tgg aca agc tgt gag acc aaa gac ctg gtt gtg caa cag    528
Cys His Pro Trp Thr Ser Cys Glu Thr Lys Asp Leu Val Val Gln Gln
                165                 170                 175 gca ggc aca aac aag act gat gtt gtc tgt ggt ccc cag gat cgg ctg    576
Ala Gly Thr Asn Lys Thr Asp Val Val Cys Gly Pro Gln Asp Arg Leu
            180                 185                 190 aga gcc ctg gtg gtg atc ccc atc atc ttc ggg atc ctg ttt gcc atc    624
Arg Ala Leu Val Val Ile Pro Ile Ile Phe Gly Ile Leu Phe Ala Ile
                195                 200                 205 ctc ttg gtg ctg gtc ttt atc aaa aag gtg gcc aag aag cca acc aat    672
Leu Leu Val Leu Val Phe Ile Lys Lys Val Ala Lys Lys Pro Thr Asn
210                 215                 220 aag gcc ccc cac ccc aag cag gaa ccc cag gag atc aat ttt ccc gac    720
Lys Ala Pro His Pro Lys Gln Glu Pro Gln Glu Ile Asn Phe Pro Asp
225                 230                 235                 240 gat ctt cct ggc tcc aac act gct gct cca gtg cag gag act tta cat    768
Asp Leu Pro Gly Ser Asn Thr Ala Ala Pro Val Gln Glu Thr Leu His
                245                 250                 255 gga tgc caa ccg gtc acc cag gag gat ggc aaa gag agt cgc atc tca    816
Gly Cys Gln Pro Val Thr Gln Glu Asp Gly Lys Glu Ser Arg Ile Ser
                260                 265                 270 gtg cag gag aga cag tga                                            834
Val Gln Glu Arg Gln *
                275

<210> SEQ ID NO 12
<211> LENGTH: 277
<212> TYPE: PRT
<213> ORGANISM: Homo sapiens

<400> SEQUENCE: 12

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
                20                  25                  30

Ile Asn Ser Gln Cys Cys Ser Leu Cys Gln Pro Gly Gln Lys Leu Val
            35                  40                  45

Ser Asp Cys Thr Glu Phe Thr Glu Thr Glu Cys Leu Pro Cys Gly Glu
        50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160
```

```
Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

Leu Leu Val Leu Val Phe Ile Lys Lys Val Ala Lys Lys Pro Thr Asn
    210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
                260                 265                 270

Val Gln Glu Arg Gln
            275
```